US008647887B2

(12) United States Patent
Trowell et al.

(10) Patent No.: US 8,647,887 B2
(45) Date of Patent: Feb. 11, 2014

(54) MEASURING G PROTEIN COUPLED RECEPTOR ACTIVATION

(75) Inventors: Stephen Charles Trowell, Oxley (AU); Irene Mary Horne, Yass (AU); Helen Dacres, Lyons (AU); Virginia Leitch, Belconnen (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 13/141,661

(22) PCT Filed: Jan. 28, 2010

(86) PCT No.: PCT/AU2010/000080
§ 371 (c)(1),
(2), (4) Date: Dec. 13, 2011

(87) PCT Pub. No.: WO2010/085844
PCT Pub. Date: Aug. 5, 2010

(65) Prior Publication Data
US 2012/0077210 A1    Mar. 29, 2012

Related U.S. Application Data

(60) Provisional application No. 61/148,271, filed on Jan. 29, 2009.

(51) Int. Cl.
G01N 33/567    (2006.01)
C07K 14/705    (2006.01)
C07K 16/00    (2006.01)

(52) U.S. Cl.
USPC ............ 436/501; 435/7.1; 435/7.2; 435/7.21; 435/69.7; 536/23.4

(58) Field of Classification Search
None
See application file for complete search history.

(56) References Cited

U.S. PATENT DOCUMENTS

| | | | |
|---|---|---|---|
| 5,196,524 A | 3/1993 | Gustafson et al. |
| 5,219,737 A | 6/1993 | Kajiyama et al. |
| 5,229,285 A | 7/1993 | Kajiyama et al. |
| 5,670,356 A | 9/1997 | Sherf et al. |
| 5,792,294 A | 8/1998 | Randazzo et al. |
| 5,843,746 A | 12/1998 | Tatsumi et al. |
| 6,824,990 B1 | 11/2004 | Blumer |
| 6,949,377 B2 | 9/2005 | Ho |
| 7,320,875 B2 | 1/2008 | Abrignani |
| 2001/0023078 A1 | 9/2001 | Bawendi et al. |
| 2002/0048811 A1 | 4/2002 | Devreotes et al. |
| 2002/0168641 A1 | 11/2002 | Mortensen et al. |
| 2003/0017538 A1 | 1/2003 | Miyawaki et al. |
| 2003/0203404 A1 | 10/2003 | Joly |
| 2003/0220502 A1 | 11/2003 | Waggoner et al. |
| 2004/0162423 A1 | 8/2004 | Czerney et al. |
| 2005/0118619 A1 | 6/2005 | Xia et al. |
| 2006/0183247 A1 | 8/2006 | Kim et al. |
| 2006/0205015 A1 | 9/2006 | Ansanay et al. |
| 2006/0272037 A1 | 11/2006 | Bauerle |
| 2007/0104709 A1* | 5/2007 | Li et al. ............... 424/144.1 |
| 2007/0128659 A1 | 6/2007 | Czerney et al. |

FOREIGN PATENT DOCUMENTS

| | | |
|---|---|---|
| EP | 1295121 | 3/2006 |
| EP | 1581811 | 10/2008 |
| JP | 2004053416 | 2/2004 |
| WO | WO 9840477 | 9/1998 |
| WO | WO 9949019 | 9/1999 |
| WO | WO 9964519 | 12/1999 |
| WO | WO 0008054 | 2/2000 |
| WO | WO 0014271 | 3/2000 |
| WO | WO 0024878 | 5/2000 |
| WO | WO 0037448 | 6/2000 |
| WO | WO 0047693 | 8/2000 |
| WO | WO 0055631 | 9/2000 |
| WO | WO 0146691 | 6/2001 |
| WO | WO 0146694 | 6/2001 |
| WO | WO 0162919 | 8/2001 |
| WO | WO 0166723 | 9/2001 |
| WO | WO 0168824 | 9/2001 |
| WO | WO 0190147 | 11/2001 |
| WO | WO 0208245 | 1/2002 |

(Continued)

OTHER PUBLICATIONS

Pfleger et al., Monitoring the formation of dynamic G-protein-coupled receptor-protein complexes in living cells, 2005, Biochem. J. 385:625-637.*
Hofmann & Stoffel (1993) "A Database of Membrane Spanning Protein Segments" Biol. Chem. 374:166.
Aloni et al. (2006) "Ancient genomic architecture for mammalian olfactory receptor clusters" Genome Biol. 7(10):R88.
Ayoub et al. (2002) "Monitoring of ligand-independent dimerization and ligand-induced conformational changes of melatonin receptors in living cells by bioluminescence resonance energy transfer" J. Biol. Chem. 277(24):21522-28.
Boute et al. (2002) "The Use of Resonance Energy Transfer in High-Throughput Screening: BRET versus FRET" Trends Pharmacol Sci (23(8):351-354.

(Continued)

*Primary Examiner* — John Ulm
(74) *Attorney, Agent, or Firm* — Carol L. Francis; Bozicevic, Field & Francis LLP

(57) ABSTRACT

The present invention relates to methods and polypeptides for detecting a compound in a sample. In particular, the present invention relates to the use of a cell-free composition comprising at least one G protein coupled receptor embedded in a lipid Mayer which when expressed in a cell the N-terminus of the G protein coupled receptor, or subunits thereof, is outside the cell and the C-terminus is inside the cell, and which is capable of binding the compound. Optionally, the composition also comprises at least one accessory molecule that directly or indirectly binds an intracellular loop and/or the C-terminus of the G protein coupled receptor. The G protein coupled receptor, and/or accessory molecule when present, in combination comprise a bioluminescent protein and an acceptor molecule, which enables bioluminescent resonance energy transfer (BRET) to be used to detect the compound binding the receptor.

19 Claims, 16 Drawing Sheets

(56) References Cited

FOREIGN PATENT DOCUMENTS

Figure 1:
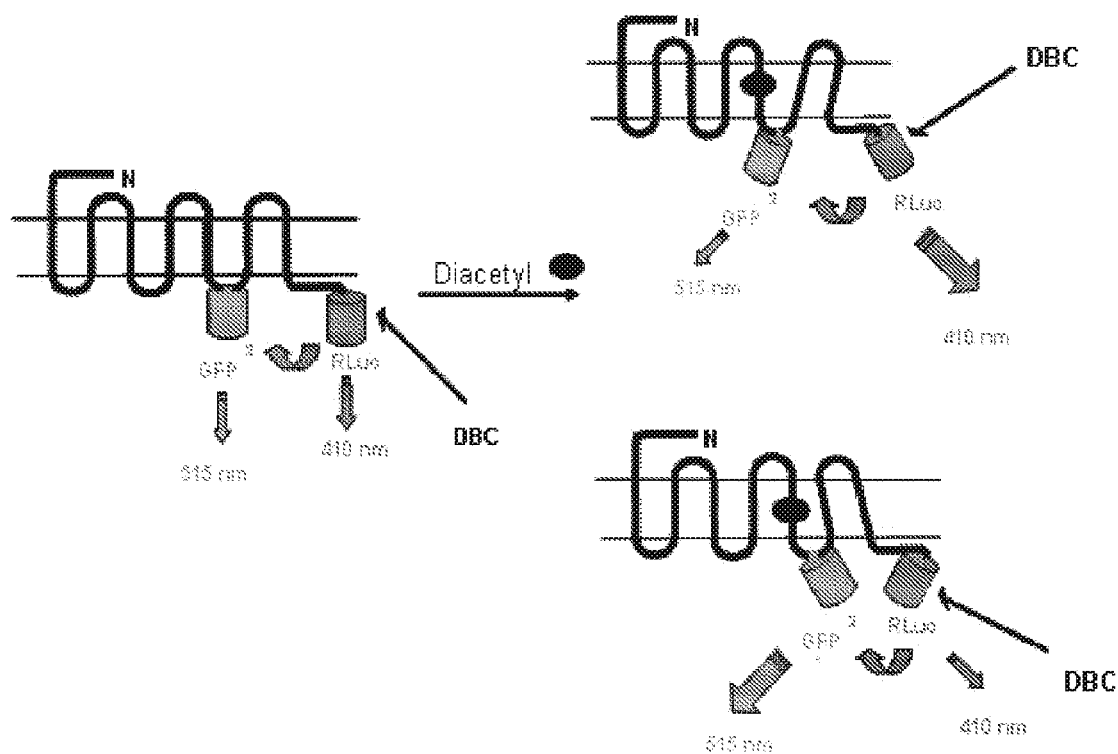

| | | |
|---|---|---|
| WO | WO 0226890 | 4/2002 |
| WO | WO 0233102 | 4/2002 |
| WO | WO 0242323 | 5/2002 |
| WO | WO 0244720 | 6/2002 |
| WO | WO 02093129 | 11/2002 |
| WO | WO 03019145 | 3/2003 |
| WO | WO 03033650 | 4/2003 |
| WO | WO 03040024 | 5/2003 |
| WO | WO 03104460 | 12/2003 |
| WO | WO 03104461 | 12/2003 |
| WO | WO 2004009788 | 1/2004 |
| WO | WO 2004018671 | 3/2004 |
| WO | WO 2004034054 | 4/2004 |
| WO | WO 2004072608 | 8/2004 |
| WO | 2004057333 | 10/2004 |
| WO | WO 2005022161 | 3/2005 |
| WO | WO 2005026730 | 3/2005 |
| WO | WO 2005030930 | 4/2005 |
| WO | WO 2005050182 | 6/2005 |
| WO | WO 2005054464 | 6/2005 |
| WO | WO 2005057333 | 6/2005 |
| WO | WO 2005089409 | 9/2005 |
| WO | 2005105850 | 11/2005 |
| WO | WO 2006017751 | 2/2006 |
| WO | WO 2006024041 | 3/2006 |
| WO | WO 2006035208 | 4/2006 |
| WO | WO 2006037226 | 4/2006 |
| WO | WO 2006042907 | 4/2006 |
| WO | WO 2006042912 | 4/2006 |
| WO | WO 2006051944 | 5/2006 |
| WO | 2006086883 | 8/2006 |
| WO | WO 2006083382 | 8/2006 |
| WO | WO 2006087163 | 8/2006 |
| WO | WO 2006099160 | 9/2006 |
| WO | WO 2007018315 | 2/2007 |
| WO | WO 2007019382 | 2/2007 |
| WO | WO 2007019634 | 2/2007 |
| WO | WO 2007028921 | 3/2007 |

OTHER PUBLICATIONS

Brenner (1974) "The genetics of *Caenorhabditis elegans*" Genetics 77(1):71-94.
Buck & Axel (1991) "A novel multigene family may encode odorant receptors: a molecular basis for odor recognition" Cell 65(1): 175-187.
Celić et al. (2003) "Sequences in the intracellular loops of the yeast pheromone receptor Ste2p required for G protein activation" Biochemistry 42(10):3004-3017.
Charest et al. (2005) "Monitoring agonist-promoted conformational changes of beta-arrestin in living cells by intramolecular BRET" EMBO Reports 6(4):334-340.
Cuppen et al. (2003) "Proteins interacting with *Caenorhabditis elegans* Galpha subunits" Comp Funct Genomics 4(5):479-491.
Dacres et al. (2009) "Direct comparison of bioluminescence-based resonance energy transfer methods for monitoring of proteolytic cleavage" Anal. Biochem. 385(2):194-202.
Dacres et al. (2010) "Experimental Determination of the Förster Distance for Two Commonly used Bioluminescent Resonance Energy Transfer Pairs" Anal Chem 82(1):432-435.
Dacres et al. (2011) "Greatly Enhanced Detection of a Volatile Ligand at Femtomolar Levels Using Bioluminescence Resonance Energy Transfer (BRET)" Biosens Bioelectron 29(11):119-124.
Day et al. (2004) "Evolution of beetle bioluminescence: the origin of beetle luciferin" Luminescence 19(1):8-20.
De Wet et al. (1987) "Firefly luciferase gene: structure and expression in mammalian cells" Mol. Cell. Biol. 7(2):725-737.
Evers et al. (2006) "Quantitative understanding of the energy transfer between fluorescent proteins connected via flexible peptide linkers" Biochemistry 45(44):13183-13192.
Flдmesser et al. (2006) "Widespread ectopic expression of olfactory receptor genes" BMC Genomics.7:121.
Frishman & Argos (1997) "Seventy-five percent accuracy in protein secondary structure prediction" Proteins 27(3):329-335.
Fuchs et al. (2001) "The human olfactory subgenome: from sequence to structure and evolution" Human Genetics 108(1):1-13.
Gaillard et al. (2004) "Olfactory receptors" Cell Mol Life Sci 61(4):456-469.
Ghanouni et al. (2001) "Agonist-induced conformational changes in the G-protein-coupling domain of the beta 2 adrenergic receptor" Proc. Natl. Acad. Sci. USA 98(11):5997-96002.
Glusman et al (2001) "The complete human olfactory subgenome" Genome Res. 11(5):685-702.
Glusman et al. (2000) "Sequence, structure, and evolution of a complete human olfactory receptor gene cluster" Genomics 63(2):227-245.
Glusman et al. (2000) "The olfactory receptor gene superfamily data mining, classification, and nomenclature" Mammalian Genome 11(11):1016-1023.
Graschopf et al. (2001) "The yeast plasma membrane protein Alr1 controls Mg2+ homeostasis and is subject to Mg2+-dependent control of its synthesis and degradation" J. Biol. Chem. 276(19):16216-16222.
Greer & Szalay (2002) "Imaging of light emission from the expression of luciferases in living cells and organisms: a review" Luminescence 17(1):43-74.
Harayama (1998) "Artificial evolution by DNA shuffling" Trends Biotechnol. 16(2):76-82.
Hastings (1996) "Chemistries and colors of bioluminescent reactions: a review" Gene 173(1 Spec No):5-11.
Hoffmann et al. (2005) "A FlAsH-based FRET approach to determine G protein-coupled receptor activation in living cells" Nat Methods 2(3):171-176.
Hofmann et al. (2009) "A G protein-coupled receptor at work: the rhodopsin model" Trends Biochem Sci 34(11):540-552.
Hushpulian et al. (2007) "Biocatalytic properties of recombinant tobacco peroxidase in chemiluminescent reaction" Biotransformation 25(2-4):163-170.
Inouye & Shimomura (1997) "The use of *Renilla* luciferase, *Oplophorus* luciferase, and apoaequorin as bioluminescent reporter protein in the presence of coelenterazine analogues as substrate" Biochem. Biophys. Res. Commun. 233(2):349-353.
Issad & Jockers (2006) "Bioluminescence resonance energy transfer to monitor protein-protein interactions" Methods Mol. Biol. 332:195-209.
Jansen et al. (1999) "The complete family of genes encoding G proteins of *Caenorhabditis elegans*" Nat. Genet. 21(4):414-419.
Kaiser et al. (2008) "Efficient cell-free production of olfactory receptors: detergent optimization, structure, and ligand binding analyses" Proc Natl Acad Sci U S A 105(41):15726-31.
Klein et al. (1984) "Prediction of protein function from sequence properties. Discriminant analysis of a data base" Biochim. Biophys. Acta 787(3):221-226.
Kobilka et al. (2007) "G protein coupled receptor structure and activation" Biochimica et Biophysica Acta1768(4):794-807.
Lander et al. (2001) "Initial sequencing and analysis of the human genome" Nature 409(6822):860-921.
Li et al. (2009) "A fluorescent probe for diacetyl detection" J Fluoresc 19(4):601-606.
Lisenbee et al. (2007) "Mapping the architecture of secretin receptors with intramolecular fluorescence resonance energy transfer using acousto-optic tunable filter-based spectral imaging" Mol Endocrinol 21(8):1997-2008.
Lohse et al. (2003) "Direct optical recording of intrinsic efficacy at a G protein-coupled receptor" Life Sci. 74(2-3):397-404.
Lohse et al. (2007) "Monitoring receptor signaling by intramolecular FRET" Curr Opin Pharmacology 7: 547-553.
Lorenz et al. (1991) "Isolation and expression of a cDNA encoding *Renilla reniformis* luciferase" Proc. Natl. Acad. Sci. USA 88(10):4438-4442.
Macciola et al (2008) "Rapid gas-chromatographic method for the determination of diacetyl in milk, fermented milk and butter" Food Control 19:873-878.
Milligan & Rees (1999) "Chimaeric G alpha proteins: their potential use in drug discovery" Trends Pharmacol. Sci. 20(3):118- 124.

(56) References Cited

OTHER PUBLICATIONS

Morré et al. (1994) "Plasma and internal membranes from cultured mammalian cells" Methods Enzymol. 228:448-450 9.
Nakanishi et al. (2006) "FRET-based monitoring of conformational change of the beta2 adrenergic receptor in living cells" Biochem Biophys Res Commun 343(4):1191-1196.
Needleman & Wunsch (1970) "A general method applicable to the search for similarities in the amino acid sequence of two proteins" J. Mol Biol. 45(3):443-453.
Neves et al. (2002) "G protein pathways" Science 296(5573):1636-1639.
Niimura & Nei (2003) "Evolution of olfactory receptor genes in the human genome" Proc. Natl. Acad. Sci. USA. 100(21):12235-12240.
Oldenburg (1998) "Chapter 30: Current and Future Trends in High Throughput Screening for Drug Delivery" Annu. Rep. Med. Chem. 33:301-311.
Oldham & Hamm (2008) "Heterotrimeric G protein activation by G-protein-coupled receptors" Nature 9(1):60-71.
Olender et al.(2004) "The canine olfactory subgenome" Genomics. 83(3):361-372.
Olender et al.(2004) "The olfactory receptor universe—from whole genome analysis to structure and evolution" Genet Mol Res. 3(4):545-53.
Persson & Argos (1994) "Prediction of transmembrane segments in proteins utilising multiple sequence alignments" J. Mol. Biol. 237(2):182-192.
Persson & Jergil (1994) "Purification of plasma membranes by aqueous two-phase affinity partitioning" Anal Biochem 204(1):131-136.
Pfleger & Eidne (2005) "Monitoring the Formation of Dynamic G-Protein-Coupled Receptor-Protein Complexes in Living Cells" Biochem J 385(Pt 3):625-637.
Pfleger & Eidne (2006) "Illuminating insights into protein-protein interactions using bioluminescence resonance energy transfer (BRET)" Nature Methods 3(3):165-174.
Pilpel & Lancet (1999) "The variable and conserved interfaces of modeled olfactory receptor proteins" Protein Science 8(5):969-77.
Piston et al. (2007) "Fluorescent protein FRET: the good, the bad and the ugly" TRENDS Biochem Sci 32(9):407-414.
Pope (1999) "Homogeneous fluorescence readouts for miniaturized high-throughput screening: theory and practice" Drug Discov Today 4(8):350-362.
Rieder & Emr (2001) "Isolation of subcellular fractions from the yeast *Saccharomyces cerevisiae*" Curr. Protocol. Cell. Biol. Ch. 3; Unit 3.8.
Robertson (1998) "Two large families of chemoreceptor genes in the nematodes *Caenorhabditis elegans* and *Caenorhabditis briggsae* reveal extensive gene duplication, diversification, movement, and intron loss" Genome Research 8(5):449-463.
Robertson (2001) "Updating the str and srj (stl) families of chemoreceptors in *Caenorhabditis nematodes* reveals frequent gene movement within and between chromosomes" Chem Senses 26(2):151-159.
Rochais et al. (2007) "Real-time optical recording of betal-adrenergic receptor activation reveals supersensitivity of the Arg389 variant to carvedilol" Journal Clin Invest 117(1):229-235.
Sengupta et al. (1996) "odr-10 encodes a seven transmembrane domain olfactory receptor required for responses to the odorant diacetyl" Cell 84(6):899-909.
Sharon et al.(1998) "Genome dynamics, evolution, and protein modeling in the olfactory receptor gene superfamily" Ann N Y Acad Sci. 855:182-93.
Spencer (1998) "High-throughput screening of historic collections: observations on file size, biological targets, and file diversity" Biotechnol. Bioeng. 61(1):61-67.
Strop et al. (2007) "The structure of the yeast plasma membrane SNARE complex reveals destabilizing water-filled cavities" J. Biol. Chem. 283(2):1113-1119.
Troemel et al. (1995) "Divergent seven transmembrane receptors are candidate chemosensory receptors in *C. elegans*" Cell 83(2):207-218.
Trueheart & Fink (1989) "The yeast cell fusion protein FUS1 is O-glycosylated and spans the plasma membrane" Proc. Natl. Acad. Sci. USA. 86(24):9916-9920.
Tsien (1998) "The green fluorescent protein" Ann. Rev. Biochem. 63:509-544.
Verhaegen et al. (2002) "Recombinant *Gaussia* luciferase. Overexpression, purification, and analytical application of a bioluminescent reporter for DNA hybridization" Anal. Chem. 74(17):4378-4385.
Vilardaga (2003) "Measurement of the millisecond activation switch of G protein-coupled receptors in living cells" Nat Biotechnol 21(7):807-812.
Viviani (2002) "The origin, diversity, and structure function relationships of insect luciferases" Cell. Mol. Life Sci. 59(11):1833-1850.
Von Heijne (1992) "Membrane protein structure prediction. Hydrophobicity analysis and the positive-inside rule" J.Mol.Biol. 225(2):487-494.
Wang et al (1997) "The *Renilla* Luciferase-Modified GFP Fusion Protein Is Functional in Transformed Cells" Bioluminescence and Chemiluminescence: Molecular Reporting with Photons, Wiley, NY, pp. 419-422.
Xu et al. (1999) "A bioluminescence resonance energy transfer (BRET) system: application to interacting circadian clock proteins" Proc. Natl. Acad. Sci. USA 96(1):151-156.
Young et al. (2002) "Different evolutionary processes shaped the mouse and human olfactory receptor gene families" J. Human Mol. Genet. 11(5):535-4.
Zhang & Firestein (2002) "The Olfactory Receptor Gene Superfamily of the Mouse" Nat. Neurosci. 5(2):124-133.
Zhang et al. (1997) "The *Caenorhabditis elegans* seven-transmembrane protein ODR-10 functions as an odorant receptor in mammalian cells" Proc. Natl. Acad. Sci. USA 94(22):12162-12167.
Zozulya et al. (2001) "The human olfactory receptor repertoire" Genome Biol. 2:0018.1-0018.12.
Marullo, Stefano and Bouvier, Michel, 2007, "Resonance energy transfer approaches in molecular pharmacology and beyond", Trends in Pharmacological Sciences, 28(8):362-365.

\* cited by examiner

SEQUENCE LISTING

<160> NUMBER OF SEQ ID NOS: 56

<210> SEQ ID NO 1
<211> LENGTH: 339
<212> TYPE: PRT
<213> ORGANISM: Caenorhabditis elegans

<400> SEQUENCE: 1

```
Met Ser Gly Glu Leu Trp Ile Thr Leu Val Asp Thr Ala Asp Ile Val
1               5                   10                  15

Gly Val Thr Leu Thr Phe Cys Val Asn Ile Val Leu Leu Gly Leu Leu
                20                  25                  30

Lys Thr Arg Gly Lys Asn Leu Gly Thr Tyr Lys Tyr Leu Met Ala Phe
            35                  40                  45

Phe Ser Val Phe Ser Ile Phe Tyr Ala Ile Ile Glu Phe Ile Leu Arg
    50                  55                  60

Pro Ile Met His Ile Glu Asn Thr Thr Phe Phe Leu Ile Ser Arg Lys
65                  70                  75                  80

Arg Phe Asn Tyr Ser Thr Lys Leu Gly Lys Ile Asn Ser Ala Phe Tyr
                85                  90                  95

Cys Ala Cys Phe Ala Thr Ser Phe Val Val Ser Gly Val His Phe Val
            100                 105                 110

Tyr Arg Tyr Phe Ala Thr Cys Lys Pro Asn Leu Leu Arg Leu Phe Asn
        115                 120                 125

Leu Pro Thr Leu Leu Leu Trp Pro Leu Gly Cys Ser Val Pro Val Thr
    130                 135                 140

Met Trp Ala Ser Val Ser Tyr Phe Leu Tyr Pro Asp Thr Glu Tyr Thr
145                 150                 155                 160

Glu Ala Ala Val Thr Asn Val Leu Asn Asn His Tyr Asn Trp Ile Lys
                165                 170                 175

Lys Glu Asn Val Ser Tyr Ile Ala Tyr Val Tyr Tyr Gln Tyr Glu Asn
            180                 185                 190

Gly Val Arg His Ile Tyr Leu Lys Asn Leu Leu Gly Cys Phe Val His
        195                 200                 205

Tyr Phe Val Met Ser Met Thr Phe Val Val Met Phe Tyr Cys Gly Tyr
    210                 215                 220

Ala Thr Trp Lys Thr Met Asn Glu His Lys Asp Val Ser Asp Arg Thr
225                 230                 235                 240

Arg Ala Leu Gln Lys Gln Leu Phe Lys Ala Leu Val Leu Gln Thr Leu
                245                 250                 255

Ile Pro Thr Ile Phe Met Tyr Ala Pro Thr Gly Val Met Phe Ile Ala
            260                 265                 270
```

```
Pro Phe Phe Asp Val Asn Leu Asn Ala Asn Ala Asn Phe Ile Val Phe
            275                 280                 285

Cys Ser Phe Leu Tyr Pro Gly Leu Asp Pro Leu Ile Leu Ile Leu Ile
        290                 295                 300

Ile Arg Asp Phe Arg Arg Thr Ile Phe Asn Phe Leu Cys Gly Lys Lys
305                 310                 315                 320

Asn Ser Val Asp Glu Ser Arg Ser Thr Thr Arg Ala Asn Leu Ser Gln
                325                 330                 335

Val Pro Thr

<210> SEQ ID NO 2
<211> LENGTH: 346
<212> TYPE: PRT
<213> ORGANISM: Caenorhabditis elegans

<400> SEQUENCE: 2

Met Ser Gly Gln Leu Trp Leu Ala Leu Val Asp Ala Ala Asp Met Val
1               5                   10                  15

Gly Phe Thr Leu Thr Ile Ser Ile Asn Ile Ile Leu Leu Gly Leu Ile
            20                  25                  30

Arg Thr Arg Gly Lys Thr Leu Gly Thr Tyr Lys Tyr Leu Met Ser Phe
        35                  40                  45

Phe Ser Phe Phe Ser Ile Phe Tyr Ala Ile Val Glu Ser Ile Leu Arg
    50                  55                  60

Pro Ile Met His Ile Glu Asn Thr Thr Phe Phe Leu Ile Ser Arg Lys
65                  70                  75                  80

Arg Phe Asp Tyr Ser Thr Arg Leu Gly Lys Ile Asn Ser Ala Phe Tyr
                85                  90                  95

Cys Ala Cys Phe Ala Thr Ser Phe Val Leu Ser Ala Val His Phe Val
            100                 105                 110

Tyr Arg Tyr Phe Ala Ala Cys Lys Pro Asn Leu Leu Arg Leu Phe Asn
        115                 120                 125

Leu Pro His Leu Leu Leu Trp Pro Leu Met Cys Ser Ile Pro Val Thr
    130                 135                 140

Ala Trp Ala Ser Val Ser Tyr Phe Leu Tyr Pro Asp Thr Glu Tyr Thr
145                 150                 155                 160

Glu Ala Ala Val Thr Tyr Val Leu Lys Thr His Tyr Glu Val Ile Lys
                165                 170                 175

Lys Glu Asn Val Ser Tyr Ile Ala Tyr Val Tyr Gln Tyr Glu Asn
            180                 185                 190

Gly Glu Arg His Ile Tyr Ile Lys Asn Leu Leu Gly Cys Phe Val His
        195                 200                 205

Tyr Phe Val Met Ser Met Thr Phe Val Val Phe Tyr Cys Gly Phe
    210                 215                 220

Ser Thr Trp Trp Thr Ile Arg Glu His Arg Gly Ala Ser Asp Arg Thr
225                 230                 235                 240

Arg His Leu His Arg Gln Leu Phe Lys Ala Leu Val Phe Gln Thr Leu
                245                 250                 255

Val Pro Ser Ile Phe Met Tyr Ile Pro Thr Gly Val Met Phe Ile Ala
            260                 265                 270

Pro Phe Phe Asp Ile Asn Leu Asn Ala Asn Ala Asn Phe Ile Val Phe
        275                 280                 285

Cys Ser Phe Leu Tyr Pro Gly Leu Asp Pro Leu Ile Leu Ile Phe Ile
    290                 295                 300

Ile Arg Glu Phe Arg Val Thr Ile Leu Asn Ile Ile Arg Gly Asn Glu
```

```
                305                 310                 315                 320
Arg Gly Asn Ala Val Gly Glu Ala Tyr Ser Thr Ser Arg Ile Lys Ser
                    325                 330                 335

Ser Gln Pro Ala Ala Val Asn Leu Ser Gly
                340                 345

<210> SEQ ID NO 3
<211> LENGTH: 341
<212> TYPE: PRT
<213> ORGANISM: Caenorhabditis elegans

<400> SEQUENCE: 3

Met Ser Asp Arg His Trp Leu Asp Ile Thr Thr Tyr Ser Asp His Ile
1               5                   10                  15

Gly Phe Thr Ile Ser Thr Ile Ala Asn Phe Val Leu Ile Leu Leu Leu
                20                  25                  30

Val Phe Arg Pro Thr Lys Ser Tyr Gly Ser Tyr Lys Tyr Leu Met Ile
            35                  40                  45

Thr Phe Cys Val Phe Ser Leu Phe Tyr Thr Ser Ile Glu Thr Phe Leu
    50                  55                  60

Arg Pro Leu Ile His Ile Tyr Asp Asn Thr Ile Phe Val Ile Gln Arg
65                  70                  75                  80

Lys Arg Phe Gln Tyr Ser Glu Gly Thr Ala Arg Ala Ile Ser Ser Thr
                85                  90                  95

Tyr Cys Gly Cys Tyr Ala Met Ser Phe Thr Leu Phe Ala Val His Phe
            100                 105                 110

Val Tyr Arg Tyr Tyr Ala Ala Cys Lys Pro Asp Asn Leu Arg Tyr Phe
        115                 120                 125

Gln Gly Cys Tyr Phe Val Ala Trp Val Phe Gly Ala Met Ala Val Ala
    130                 135                 140

Ala Ser Trp Gly Phe Ala Ala Phe Ile Leu Tyr Pro Glu Thr Glu Arg
145                 150                 155                 160

Thr Arg Thr Ala Leu Ile His Val Ile Gln Thr Ser Tyr Glu Leu Asp
                165                 170                 175

Pro Glu Trp Val Gly Asn Val Pro Tyr Ser Tyr Trp Arg Thr Glu Asn
            180                 185                 190

Gly Val Glu Tyr Leu Asn Pro Arg Asn Val Ile Gly Ile Phe Gln His
        195                 200                 205

Gly Val Ile Met Ile Leu Ser Phe Gly Thr Val Phe Tyr Cys Gly Phe
    210                 215                 220

Asn Thr Tyr Lys Thr Leu Asn Gly Ser Leu Gly Val Ser Glu Lys Thr
225                 230                 235                 240

Lys Glu Met His Thr Gln Leu Phe Lys Ala Leu Val Leu Gln Thr Ile
                245                 250                 255

Ile Pro Thr Thr Leu Met Tyr Ile Pro Thr Thr Met Leu Phe Val Thr
            260                 265                 270

Pro Phe Val Gly Leu Asn Ile Gly Cys Tyr Gly Asn Ile Thr Thr Ala
        275                 280                 285

Thr Val His Leu Tyr Pro Gly Ile Asp Pro Val Val Leu Ile Phe Ile
    290                 295                 300

Ile Arg Asp Phe Arg Gln Thr Ile Leu Arg Pro Phe Arg Cys Phe Tyr
305                 310                 315                 320

Arg Ser Asn Ser Val Glu Asn Thr Ala Thr Ile Arg Gln Tyr Gln Gln
                325                 330                 335

Ser Ser Ser Lys Gly
```

-continued

```
                340

<210> SEQ ID NO 4
<211> LENGTH: 348
<212> TYPE: PRT
<213> ORGANISM: Caenorhabditis elegans

<400> SEQUENCE: 4

Met Ser Asp Ile Tyr Trp Ile Gln Ile Thr Glu Val Cys Ser Phe Val
1               5                   10                  15

Gly Phe Met Leu Ser Val Leu Gly Asn Ser Thr Leu Leu Val Leu Leu
            20                  25                  30

Ser Gly Lys Ser Ile Asp Gly Ile Gly Thr Tyr Arg Tyr Leu Met Ile
        35                  40                  45

Thr Phe Cys Val Phe Ser Leu Leu Phe Thr Ile Leu Glu Asp Phe Ile
    50                  55                  60

Arg Pro Leu Met His His Tyr Asn Asn Thr Ile Ile Val Leu Gln Arg
65                  70                  75                  80

Lys Arg Phe Gln Phe Ser Asp Ser Thr Ala Arg Ile Leu Thr Val Ser
                85                  90                  95

Tyr Cys Gly Cys Phe Ala Met Cys Phe Val Met Phe Ala Val His Phe
            100                 105                 110

Ile Tyr Arg Tyr Leu Val Ala Cys His Pro Thr Lys Leu His Tyr Phe
        115                 120                 125

Arg Pro Lys Asn Phe Ile Phe Trp Leu Ser Gly Met Leu Phe Ile Ala
    130                 135                 140

Gly Ser Trp Val Ala Ile Ala Tyr Val Phe Phe Gln Glu Asp Leu Glu
145                 150                 155                 160

Thr Arg Thr Asp Leu Val Phe Ile Leu Ser Thr Cys Tyr Asn Leu Thr
                165                 170                 175

Pro Asp Asp Val Gly His Val Pro Tyr Ala Phe Tyr Lys Thr Gln Gly
            180                 185                 190

Asn Thr Arg Val Ile Arg Trp Asp Asn Met Ile Gly Val Ile His His
        195                 200                 205

Met Ile Val Met Thr Ile Ser Ile Ser Ala Val Phe Tyr Phe Gly Ile
    210                 215                 220

Lys Thr Tyr Thr Arg Ile Met Ser Phe Lys Gly Lys Ser Gln Lys Thr
225                 230                 235                 240

Lys Asp Leu Gln Asn Gln Phe Phe Thr Ala Leu Val Ala Gln Thr Val
                245                 250                 255

Val Pro Leu Ile Phe Met Phe Ile Pro Asn Met Val Leu Thr Thr Ala
            260                 265                 270

Ala Leu Ile Asp Gly Thr Phe Gly Ser Trp Ala Asn Ile Thr Val Val
        275                 280                 285

Met Asn His Leu Tyr Pro Ala Ala Asp Pro Phe Val Ile Leu Phe Ile
    290                 295                 300

Ile Lys Gly Phe Arg Asn Ser Ile Arg Asn Val Ile Tyr Arg Cys Thr
305                 310                 315                 320

Lys Thr Lys Lys Ala Ser Val Ser Ser Val Val Arg Gly Ile Glu Ala
                325                 330                 335

Gln Ser Lys Gln Ser Phe Ser Arg Val Asp Ile
            340                 345

<210> SEQ ID NO 5
<211> LENGTH: 334
<212> TYPE: PRT
```

<213> ORGANISM: Caenorhabditis elegans

<400> SEQUENCE: 5

Met Thr Asp Gln His Trp Val Ile Ile Thr Asp Ile Ala Gly Pro Ile
1               5                   10                  15

Gly Phe Ser Met Ser Ile Phe Ser Asn Ser Ile Leu Leu Phe Leu Ile
                20                  25                  30

Phe Ser His Ser Ser Pro Ile Lys Gly Pro Tyr Lys Arg Met Leu Ile
            35                  40                  45

Val Phe Cys Ile Phe Thr Val Phe Tyr Ser Phe Val Glu Val Met Leu
        50                  55                  60

Gln Pro Leu Ile His Ile Tyr Asp Asp Thr Leu Phe Leu Ile His Arg
65                  70                  75                  80

Lys Arg Ile Asp Leu Pro Lys Trp Leu Thr Arg Leu Val Pro Thr Thr
                85                  90                  95

Tyr Cys Trp Cys Tyr Ala Met Ser Phe Ser Leu Phe Ala Leu Gln Phe
            100                 105                 110

Leu Tyr Arg Tyr Val Ala Val Cys Lys Pro Gln Tyr Val Asp Leu Phe
        115                 120                 125

Val Gly Cys His Phe Tyr Ala Trp Val Val Leu Ile Leu Ser Leu Ala
130                 135                 140

Thr Ser Trp Gly Leu Thr Ala Ala Phe Met Phe Pro Gln Thr Asp Arg
145                 150                 155                 160

Thr Thr Glu Ile Phe Leu His Ile Ile Tyr Ser Ser Tyr Asp Leu Glu
                165                 170                 175

Pro Tyr Trp Thr Asp Tyr Val Ala Tyr Lys Tyr Phe Asp Thr Asp Glu
            180                 185                 190

Asn Asn Val Arg Trp Val Asn Val Leu Ser Phe Gly Val Leu Gln
        195                 200                 205

His Gly Ile Val Ile Thr Leu Ser Phe Gly Thr Leu Tyr Tyr Cys Gly
210                 215                 220

Ile Asn Thr Tyr Leu Lys Ile Lys Lys His Thr Gly Thr Ser Asn Arg
225                 230                 235                 240

Thr Arg Cys Ile Gln Leu Gln Leu Phe Arg Ala Leu Val Ala Gln Thr
                245                 250                 255

Ile Leu Pro Met Phe Met Met Tyr Ile Pro Val Gly Phe Met Phe Ala
            260                 265                 270

Cys Pro Tyr Phe Asp Leu Gln Leu Gly Ala Tyr Thr Asn Tyr Gln Thr
        275                 280                 285

Val Met Ala Gln Leu Tyr Pro Gly Ile Asp Pro Phe Val Met Leu Phe
290                 295                 300

Leu Ile Asp Ser Tyr Arg Ile Thr Ile Phe Gly Trp Leu Cys Pro Arg
305                 310                 315                 320

Phe Val Tyr Val Lys Pro Met His Ser Thr Tyr Thr Leu Thr
                325                 330

<210> SEQ ID NO 6
<211> LENGTH: 350
<212> TYPE: PRT
<213> ORGANISM: Caenorhabditis elegans

<400> SEQUENCE: 6

Met Thr Asp Arg Arg Trp Val Ala Ile Thr Asp Ile Ala Gly Pro Ile
1               5                   10                  15

Gly Phe Thr Met Ser Ile Phe Ser Asn Ser Val Leu Leu Ser Leu Ile
                20                  25                  30

Phe Ser Ser Ser Ser Pro Ile Lys Gly Ala Tyr Lys Asn Met Leu Ile
            35                  40                  45

Val Leu Cys Ile Phe Thr Met Phe Tyr Ser Phe Val Glu Ile Met Leu
 50                  55                  60

Gln Pro Leu Ile His Ile Tyr Asp Asp Thr Leu Phe Leu Ile His Arg
 65                  70                  75                  80

Lys Arg Phe Asp Leu Ser Lys Gly Ile Thr Arg Leu Ile Pro Thr Thr
                    85                  90                  95

Tyr Cys Trp Cys Tyr Ala Met Ser Phe Ser Leu Phe Ala Leu Gln Phe
                100                 105                 110

Leu Tyr Arg Tyr Val Ala Val Cys Lys Pro His Leu Val Val Phe Phe
            115                 120                 125

Thr Gly Cys Tyr Phe Tyr Tyr Trp Leu Ala Leu Ile Leu Ser Leu Ala
    130                 135                 140

Thr Ser Trp Gly Leu Thr Ala Ala Phe Met Phe Pro Gln Thr Asn Arg
145                 150                 155                 160

Thr Thr Glu Ser Phe Asn Tyr Val Ile Lys Thr Ser Tyr Asp Leu Asp
                165                 170                 175

Pro Tyr Trp Thr Asp Tyr Val Ala Lys Tyr Phe Asp Thr Asp Glu
                180                 185                 190

Asn His Val Arg Trp Val Asn Val Leu Ser Leu Phe Gly Val Leu Gln
                195                 200                 205

His Gly Leu Val Ile Thr Leu Ser Phe Gly Thr Leu Phe Tyr Cys Gly
    210                 215                 220

Ile Lys Thr Tyr Leu Ser Ile Thr Glu His Val Gly Met Ser Ser Lys
225                 230                 235                 240

Thr Arg Ser Leu Gln Leu Gln Leu Phe Arg Ala Leu Val Ala Gln Thr
                245                 250                 255

Cys Leu Pro Met Leu Met Met Tyr Met Pro Ile Gly Phe Met Phe Ser
            260                 265                 270

Cys Pro Tyr Phe Asp Leu Gln Leu Gly Ala Val Thr Asn Tyr Gln Thr
            275                 280                 285

Val Met Ala Gln Leu Tyr Pro Gly Ile Asp Pro Phe Met Leu Leu Phe
    290                 295                 300

Leu Ile Asn Ala Tyr Arg Lys Thr Val Leu Ser Leu Ile Cys Pro Asn
305                 310                 315                 320

Phe Ile Gln Lys Lys Tyr Val Gln Thr Ala Thr Arg Asp Gly Thr
                325                 330                 335

Asp Ala Ser Ala Thr Met Asn Ser Val Lys Ser Thr Gln Leu
            340                 345                 350

<210> SEQ ID NO 7
<211> LENGTH: 1020
<212> TYPE: DNA
<213> ORGANISM: Caenorhabditis elegans

<400> SEQUENCE: 7
atgtcgggag aattgtggat taccctagtt gacacagcgg acattgtcgg cgtcaccctc      60
accttctgtg tcaacattgt tcttctcgga cttctgaaaa cacgtggaaa aaacttgggc     120
acttataaat atctcatggc gttttttctca gtattctcga tttttacgc catcatcgag     180 ttcatattac gacctataat gcatattgag aacaccactt tcttttttgat ctcaaggaaa     240 agattcaact actccaccaa acttggaaaa atcaactctg cgttttactg tgcttgtttt     300
gccaccagtt tgttgtctc aggagttcac tttgtttatc gatatttgc aacttgcaaa     360

-continued

| | |
|---|---|
| ccgaatctac ttcgtttgtt caacttgcca actcttctac tttggccact tggttgcagt | 420 |
| gtacccgtga caatgtgggc tagtgtctca tattttttgt atccagatac cgagtacacg | 480 |
| gaagcggctg tcaccaatgt actaaataac cactataact ggatcaaaaa ggagaatgta | 540 |
| tcgtacattg catacgtcta ttaccaatac gaaaacggag taaggcatat ctacctcaaa | 600 |
| aacttgcttg gatgctttgt tcattacttt gtcatgtcga tgacgtttgt tgtgatgttc | 660 |
| tactgcggat atgccacgtg gaaaactatg aatgaacaca aggatgtatc tgatagaact | 720 |
| cgagcgctac agaaacaact tttcaaagct ttagttcttc agacactcat cccaactatc | 780 |
| ttcatgtacg ccccaactgg agtcatgttc atcgcaccgt ttttttgacgt gaatttgaat | 840 |
| gcaaacgcca atttcattgt gttttgctca tttctgtacc cgggactcga tccactcatt | 900 |
| ctgattttga tcattcgtga tttccgaaga acaatattca atttcttgtg tggaaagaaa | 960 |
| aacagtgttg atgaatcccg ctcgacaaca agagccaatt tgtctcaagt tccgacgtga | 1020 |

<210> SEQ ID NO 8
<211> LENGTH: 1040
<212> TYPE: DNA
<213> ORGANISM: Caenorhabditis elegans

<400> SEQUENCE: 8

| | |
|---|---|
| atgtctggtc aattatggtt ggccctcgtg gatgctgccg atatggtagg attcactctc | 60 |
| acgatctcca tcaacatcat tctactgggg ctgattagaa cacgtggaaa aacgttggga | 120 |
| acgtacaaat acttgatgag cttcttctcg ttcttctcaa tcttttatgc aatcgttgaa | 180 |
| tctattttga gaccaataat gcatatcgaa aacacgacgt tctttctgat ttctcggaaa | 240 |
| cgcttcgatt actcaactcg ccttggtaaa atcaactctg cttttctactg tgcttgtttt | 300 |
| gccacgagtt ttgtcctgtc tgcggtacac tttgtgtatc ggtactttgc cgcttgcaaa | 360 |
| ccgaatctgc tacgcttgtt taaccttccg catcttttac tgtggccttt gatgtgttcg | 420 |
| attcctgtga ctgcgtgggc aagtgttttct tactttttgt acccagacac cgagtacact | 480 |
| gaagcagcag ttacatatgt tctgaaaaca cactacgagg tgatcaaaaa agaaaatgta | 540 |
| tcttatatcg catacgtata ctatcaatat gaaaatgggg agcgtcacat ctacataaaa | 600 |
| aatttgcttg gctgctttgt acactacttc gttatgtcaa tgacatttgt agttgtgttt | 660 |
| tactgcggat tttctacatg gtggacgatt cgtgagcatc gtggagcatc tgataggaca | 720 |
| cgtcacctgc atagacaatt gtttaaggca cttgtatttc aaacccttgt tccatcaata | 780 |
| tttatgtaca tcccaactgg tgtcatgttc atcgctccct ttttcgacat caacctgaat | 840 |
| gccaatgcaa acttcatcgt tttttgctca tttctctatc caggtcttga cccactaatt | 900 |
| ctcattttta tcattcgcga attcgggtca ctattttgaa tatcatcaga ggaaatgagc | 960 |
| ggggaaatgc tgttggcgaa gcatactcaa cttctcgaat aaaatcatca caacctgcag | 1020 |
| ctgttaatct ttctggataa | 1040 |

<210> SEQ ID NO 9
<211> LENGTH: 1026
<212> TYPE: DNA
<213> ORGANISM: Caenorhabditis elegans

<400> SEQUENCE: 9

| | |
|---|---|
| atgtctgacc gtcattggct cgacatcacc acctactcag accacattgg gtttacgatt | 60 |
| tccaccatcg ccaatttcgt tctgatcctt ctgctagtct tccgaccgac caaatcatac | 120 |
| ggttcataca agtacctgat gatcacattc tgcgtgttca gcctctttta cacctccatt | 180 |

```
gaaacttttt tgagacctct catccatatc tacgacaata cgatcttcgt gattcagcgc      240
aagagattcc agtactccga gggtaccgct agagccattt catcgaccta ctgcggctgc      300
tacgccatga gcttcaccct gttcgccgtc cactttgtct accgttacta tgcggcttgc      360
aaacccgaca acctccgtta cttccaagga tgctactttg tcgcatgggt attcggagca      420
atggcggtgg cggcgagctg ggggttcgca gcgtttattc tgtacccgga gaccgagagg      480
accaggacgg cgttgataca cgtcatacaa acatcctatg agctggatcc cgagtgggtg      540
ggaaatgttc catatagcta ttggcgcaca gaaaacggag tggaataccct gaatcctcgc     600 aacgtcatcg ggatctttca acacggcgtc atcatgatcc tctccttcgg aacagtcttc      660
tactgcggat tcaacactta taagactttg aacggaagtc tgggggtgtc tgaaaaaaca      720
aaagaaatgc acacccaatt gttcaaggcc ttggttctac agactatcat ccctactaca      780
ctaatgtaca tcccgacaac catgctcttt gtcaccccat cgttggact caacatcggc       840 tgttacggca acatcactac tgccaccgtc catttgtatc ctggaattga cccagtcgtt      900
ttgatcttta taatccgaga cttccggcaa acgattttaa gaccattcag atgcttctac      960
cgttcaaata tgtcgaaaaa cactgccacc ataaggcaat accagcagag cagctccaaa     1020
ggataa                                                                 1026

<210> SEQ ID NO 10
<211> LENGTH: 1047
<212> TYPE: DNA
<213> ORGANISM: Caenorhabditis elegans

<400> SEQUENCE: 10
atgtccgata tactggat acaaattact gaagtttgct ccttcgtcgg atttatgctc         60
tcagttctag ggaacagtac acttttagta ctgctcagtg gaaaatccat agatggaatt      120
ggcacctatc ggtacttgat gatcactttc tgcgttttca gtttattatt tacgatatta      180
gaggatttta tcagaccgct gatgcatcac tataacaata ccataattgt tttacaacgc      240
aagcggtttc agttttctga ttcaacggct agaatcttga cagtctctta ctgcggctgt      300
ttcgcgatgt gcttcgtgat gttcgccgtt catttcatct atcgatatct agttgcttgt      360
cacccgacaa aattgcacta ttttcgaccc aaaaatttca ttttctggct gtccggcatg      420
ttattcatag caggaagctg ggttgcaatt gcatatgtct tttttcaaga agacctagaa      480
accaggacgg atttggtatt tattttgtca acttgttata atttaacgcc agatgatgtc      540
ggacatgtac cgtatgcttt ttacaaaact caaggaaata cacgagtaat tcgatgggat      600
aacatgattg gagtaattca tcatatgata gttatgacaa tctctataag tgccgttttc      660
tactttggca ttaaaaccta cactcgaata atgagtttca agggaaaatc ccagaaaacc      720
aaggatctcc agaatcaatt tttcactgct ctagttgctc aaaccgtagt ccctctgatt      780
ttcatgttta tcccaaatat ggtgctcact acggcagccc ttatagatgg cacatttggc      840
tcatgggcca atattactgt agttatgaat catttgtatc cggctgccga tccattcgtt      900
atactgttca ttattaaggg gttccggaat agtattgaaa atgttatata tcgctgcaca      960
aaaacgaaaa aagcatcggt tagctcagtg gtccgtggta ttgaggctca aagcaagaaa     1020
caatcttttt ctcgagttga tattttaa                                        1047

<210> SEQ ID NO 11
<211> LENGTH: 1005
<212> TYPE: DNA
<213> ORGANISM: Caenorhabditis elegans
```

<400> SEQUENCE: 11

```
atgactgatc aacactgggt tattatcaca gatattgctg gtccaatcgg attttcaatg      60
tccattttt  caaactctat tcttttgttt ttgatatttt cacattcatc tccaataaaa     120
ggtccataca aacgaatgct catagtattt tgcatattta ccgtattcta ctcatttgtc     180
gaagtcatgc ttcagccact aatccatatt tacgacgaca ctttattttt gattcatcga     240
aagagaatag acttgccaaa atggttaaca cgtttggttc ctactaccta ttgttggtgt     300
tacgcaatga gttttccctt gtttgcatta caatttttat atagatatgt ggcagtatgc     360
aaaccgcaat atgttgatct ttttgtcgga tgtcactttt atgcttgggt agttttgatc     420
ttatcactag ccacgagctg gggactcact gcagctttca tgttcccaca aaccgaccga     480
acaactgaaa ttttttttgca cataatttat agttcatatg acttggagcc ttattggaca     540
gattatgttg cttataaata ctttgatact gatgagaata atgtgagatg ggtcaatgtt     600
cttagttttt tcggtgtcct tcagcacggg attgtaatta ctctaagttt tggcacccctt    660
tattattgtg gcatcaacac gtatctcaaa ataaaaaaac acactggaac atcaaacaga     720
actcgatgta ttcaactaca acttttcaga gctctggttg cacagacaat tttaccaatg     780
ttcatgatgt atattcccgt tggtttcatg tttgcatgtc catattttga cttgcaatta     840
ggtgcataca ccaattatca aacagtcatg gcacaacttt atccgggaat cgacccattt     900
gtgatgctgt ttttgataga ttcttataga ataacaatat ttggatggtt atgtccaaga     960
tttgtttatg taaagccgat gcattccaca tacaccctaa cttga                   1005
```

<210> SEQ ID NO 12
<211> LENGTH: 1053
<212> TYPE: DNA
<213> ORGANISM: Caenorhabditis elegans

<400> SEQUENCE: 12

```
atgaccgatc gtcgctgggt cgctattacg gacattgccg gaccgattgg gttcacaatg      60
tcaattttt  cgaactcggt gctgttatcg ttgatattct caagcagctc tccaattaaa     120
ggagcttaca aaatatgtt  gatagtgttg tgtatattca ctatgttcta ctctttttgtt    180
gaaataatgc ttcaaccgtt gattcatatt tatgatgaca cgctgttctt gatccaccgg     240
aaaagatttg acctgtctaa aggaattaca cgtttgatac ctacaacata ttgttggtgt     300
tatgcaatga gttctctcatt attcgccctc cagtttttgt acagatatgt ggcagtttgc     360
aaacctcact tagttgtttt tttttactgga tgctatttct attattggtt ggcactcatc     420
ttatcacttg ctacaagttg ggggcttact gcagctttta tgttcccgca aaccaatcga     480
acaactgaaa gcttcaacta cgtaataaaa acttcttatg acttagatcc ttattggacg     540
gattatgttg cctataaata ttttgacacc gatgagaatc atgtgagatg ggtgaatgtt     600
cttagtttat ttggagtctt gcagcacgga ttagtaatta cgttgagttt tggaaccttta   660
ttctactgtg gaattaaaac ttatctcagc attactgaac atgttggaat gtccagcaag     720
acccgaagtc ttcaacttca actattccgt gctttagttg ctcagacatg tcttccaatg     780
ctcatgatgt acatgccaat aggattcatg ttttcttgcc cttactttga tttgcaactt     840
ggagcagtca caaactatca aaccgtcatg gcacagttat acccaggaat cgacccattt     900
atgttgctat ttcttattaa cgcctacaga aagacagtgt taagcttgat ctgtcctaat     960
tttatccaga aaaatatgt  tcaaacggca actactcgtg atggcacaga tgcctcggca    1020
acaatgaatt ctgttaaatc tacacagtta taa                               1053
```

<210> SEQ ID NO 13
<211> LENGTH: 889
<212> TYPE: PRT
<213> ORGANISM: Artificial Sequence
<220> FEATURE:
<223> OTHER INFORMATION: BRET construct

<400> SEQUENCE: 13

```
Met Ser Gly Glu Leu Trp Ile Thr Leu Val Asp Thr Ala Asp Ile Val
1               5                   10                  15

Gly Val Thr Leu Thr Phe Cys Val Asn Ile Val Leu Leu Gly Leu Leu
            20                  25                  30

Lys Thr Arg Gly Lys Asn Leu Gly Thr Tyr Lys Tyr Leu Met Ala Phe
        35                  40                  45

Phe Ser Val Phe Ser Ile Phe Tyr Ala Ile Ile Glu Phe Ile Leu Arg
    50                  55                  60

Pro Ile Met His Ile Glu Asn Thr Thr Phe Phe Leu Ile Ser Arg Lys
65                  70                  75                  80

Arg Phe Asn Tyr Ser Thr Lys Leu Gly Lys Ile Asn Ser Ala Phe Tyr
                85                  90                  95

Cys Ala Cys Phe Ala Thr Ser Phe Val Val Ser Gly Val His Phe Val
            100                 105                 110

Tyr Arg Tyr Phe Ala Thr Cys Lys Pro Asn Leu Leu Arg Leu Phe Asn
        115                 120                 125

Leu Pro Thr Leu Leu Leu Trp Pro Leu Gly Cys Ser Val Pro Val Thr
    130                 135                 140

Met Trp Ala Ser Val Ser Tyr Phe Leu Tyr Pro Asp Thr Glu Tyr Thr
145                 150                 155                 160

Glu Ala Ala Val Thr Asn Val Leu Asn Asn His Tyr Asn Trp Ile Lys
                165                 170                 175

Lys Glu Asn Val Ser Tyr Ile Ala Tyr Val Tyr Gln Tyr Glu Asn
            180                 185                 190

Gly Val Arg His Ile Tyr Leu Lys Asn Leu Leu Gly Cys Phe Val His
        195                 200                 205

Tyr Phe Val Met Ser Met Thr Phe Val Val Met Phe Tyr Cys Gly Tyr
    210                 215                 220

Ala Thr Trp Lys Thr Met Asn Glu His Lys Asp Val Ser Asp Arg Thr
225                 230                 235                 240

Met Thr Ser Lys Val Tyr Asp Pro Glu Gln Arg Lys Arg Met Ile Thr
                245                 250                 255

Gly Pro Gln Trp Trp Ala Arg Cys Lys Gln Met Asn Val Leu Asp Ser
            260                 265                 270

Phe Ile Asn Tyr Tyr Asp Ser Glu Lys His Ala Glu Asn Ala Val Ile
        275                 280                 285

Phe Leu His Gly Asn Ala Ala Ser Ser Tyr Leu Trp Arg His Val Val
    290                 295                 300

Pro His Ile Glu Pro Val Ala Arg Cys Ile Ile Pro Asp Leu Ile Gly
305                 310                 315                 320

Met Gly Lys Ser Gly Lys Ser Gly Asn Gly Ser Tyr Arg Leu Leu Asp
                325                 330                 335

His Tyr Lys Tyr Leu Thr Ala Trp Phe Glu Leu Leu Asn Leu Pro Lys
            340                 345                 350

Lys Ile Ile Phe Val Gly His Asp Trp Gly Ala Cys Leu Ala Phe His
        355                 360                 365
```

```
Tyr Ser Tyr Glu His Gln Asp Lys Ile Lys Ala Ile Val His Ala Glu
370                 375                 380

Ser Val Val Asp Val Ile Glu Ser Trp Asp Glu Trp Pro Asp Ile Glu
385                 390                 395                 400

Glu Asp Ile Ala Leu Ile Lys Ser Glu Glu Gly Glu Lys Met Val Leu
                405                 410                 415

Glu Asn Asn Phe Phe Val Glu Thr Met Leu Pro Ser Lys Ile Met Arg
                420                 425                 430

Lys Leu Glu Pro Glu Glu Phe Ala Ala Tyr Leu Glu Pro Phe Lys Glu
            435                 440                 445

Lys Gly Glu Val Arg Arg Pro Thr Leu Ser Trp Pro Arg Glu Ile Pro
450                 455                 460

Leu Val Lys Gly Gly Lys Pro Asp Val Val Gln Ile Val Arg Asn Tyr
465                 470                 475                 480

Asn Ala Tyr Leu Arg Ala Ser Asp Asp Leu Pro Lys Met Phe Ile Glu
                485                 490                 495

Ser Asp Pro Gly Phe Phe Ser Asn Ala Ile Val Glu Gly Ala Lys Lys
            500                 505                 510

Phe Pro Asn Thr Glu Phe Val Lys Val Lys Gly Leu His Phe Ser Gln
        515                 520                 525

Glu Asp Ala Pro Asp Glu Met Gly Lys Tyr Ile Lys Ser Phe Val Glu
530                 535                 540

Arg Val Leu Lys Asn Glu Gln Arg Ala Leu Gln Lys Gln Leu Phe Lys
545                 550                 555                 560

Ala Leu Val Leu Gln Thr Leu Ile Pro Thr Ile Phe Met Tyr Ala Pro
                565                 570                 575

Thr Gly Val Met Phe Ile Ala Pro Phe Phe Asp Val Asn Leu Asn Ala
            580                 585                 590

Asn Ala Asn Phe Ile Val Phe Cys Ser Phe Leu Tyr Pro Gly Leu Asp
        595                 600                 605

Pro Leu Ile Leu Ile Leu Ile Ile Arg Asp Phe Arg Arg Thr Ile Phe
610                 615                 620

Asn Phe Leu Cys Gly Lys Lys Asn Ser Val Asp Glu Ser Arg Ser Thr
625                 630                 635                 640

Thr Arg Ala Asn Leu Ser Gln Val Pro Thr Met Val Ser Lys Gly Glu
                645                 650                 655

Glu Leu Phe Thr Gly Val Val Pro Ile Leu Val Glu Leu Asp Gly Asp
            660                 665                 670

Val Asn Gly His Lys Phe Ser Val Ser Gly Glu Gly Gly Asp Ala
        675                 680                 685

Thr Tyr Gly Lys Leu Thr Leu Lys Phe Ile Cys Thr Thr Gly Lys Leu
690                 695                 700

Pro Val Pro Trp Pro Thr Leu Val Thr Thr Leu Ser Tyr Gly Val Gln
705                 710                 715                 720

Cys Phe Ser Arg Tyr Pro Asp His Met Lys Gln His Asp Phe Phe Lys
                725                 730                 735

Ser Ala Met Pro Glu Gly Tyr Val Gln Glu Arg Thr Ile Phe Phe Lys
            740                 745                 750

Asp Asp Gly Asn Tyr Lys Thr Arg Ala Glu Val Lys Phe Glu Gly Asp
        755                 760                 765

Thr Leu Val Asn Arg Ile Glu Leu Lys Gly Ile Asp Phe Lys Glu Asp
770                 775                 780

Gly Asn Ile Leu Gly His Lys Leu Glu Tyr Asn Tyr Asn Ser His Asn
785                 790                 795                 800
```

```
Val Tyr Ile Met Ala Asp Lys Gln Lys Asn Gly Ile Lys Val Asn Phe
                805                 810                 815

Lys Ile Arg His Asn Ile Glu Asp Gly Ser Val Gln Leu Ala Asp His
            820                 825                 830

Tyr Gln Gln Asn Thr Pro Ile Gly Asp Gly Pro Val Leu Leu Pro Asp
        835                 840                 845

Asn His Tyr Leu Ser Thr Gln Ser Ala Leu Ser Lys Asp Pro Asn Glu
    850                 855                 860

Lys Arg Asp His Met Val Leu Leu Glu Phe Val Thr Ala Ala Gly Ile
865                 870                 875                 880

Thr Leu Gly Met Asp Glu Leu Tyr Lys
                885

<210> SEQ ID NO 14
<211> LENGTH: 2670
<212> TYPE: DNA
<213> ORGANISM: Artificial Sequence
<220> FEATURE:
<223> OTHER INFORMATION: ORF encoding BRET construct of SEQ ID NO:13

<400> SEQUENCE: 14
atgtcgggag aattgtggat tacccctagtt gacacagcgg acattgtcgg cgtcaccctc      60
accttctgtg tcaacattgt tcttctcgga cttctgaaaa cacgtggaaa aaacttgggc     120
acttataaat atctcatggc gttttttctca gtattctcga ttttttacgc catcatcgag     180
ttcatattac gacctataat gcatattgag aacaccactt tcttttttgat ctcaaggaaa     240
agattcaact actccaccaa acttggaaaa atcaactctg cgttttactg tgcttgtttt     300
gccaccagtt tgttgtctc aggagttcac tttgtttatc gatattttgc aacttgcaaa     360
ccgaatctac ttcgtttgtt caacttgcca actcttctac tttggccact tggttgcagt     420
gtacccgtga caatgtgggc tagtgtctca tattttttgt atccagatac cgagtacacg     480
gaagcggctg tcaccaatgt actaaataac cactataact ggatcaaaaa ggagaatgta     540
tcgtacattg catacgtcta ttaccaatac gaaaacggag taaggcatat ctacctcaaa     600
aacttgcttg gatgctttgt tcattacttt gtcatgtcga tgacgtttgt tgtgatgttc     660
tactgcggat atgccacgtg gaaaactatg aatgaacaca aggatgtatc tgatagaact     720
atgaccagca aggtgtacga ccccgagcag aggaagagga tgatcaccgg ccccccagtgg     780
tgggccaggt gcaagcagat gaacgtgctg gacagcttca tcaactacta cgacagcgag     840
aagcacgccg agaacgccgt gatcttcctg cacggcaacg ccgctagcag ctacctgtgg     900
aggcacgtgg tgccccacat cgagcccgtg gccaggtgca tcatcccga tctgatcggc     960
atgggcaaga gcggcaagag cggcaacggc agctacaggc tgctggacca ctacaagtac    1020
ctgaccgcct ggttcgagct cctgaacctg cccaagaaga tcatcttcgt gggccacgac    1080
tggggcgcct gcctggcctt ccactacagc tacgagcacc aggacaagat caaggccatc    1140
gtgcacgccg agagcgtggt ggacgtgatc gagagctggg acgagtggcc agacatcgag    1200
gaggacatcg ccctgatcaa gagcgaggag ggcgagaaga tggtgctgga gaacaacttc    1260
ttcgtggaga ccatgctgcc cagcaagatc atgagaaagc tggagcccga ggagttcgcc    1320
gcctacctgg agcccttcaa ggagaagggc gaggtgagaa gacccaccct gagctggccc    1380
agagagatcc ccctggtgaa gggcggcaag cccgacgtgg tgcagatcgt gagaaactac    1440
aacgcctacc tgagagccag cgacgacctg cccaagatgt tcatcgagag cgaccccggc    1500
ttcttcagca acgccatcgt ggagggcgcc aagaagttcc ccaacaccga gttcgtgaag    1560
```

```
gtgaagggcc tgcacttcag ccaggaggac gcccccgacg agatgggcaa gtacatcaag    1620
agcttcgtgg agagagtgct gaagaacgag cagcgagcgc tacagaaaca acttttcaaa    1680
gctttagttc ttcagacact catcccaact atcttcatgt acgccccaac tggagtcatg    1740
ttcatcgcac cgttttttga cgtgaatttg aatgcaaacg ccaatttcat tgtgttttgc    1800
tcatttctgt acccgggact cgatccactc attctgattt tgatcattcg tgatttccga    1860
agaacaatat tcaatttctt gtgtggaaag aaaaacagtg ttgatgaatc ccgctcgaca    1920
acaagagcca atttgtctca agttccgacg atggtgagca agggcgagga gctgttcacc    1980
ggggtggtgc ccatcctggt cgagctggac ggcgacgtaa acggccacaa gttcagcgtg    2040
tccggcgagg gcgagggcga tgccacctac ggcaagctga ccctgaagtt catctgcacc    2100
accggcaagc tgcccgtgcc ctggcccacc ctcgtgacca ccctgagcta cggcgtgcag    2160
tgcttcagcc gctaccccga ccacatgaag cagcacgact tcttcaagtc cgccatgccc    2220
gaaggctacg tccaggagcg caccatcttc ttcaaggacg acggcaacta caagacccgc    2280
gccgaggtga agttcgaggg cgacaccctg gtgaaccgca tcgagctgaa gggcatcgac    2340
ttcaaggagg acggcaacat cctggggcac aagctggagt acaactacaa cagccacaac    2400
gtctatatca tggccgacaa gcagaagaac ggcatcaagg tgaacttcaa gatccgccac    2460
aacatcgagg acggcagcgt gcagctcgcc gaccactacc agcagaacac ccccatcggc    2520
gacggccccg tgctgctgcc cgacaaccac tacctgagca cccagtccgc cctgagcaaa    2580
gaccccaacg agaagcgcga tcacatggtc ctgctggagt tcgtgaccgc cgccgggatc    2640
actctcggca tggacgagct gtacaagtaa                                      2670
```

<210> SEQ ID NO 15
<211> LENGTH: 889
<212> TYPE: PRT
<213> ORGANISM: Artificial Sequence
<220> FEATURE:
<223> OTHER INFORMATION: BRET construct

<400> SEQUENCE: 15

```
Met Ser Gly Glu Leu Trp Ile Thr Leu Val Asp Thr Ala Asp Ile Val
1               5                   10                  15

Gly Val Thr Leu Thr Phe Cys Val Asn Ile Val Leu Leu Gly Leu Leu
            20                  25                  30

Lys Thr Arg Gly Lys Asn Leu Gly Thr Tyr Lys Tyr Leu Met Ala Phe
        35                  40                  45

Phe Ser Val Phe Ser Ile Phe Tyr Ala Ile Ile Glu Phe Ile Leu Arg
    50                  55                  60

Pro Ile Met His Ile Glu Asn Thr Thr Phe Phe Leu Ile Ser Arg Lys
65                  70                  75                  80

Arg Phe Asn Tyr Ser Thr Lys Leu Gly Lys Ile Asn Ser Ala Phe Tyr
                85                  90                  95

Cys Ala Cys Phe Ala Thr Ser Phe Val Val Ser Gly Val His Phe Val
            100                 105                 110

Tyr Arg Tyr Phe Ala Thr Cys Lys Pro Asn Leu Leu Arg Leu Phe Asn
        115                 120                 125

Leu Pro Thr Leu Leu Leu Trp Pro Leu Gly Cys Ser Val Pro Val Thr
    130                 135                 140

Met Trp Ala Ser Val Ser Tyr Phe Leu Tyr Pro Asp Thr Glu Tyr Thr
145                 150                 155                 160

Glu Ala Ala Val Thr Asn Val Leu Asn Asn His Tyr Asn Trp Ile Lys
```

```
                        165                 170                 175
Lys Glu Asn Val Ser Tyr Ile Ala Tyr Val Tyr Tyr Gln Tyr Glu Asn
                180                 185                 190

Gly Val Arg His Ile Tyr Leu Lys Asn Leu Leu Gly Cys Phe Val His
            195                 200                 205

Tyr Phe Val Met Ser Met Thr Phe Val Met Phe Tyr Cys Gly Tyr
        210                 215                 220

Ala Thr Trp Lys Thr Met Asn Glu His Lys Asp Val Ser Asp Arg Thr
225                 230                 235                 240

Met Val Ser Lys Gly Glu Glu Leu Phe Thr Gly Val Val Pro Ile Leu
                245                 250                 255

Val Glu Leu Asp Gly Asp Val Asn Gly His Lys Phe Ser Val Ser Gly
            260                 265                 270

Glu Gly Glu Gly Asp Ala Thr Tyr Gly Lys Leu Thr Leu Lys Phe Ile
        275                 280                 285

Cys Thr Thr Gly Lys Leu Pro Val Pro Trp Pro Thr Leu Val Thr Thr
290                 295                 300

Leu Ser Tyr Gly Val Gln Cys Phe Ser Arg Tyr Pro Asp His Met Lys
305                 310                 315                 320

Gln His Asp Phe Phe Lys Ser Ala Met Pro Glu Gly Tyr Val Gln Glu
                325                 330                 335

Arg Thr Ile Phe Phe Lys Asp Asp Gly Asn Tyr Lys Thr Arg Ala Glu
            340                 345                 350

Val Lys Phe Glu Gly Asp Thr Leu Val Asn Arg Ile Glu Leu Lys Gly
        355                 360                 365

Ile Asp Phe Lys Glu Asp Gly Asn Ile Leu Gly His Lys Leu Glu Tyr
370                 375                 380

Asn Tyr Asn Ser His Asn Val Tyr Ile Met Ala Asp Lys Gln Lys Asn
385                 390                 395                 400

Gly Ile Lys Val Asn Phe Lys Ile Arg His Asn Ile Glu Asp Gly Ser
                405                 410                 415

Val Gln Leu Ala Asp His Tyr Gln Gln Asn Thr Pro Ile Gly Asp Gly
            420                 425                 430

Pro Val Leu Leu Pro Asp Asn His Tyr Leu Ser Thr Gln Ser Ala Leu
        435                 440                 445

Ser Lys Asp Pro Asn Glu Lys Arg Asp His Met Val Leu Leu Glu Phe
450                 455                 460

Val Thr Ala Ala Gly Ile Thr Leu Gly Met Asp Glu Leu Tyr Lys Arg
465                 470                 475                 480

Ala Leu Gln Lys Gln Leu Phe Lys Ala Leu Val Leu Gln Thr Leu Ile
                485                 490                 495

Pro Thr Ile Phe Met Tyr Ala Pro Thr Gly Val Met Phe Ile Ala Pro
            500                 505                 510

Phe Phe Asp Val Asn Leu Asn Ala Asn Ala Asn Phe Ile Val Phe Cys
        515                 520                 525

Ser Phe Leu Tyr Pro Gly Leu Asp Pro Leu Ile Leu Ile Leu Ile Ile
530                 535                 540

Arg Asp Phe Arg Arg Thr Ile Phe Asn Phe Leu Cys Gly Lys Lys Asn
545                 550                 555                 560

Ser Val Asp Glu Ser Arg Ser Thr Thr Arg Ala Asn Leu Ser Gln Val
                565                 570                 575

Pro Thr Met Thr Ser Lys Val Tyr Asp Pro Glu Gln Arg Lys Arg Met
            580                 585                 590
```

```
Ile Thr Gly Pro Gln Trp Trp Ala Arg Cys Lys Gln Met Asn Val Leu
            595                 600                 605
Asp Ser Phe Ile Asn Tyr Tyr Asp Ser Glu Lys His Ala Glu Asn Ala
610                 615                 620
Val Ile Phe Leu His Gly Asn Ala Ala Ser Ser Tyr Leu Trp Arg His
625                 630                 635                 640
Val Val Pro His Ile Glu Pro Val Ala Arg Cys Ile Ile Pro Asp Leu
                645                 650                 655
Ile Gly Met Gly Lys Ser Gly Lys Ser Gly Asn Gly Ser Tyr Arg Leu
            660                 665                 670
Leu Asp His Tyr Lys Tyr Leu Thr Ala Trp Phe Glu Leu Leu Asn Leu
        675                 680                 685
Pro Lys Lys Ile Ile Phe Val Gly His Asp Trp Gly Ala Cys Leu Ala
690                 695                 700
Phe His Tyr Ser Tyr Glu His Gln Asp Lys Ile Lys Ala Ile Val His
705                 710                 715                 720
Ala Glu Ser Val Val Asp Val Ile Glu Ser Trp Asp Glu Trp Pro Asp
                725                 730                 735
Ile Glu Glu Asp Ile Ala Leu Ile Lys Ser Glu Gly Glu Lys Met
            740                 745                 750
Val Leu Glu Asn Asn Phe Phe Val Glu Thr Met Leu Pro Ser Lys Ile
        755                 760                 765
Met Arg Lys Leu Glu Pro Glu Glu Phe Ala Ala Tyr Leu Glu Pro Phe
770                 775                 780
Lys Glu Lys Gly Glu Val Arg Arg Pro Thr Leu Ser Trp Pro Arg Glu
785                 790                 795                 800
Ile Pro Leu Val Lys Gly Gly Lys Pro Asp Val Val Gln Ile Val Arg
                805                 810                 815
Asn Tyr Asn Ala Tyr Leu Arg Ala Ser Asp Asp Leu Pro Lys Met Phe
            820                 825                 830
Ile Glu Ser Asp Pro Gly Phe Phe Ser Asn Ala Ile Val Glu Gly Ala
        835                 840                 845
Lys Lys Phe Pro Asn Thr Glu Phe Val Lys Val Lys Gly Leu His Phe
850                 855                 860
Ser Gln Glu Asp Ala Pro Asp Glu Met Gly Lys Tyr Ile Lys Ser Phe
865                 870                 875                 880
Val Glu Arg Val Leu Lys Asn Glu Gln
                885

<210> SEQ ID NO 16
<211> LENGTH: 2670
<212> TYPE: DNA
<213> ORGANISM: Artificial Sequence
<220> FEATURE:
<223> OTHER INFORMATION: ORF encoding BRET construct of SEQ ID NO:15

<400> SEQUENCE: 16 atgtcggag aattgtggat taccctagtt gacacagcgg acattgtcgg cgtcaccctc      60
accttctgtg tcaacattgt tcttctcgga cttctgaaaa cacgtggaaa aaacttgggc     120
acttataaat atctcatggc gttttttctca gtattctcga tttttttacgc catcatcgag     180 ttcatattac gacctataat gcatattgag aacaccactt tcttttttgat ctcaaggaaa    240 agattcaact actccaccaa acttggaaaa atcaactctg cgtttttactg tgcttgtttt    300 gccaccagtt tgttgtctc aggagttcac tttgtttatc gatatttttgc aacttgcaaa    360 ccgaatctac ttcgtttgtt caacttgcca actcttctac tttggccact tggttgcagt    420
```

```
gtacccgtga caatgtgggc tagtgtctca tattttttgt atccagatac cgagtacacg    480
gaagcggctg tcaccaatgt actaaataac cactataact ggatcaaaaa ggagaatgta    540
tcgtacattg catacgtcta ttaccaatac gaaaacggag taaggcatat ctacctcaaa    600
aacttgcttg gatgctttgt tcattacttt gtcatgtcga tgacgtttgt tgtgatgttc    660
tactgcggat atgccacgtg gaaaactatg aatgaacaca aggatgtatc tgatagaact    720
atggtgagca agggcgagga gctgttcacc ggggtggtgc ccatcctggt cgagctggac    780
ggcgacgtaa acggccacaa gttcagcgtg tccggcgagg gcgagggcga tgccacctac    840
ggcaagctga ccctgaagtt catctgcacc accggcaagc tgcccgtgcc ctggcccacc    900
ctcgtgacca ccctgagcta cggcgtgcag tgcttcagcc gctaccccga ccacatgaag    960
cagcacgact tcttcaagtc cgccatgccc gaaggctacg tccaggagcg caccatcttc   1020
ttcaaggacg acggcaacta caagacccgc gccgaggtga agttcgaggg cgacaccctg   1080
gtgaaccgca tcgagctgaa gggcatcgac ttcaaggagg acggcaacat cctggggcac   1140
aagctggagt acaactacaa cagccacaac gtctatatca tggccgacaa gcagaagaac   1200
ggcatcaagg tgaacttcaa gatccgccac aacatcgagg acggcagcgt gcagctcgcc   1260
gaccactacc agcagaacac ccccatcggc gacggccccg tgctgctgcc cgacaaccac   1320
tacctgagca cccagtccgc cctgagcaaa gaccccaacg agaagcgcga tcacatggtc   1380
ctgctggagt tcgtgaccgc cgccgggatc actctcggca tggacgagct gtacaagcga   1440
gcgctacaga aacaactttt caaagcttta gttcttcaga cactcatccc aactatcttc   1500
atgtacgccc aactggagt catgttcatc gcaccgtttt ttgacgtgaa tttgaatgca   1560
aacgccaatt tcattgtgtt ttgctcattt ctgtacccgg gactcgatcc actcattctg   1620
attttgatca ttcgtgattt ccgaagaaca atattcaatt tcttgtgtgg aaagaaaaac   1680
agtgttgatg aatcccgctc gacaacaaga gccaatttgt ctcaagttcc gacgatgacc   1740
agcaaggtgt acgaccccga gcagaggaag aggatgatca ccggcccca gtggtgggcc    1800 aggtgcaagc agatgaacgt gctggacagc ttcatcaact actacgacag cgagaagcac   1860
gccgagaacg ccgtgatctt cctgcacggc aacgccgcta gcagctacct gtggaggcac   1920
gtggtgcccc acatcgagcc cgtggccagg tgcatcatcc ccgatctgat cggcatgggc   1980
aagagcggca agagcggcaa cggcagctac aggctgctgg accactacaa gtacctgacc   2040
gcctggttcg agctcctgaa cctgcccaag aagatcatct tcgtgggcca cgactggggc   2100
gcctgcctgg ccttccacta cagctacgag caccaggaca agatcaaggc catcgtgcac   2160
gccgagagcg tggtggacgt gatcgagagc tgggacgagt ggccagacat cgaggaggac   2220
atcgccctga tcaagagcga ggagggcgag aagatggtgc tggagaacaa cttcttcgtg   2280
gagaccatgc tgcccagcaa gatcatgaga aagctggagc ccgaggagtt cgccgcctac   2340
ctggagccct tcaaggagaa gggcgaggtg agaagaccca ccctgagctg gcccagagag   2400
atccccctgg tgaagggcgg caagcccgac gtggtgcaga tcgtgagaaa ctacaacgcc   2460
tacctgagag ccagcgacga cctgcccaag atgttcatcg agagcgaccc cggcttcttc   2520
agcaacgcca tcgtggaggg cgccaagaag ttccccaaca ccgagttcgt gaaggtgaag   2580
ggcctgcact tcagccagga ggacgccccc gacgagatgg gcaagtacat caagagcttc   2640
gtggagagag tgctgaagaa cgagcagtaa                                    2670
```

<210> SEQ ID NO 17
<211> LENGTH: 650

```
<212> TYPE: PRT
<213> ORGANISM: Artificial Sequence
<220> FEATURE:
<223> OTHER INFORMATION: BRET construct

<400> SEQUENCE: 17

Met Ser Gly Glu Leu Trp Ile Thr Leu Val Asp Thr Ala Asp Ile Val
1               5                   10                  15

Gly Val Thr Leu Thr Phe Cys Val Asn Ile Val Leu Leu Gly Leu Leu
            20                  25                  30

Lys Thr Arg Gly Lys Asn Leu Gly Thr Tyr Lys Tyr Leu Met Ala Phe
        35                  40                  45

Phe Ser Val Phe Ser Ile Phe Tyr Ala Ile Ile Glu Phe Ile Leu Arg
    50                  55                  60

Pro Ile Met His Ile Glu Asn Thr Thr Phe Phe Leu Ile Ser Arg Lys
65                  70                  75                  80

Arg Phe Asn Tyr Ser Thr Lys Leu Gly Lys Ile Asn Ser Ala Phe Tyr
                85                  90                  95

Cys Ala Cys Phe Ala Thr Ser Phe Val Val Ser Gly Val His Phe Val
            100                 105                 110

Tyr Arg Tyr Phe Ala Thr Cys Lys Pro Asn Leu Leu Arg Leu Phe Asn
        115                 120                 125

Leu Pro Thr Leu Leu Leu Trp Pro Leu Gly Cys Ser Val Pro Val Thr
    130                 135                 140

Met Trp Ala Ser Val Ser Tyr Phe Leu Tyr Pro Asp Thr Glu Tyr Thr
145                 150                 155                 160

Glu Ala Ala Val Thr Asn Val Leu Asn Asn His Tyr Asn Trp Ile Lys
                165                 170                 175

Lys Glu Asn Val Ser Tyr Ile Ala Tyr Val Tyr Tyr Gln Tyr Glu Asn
            180                 185                 190

Gly Val Arg His Ile Tyr Leu Lys Asn Leu Leu Gly Cys Phe Val His
        195                 200                 205

Tyr Phe Val Met Ser Met Thr Phe Val Val Met Phe Tyr Cys Gly Tyr
    210                 215                 220

Ala Thr Trp Lys Thr Met Asn Glu His Lys Asp Val Ser Asp Arg Thr
225                 230                 235                 240

Arg Ala Leu Gln Lys Gln Leu Phe Lys Ala Leu Val Leu Gln Thr Leu
                245                 250                 255

Ile Pro Thr Ile Phe Met Tyr Ala Pro Thr Gly Val Met Phe Ile Ala
            260                 265                 270

Pro Phe Phe Asp Val Asn Leu Asn Ala Asn Ala Asn Phe Ile Val Phe
        275                 280                 285

Cys Ser Phe Leu Tyr Pro Gly Leu Asp Pro Leu Ile Leu Ile Leu Ile
    290                 295                 300

Ile Arg Asp Phe Arg Arg Thr Ile Phe Asn Phe Leu Cys Gly Lys Lys
305                 310                 315                 320

Asn Ser Val Asp Glu Ser Arg Ser Thr Thr Arg Ala Asn Leu Ser Gln
                325                 330                 335

Val Pro Thr Met Thr Ser Lys Val Tyr Asp Pro Glu Gln Arg Lys Arg
            340                 345                 350

Met Ile Thr Gly Pro Gln Trp Trp Ala Arg Cys Lys Gln Met Asn Val
        355                 360                 365

Leu Asp Ser Phe Ile Asn Tyr Tyr Asp Ser Glu Lys His Ala Glu Asn
    370                 375                 380

Ala Val Ile Phe Leu His Gly Asn Ala Ala Ser Ser Tyr Leu Trp Arg
```

His Val Val Pro His Ile Glu Pro Val Ala Arg Cys Ile Ile Pro Asp
385                 390                 395                 400

Leu Ile Gly Met Gly Lys Ser Gly Lys Ser Gly Asn Gly Ser Tyr Arg
            405                 410                 415

Leu Leu Asp His Tyr Lys Tyr Leu Thr Ala Trp Phe Glu Leu Leu Asn
            420                 425                 430

Leu Pro Lys Lys Ile Ile Phe Val Gly His Asp Trp Gly Ala Cys Leu
        435                 440                 445

Ala Phe His Tyr Ser Tyr Glu His Gln Asp Lys Ile Lys Ala Ile Val
450             455                 460

His Ala Glu Ser Val Val Asp Val Ile Glu Ser Trp Asp Glu Trp Pro
465             470                 475                 480

Asp Ile Glu Glu Asp Ile Ala Leu Ile Lys Ser Glu Glu Gly Glu Lys
                485                 490                 495

Met Val Leu Glu Asn Asn Phe Phe Val Glu Thr Met Leu Pro Ser Lys
            500                 505                 510

Ile Met Arg Lys Leu Glu Pro Glu Glu Phe Ala Ala Tyr Leu Glu Pro
        515                 520                 525

Phe Lys Glu Lys Gly Glu Val Arg Arg Pro Thr Leu Ser Trp Pro Arg
545             530                 535                 540

Glu Ile Pro Leu Val Lys Gly Gly Lys Pro Asp Val Val Gln Ile Val
                545                 550                 560

Arg Asn Tyr Asn Ala Tyr Leu Arg Ala Ser Asp Asp Leu Pro Lys Met
            565                 570                 575

Phe Ile Glu Ser Asp Pro Gly Phe Phe Ser Asn Ala Ile Val Glu Gly
        580                 585                 590

Ala Lys Lys Phe Pro Asn Thr Glu Phe Val Lys Val Lys Gly Leu His
            595                 600                 605

Phe Ser Gln Glu Asp Ala Pro Asp Glu Met Gly Lys Tyr Ile Lys Ser
610             615                 620

Phe Val Glu Arg Val Leu Lys Asn Glu Gln
                625                 630                     640

645                 650

<210> SEQ ID NO 18
<211> LENGTH: 1953
<212> TYPE: DNA
<213> ORGANISM: Artificial Sequence
<220> FEATURE:
<223> OTHER INFORMATION: ORF encoding BRET construct of SEQ ID NO:17

<400> SEQUENCE: 18
atgtcgggag aattgtggat taccctagtt gacacagcgg acattgtcgg cgtcaccctc     60
accttctgtg tcaacattgt tcttctcgga cttctgaaaa cacgtggaaa aaacttgggc    120
acttataaat atctcatggc gtttttctca gtattctcga tttttacgc catcatcgag    180 ttcatattac gacctataat gcatattgag aacaccactt tcttttttgat ctcaaggaaa    240 agattcaact actccaccaa acttggaaaa atcaactctg cgttttactg tgcttgtttt    300
gccaccagtt tgttgtctc aggagttcac tttgtttatc gatattttgc aacttgcaaa    360
ccgaatctac ttcgtttgtt caacttgcca actcttctac tttggccact tggttgcagt    420
gtacccgtga caatgtgggc tagtgtctca tattttttgt atccagatac cgagtacacg    480
gaagcggctg tcaccaatgt actaaataac cactataact ggatcaaaaa ggagaatgta    540
tcgtacattg catacgtcta ttaccaatac gaaaacggag taaggcatat ctaccctcaaa    600

```
aacttgcttg gatgctttgt tcattacttt gtcatgtcga tgacgtttgt tgtgatgttc    660
tactgcggat atgccacgtg gaaaactatg aatgaacaca aggatgtatc tgatagaact    720
cgagcgctac agaaacaact tttcaaagct ttagttcttc agacactcat cccaactatc    780
ttcatgtacg ccccaactgg agtcatgttc atcgcaccgt tttttgacgt gaatttgaat    840
gcaaacgcca atttcattgt gttttgctca tttctgtacc cgggactcga tccactcatt    900
ctgattttga tcattcgtga tttccgaaga acaatattca atttcttgtg tggaaagaaa    960
aacagtgttg atgaatcccg ctcgacaaca agagccaatt tgtctcaagt tccgacgatg   1020
accagcaagg tgtacgaccc cgagcagagg aagaggatga tcaccggccc cagtggtgg    1080 gccaggtgca agcagatgaa cgtgctggac agcttcatca actactacga cagcgagaag   1140
cacgccgaga acgccgtgat cttcctgcac ggcaacgccg ctagcagcta cctgtgtgagg  1200 cacgtggtgc cccacatcga gcccgtggcc aggtgcatca tccccgatct gatcggcatg   1260
ggcaagagcg gcaagagcgg caacggcagc tacaggctgc tggaccacta caagtacctg   1320
accgcctggt tcgagctcct gaacctgccc aagaagatca tcttcgtggg ccacgactgg   1380
ggcgcctgcc tggccttcca ctacagctac gagcaccagg acaagatcaa ggccatcgtg   1440
cacgccgaga gcgtggtgga cgtgatcgag agctgggacg agtggccaga catcgaggag   1500
gacatcgccc tgatcaagag cgaggagggc gagaagatgg tgctggagaa caacttcttc   1560
gtggagacca tgctgcccag caagatcatg agaaagctgg agcccgagga gttcgccgcc   1620
tacctggagc ccttcaagga agagggcgag gtgagaagac ccacccctgag ctggcccaga   1680 gagatccccc tggtgaaggg cggcaagccc gacgtggtgc agatcgtgag aaaactacaac   1740 gcctacctga gagccagcga cgacctgccc aagatgttca tcgagagcga ccccggcttc   1800
ttcagcaacg ccatcgtgga gggcgccaag aagttcccca caccgagtt cgtgaaggtg    1860 aagggcctgc acttcagcca ggaggacgcc cccgacgaga tgggcaagta catcaagagc   1920
ttcgtggaga gagtgctgaa gaacgagcag taa                                1953
```

<210> SEQ ID NO 19
<211> LENGTH: 578
<212> TYPE: PRT
<213> ORGANISM: Artificial Sequence
<220> FEATURE:
<223> OTHER INFORMATION: BRET construct

<400> SEQUENCE: 19

```
Met Ser Gly Glu Leu Trp Ile Thr Leu Val Asp Thr Ala Asp Ile Val
1               5                  10                  15

Gly Val Thr Leu Thr Phe Cys Val Asn Ile Val Leu Leu Gly Leu Leu
            20                  25                  30

Lys Thr Arg Gly Lys Asn Leu Gly Thr Tyr Lys Tyr Leu Met Ala Phe
        35                  40                  45

Phe Ser Val Phe Ser Ile Phe Tyr Ala Ile Ile Glu Phe Ile Leu Arg
    50                  55                  60

Pro Ile Met His Ile Glu Asn Thr Thr Phe Phe Leu Ile Ser Arg Lys
65                  70                  75                  80

Arg Phe Asn Tyr Ser Thr Lys Leu Gly Lys Ile Asn Ser Ala Phe Tyr
                85                  90                  95

Cys Ala Cys Phe Ala Thr Ser Phe Val Val Ser Gly Val His Phe Val
            100                 105                 110

Tyr Arg Tyr Phe Ala Thr Cys Lys Pro Asn Leu Leu Arg Leu Phe Asn
        115                 120                 125
```

-continued

Leu Pro Thr Leu Leu Leu Trp Pro Leu Gly Cys Ser Val Pro Val Thr
130                 135                 140

Met Trp Ala Ser Val Ser Tyr Phe Leu Tyr Pro Asp Thr Glu Tyr Thr
145                 150                 155                 160

Glu Ala Ala Val Thr Asn Val Leu Asn Asn His Tyr Asn Trp Ile Lys
                165                 170                 175

Lys Glu Asn Val Ser Tyr Ile Ala Tyr Val Tyr Gln Tyr Glu Asn
            180                 185                 190

Gly Val Arg His Ile Tyr Leu Lys Asn Leu Leu Gly Cys Phe Val His
        195                 200                 205

Tyr Phe Val Met Ser Met Thr Phe Val Val Met Phe Tyr Cys Gly Tyr
210                 215                 220

Ala Thr Trp Lys Thr Met Asn Glu His Lys Asp Val Ser Asp Arg Thr
225                 230                 235                 240

Arg Ala Leu Gln Lys Gln Leu Phe Lys Ala Leu Val Leu Gln Thr Leu
                245                 250                 255

Ile Pro Thr Ile Phe Met Tyr Ala Pro Thr Gly Val Met Phe Ile Ala
            260                 265                 270

Pro Phe Phe Asp Val Asn Leu Asn Ala Asn Ala Asn Phe Ile Val Phe
        275                 280                 285

Cys Ser Phe Leu Tyr Pro Gly Leu Asp Pro Leu Ile Leu Ile Leu Ile
290                 295                 300

Ile Arg Asp Phe Arg Arg Thr Ile Phe Asn Phe Leu Cys Gly Lys Lys
305                 310                 315                 320

Asn Ser Val Asp Glu Ser Arg Ser Thr Thr Arg Ala Asn Leu Ser Gln
                325                 330                 335

Val Pro Thr Met Val Ser Lys Gly Glu Glu Leu Phe Thr Gly Val Val
            340                 345                 350

Pro Ile Leu Val Glu Leu Asp Gly Asp Val Asn Gly His Lys Phe Ser
        355                 360                 365

Val Ser Gly Glu Gly Glu Gly Asp Ala Thr Tyr Gly Lys Leu Thr Leu
370                 375                 380

Lys Phe Ile Cys Thr Thr Gly Lys Leu Pro Val Pro Trp Pro Thr Leu
385                 390                 395                 400

Val Thr Thr Leu Ser Tyr Gly Val Gln Cys Phe Ser Arg Tyr Pro Asp
                405                 410                 415

His Met Lys Gln His Asp Phe Phe Lys Ser Ala Met Pro Glu Gly Tyr
            420                 425                 430

Val Gln Glu Arg Thr Ile Phe Phe Lys Asp Asp Gly Asn Tyr Lys Thr
        435                 440                 445

Arg Ala Glu Val Lys Phe Glu Gly Asp Thr Leu Val Asn Arg Ile Glu
450                 455                 460

Leu Lys Gly Ile Asp Phe Lys Glu Asp Gly Asn Ile Leu Gly His Lys
465                 470                 475                 480

Leu Glu Tyr Asn Tyr Asn Ser His Asn Val Tyr Ile Met Ala Asp Lys
                485                 490                 495

Gln Lys Asn Gly Ile Lys Val Asn Phe Lys Ile Arg His Asn Ile Glu
            500                 505                 510

Asp Gly Ser Val Gln Leu Ala Asp His Tyr Gln Gln Asn Thr Pro Ile
        515                 520                 525

Gly Asp Gly Pro Val Leu Leu Pro Asp Asn His Tyr Leu Ser Thr Gln
530                 535                 540

Ser Ala Leu Ser Lys Asp Pro Asn Glu Lys Arg Asp His Met Val Leu
545                 550                 555                 560

-continued

Leu Glu Phe Val Thr Ala Ala Gly Ile Thr Leu Gly Met Asp Glu Leu
            565                 570                 575

Tyr Lys

<210> SEQ ID NO 20
<211> LENGTH: 1737
<212> TYPE: DNA
<213> ORGANISM: Artificial Sequence
<220> FEATURE:
<223> OTHER INFORMATION: ORF encoding BRET construct of SEQ ID NO:19

<400> SEQUENCE: 20

```
atgtcgggag aattgtggat taccctagtt gacacagcgg acattgtcgg cgtcaccctc      60
accttctgtg tcaacattgt tcttctcgga cttctgaaaa cacgtggaaa aaacttgggc     120
acttataaat atctcatggc gttttttctca gtattctcga ttttttacgc catcatcgag     180
ttcatattac gacctataat gcatattgag aacaccactt tcttttttgat ctcaaggaaa     240
agattcaact actccaccaa acttggaaaa atcaactctg cgttttactg tgcttgtttt     300
gccaccagtt tgttgtctc aggagttcac tttgtttatc gatattttgc aacttgcaaa      360
ccgaatctac ttcgtttgtt caacttgcca actcttctac tttggccact tggttgcagt     420
gtacccgtga caatgtgggc tagtgtctca tattttttgt atccagatac cgagtacacg     480
gaagcggctg tcaccaatgt actaaataac cactataact ggatcaaaaa ggagaatgta     540
tcgtacattg catacgtcta ttaccaatac gaaaacggag taaggcatat ctacctcaaa     600
aacttgcttg gatgctttgt tcattacttt gtcatgtcga tgacgtttgt tgtgatgttc     660
tactgcggat atgccacgtg gaaaactatg aatgaacaca aggatgtatc tgatagaact     720
cgagcgctac agaaacaact tttcaaagct ttagttcttc agacactcat cccaactatc     780
ttcatgtacg ccccaactgg agtcatgttc atcgcaccgt tttttgacgt gaatttgaat     840
gcaaacgcca atttcattgt gttttgctca tttctgtacc cgggactcga tccactcatt     900
ctgattttga tcattcgtga tttccgaaga acaatattca atttcttgtg tggaaagaaa     960
aacagtgttg atgaatcccg ctcgacaaca agagccaatt tgtctcaagt tccgacgatg    1020
gtgagcaagg gcgaggagct gttcaccggg gtggtgccca tcctggtcga gctggacggc    1080
gacgtaaacg gccacaagtt cagcgtgtcc ggcgagggcg agggcgatgc cacctacggc    1140
aagctgaccc tgaagttcat ctgcaccacc ggcaagctgc ccgtgccctg gcccaccctc    1200
gtgaccaccc tgagctacgg cgtgcagtgc ttcagccgct accccgacca catgaagcag    1260
cacgacttct tcaagtccgc catgcccgaa ggctacgtcc aggagcgcac catcttcttc    1320
aaggacgacg gcaactacaa gacccgcgcc gaggtgaagt tcgagggcga cacccctggtg    1380
aaccgcatcg agctgaaggg catcgacttc aaggaggacg gcaacatcct ggggcacaag    1440
ctggagtaca actacaacag ccacaacgtc tatatcatgg ccgacaagca gaagaacggc    1500
atcaaggtga acttcaagat ccgccacaac atcgaggacg gcagcgtgca gctcgccgac    1560
cactaccagc agaacacccc catcggcgac ggccccgtgc tgctgcccga caaccactac    1620
ctgagcaccc agtccgccct gagcaaagac cccaacgaga gcgcgatca catggtcctg    1680
ctggagttcg tgaccgccgc cgggatcact ctcggcatgg acgagctgta caagtaa      1737
```

<210> SEQ ID NO 21
<211> LENGTH: 30
<212> TYPE: DNA
<213> ORGANISM: Artificial Sequence
<220> FEATURE:

<223> OTHER INFORMATION: Oligonucleotide primer

<400> SEQUENCE: 21
agtctagaat gtcgggagaa ttgtggatta                                30

<210> SEQ ID NO 22
<211> LENGTH: 49
<212> TYPE: DNA
<213> ORGANISM: Artificial Sequence
<220> FEATURE:
<223> OTHER INFORMATION: Oligonucleotide primer

<400> SEQUENCE: 22
ggggacaagt ttgtacaaaa aagcaggctt catcacgtcg gaacttgag           49

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 23
aaccatgtcg ggagaattgt g                                         21

<210> SEQ ID NO 24
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 24
tgtagcgctc gcttgtacag ctcgtccat                                 29

<210> SEQ ID NO 25
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 25
gagctgtaca agcgagcgct acagaaacaa                                30

<210> SEQ ID NO 26
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 26
cttgctggtc atcgtcggaa cttgagaca                                 29

<210> SEQ ID NO 27
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 27
caagttccga cgatgaccag caaggtgta                                 29

<210> SEQ ID NO 28

```
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 28
gttactgctc gttcttca                                                 18

<210> SEQ ID NO 29
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 29
gagctgtaca agcgagcgct acagaaacaa                                    30

<210> SEQ ID NO 30
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 30
gttactgctc gttcttca                                                 18

<210> SEQ ID NO 31
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 31
aaccatgtcg ggagaattgt g                                             21

<210> SEQ ID NO 32
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 32
gttactgctc gttcttca                                                 18

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 33
aaccatgtcg ggagaattgt g                                             21

<210> SEQ ID NO 34
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 34
```

```
ctgtagcgct cgctgctcgt tcttcag                                              27
```

<210> SEQ ID NO 35
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 35

```
aagaacgagc agcgagcgct acagaaaca                                            29
```

<210> SEQ ID NO 36
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 36

```
cttgctcacc atcgtcggaa cttgagaca                                            29
```

<210> SEQ ID NO 37
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 37

```
caagttccga cgatggtgag caagggcga                                            29
```

<210> SEQ ID NO 38
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 38

```
gttacttgta cagctcgtc                                                       19
```

<210> SEQ ID NO 39
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 39

```
aagaacgagc agcgagcgct acagaaaca                                            29
```

<210> SEQ ID NO 40
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 40

```
gttacttgta cagctcgtc                                                       19
```

<210> SEQ ID NO 41
<211> LENGTH: 21
<212> TYPE: DNA
<213> ORGANISM: Artificial Sequence
<220> FEATURE:

<223> OTHER INFORMATION: Oligonucleotide primer

<400> SEQUENCE: 41
aaccatgtcg ggagaattgt g    21

<210> SEQ ID NO 42
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 42
gttacttgta cagctcgtc    19

<210> SEQ ID NO 43
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 43
caccagtttt gttgtctcag gagtttattt tgtttatcga tattttgcaa ctt    53

<210> SEQ ID NO 44
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 44
aagttgcaaa atatcgataa acaaaataaa ctcctgagac aacaaaactg gtg    53

<210> SEQ ID NO 45
<211> LENGTH: 238
<212> TYPE: PRT
<213> ORGANISM: Artificial Sequence
<220> FEATURE:
<223> OTHER INFORMATION: mCitrine derivative

<400> SEQUENCE: 45

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Gly Tyr Gly Leu Met Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly

```
                145                 150                 155                 160
Ile Lys Val Asn Phe Lys Ile Arg His Asn Ile Glu Asp Gly Ser Val
                    165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Tyr Gln Ser Arg Leu Ser
            195                 200                 205

Lys Asp Pro Asn Glu Lys Arg Asp His Met Val Leu Leu Glu Phe Val
        210                 215                 220

Thr Ala Ala Gly Ile Thr His Gly Met Asp Glu Leu Tyr Lys
225                 230                 235

<210> SEQ ID NO 46
<211> LENGTH: 238
<212> TYPE: PRT
<213> ORGANISM: Artificial Sequence
<220> FEATURE:
<223> OTHER INFORMATION: mCFP derivative

<400> SEQUENCE: 46

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Ile
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Arg Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 47
<211> LENGTH: 717
<212> TYPE: DNA
<213> ORGANISM: Artificial Sequence
<220> FEATURE:
<223> OTHER INFORMATION: Codon optimized ORF encoding SEQ ID NO:45
```

<400> SEQUENCE: 47

```
atgtctaaag gtgaagaatt attcactggt gttgtcccaa ttttggttga attagatggt    60
gatgttaatg gtcacaaatt ttctgtctcc ggtgaaggtg aaggtgatgc tacttacggt   120
aaattgacct aaaatttat ttgtactact ggtaaattgc cagttccatg gccaacctta   180
gtcactactt taggttatgg tttgatgtgt tttgctagat acccagatca tatgaaacaa   240
catgactttt tcaagtctgc catgccagaa ggttatgttc aagaaagaac tatttttttc   300
aaagatgacg gtaactacaa gaccagagct gaagtcaagt ttgaaggtga taccttagtt   360
aatagaatcg aattaaaagg tattgatttt aagaagatg gtaacatttt aggtcacaaa    420
ttggaataca actataactc tcacaatgtt tacatcatgg ctgacaaaca aaagaatggt   480
atcaaagtta acttcaaaat tagacacaac attgaagatg gttctgttca attagctgac   540
cattatcaac aaaatactcc aattggtgat ggtccagtct tgttaccaga caaccattac   600
ttatcctatc aatctagatt atccaaagat ccaaacgaaa agagagacca catggtcttg   660
ttagaatttg ttactgctgc tggtattacc catggtatgg atgaattgta caaataa      717
```

<210> SEQ ID NO 48
<211> LENGTH: 717
<212> TYPE: DNA
<213> ORGANISM: Artificial Sequence
<220> FEATURE:
<223> OTHER INFORMATION: Codon optimized ORF encoding SEQ ID NO:46

<400> SEQUENCE: 48

```
atgtctaaag gtgaagaatt attcactggt gttgtcccaa ttttggttga attagatggt    60
gatgttaatg gtcacaaatt ttctgtctcc ggtgaaggtg aaggtgatgc tacttacggt   120
aaattgacct aaaatttat ttgtactact ggtaaattgc cagttccatg gccaacctta   180
gtcactactt taacttgggg tgttcaatgt ttttctagat acccagatca tatgaaacaa   240
catgactttt tcaagtctgc catgccagaa ggttatgttc aagaaagaac tatttttttc   300
aaagatgacg gtaactacaa gaccagagct gaagtcaagt ttgaaggtga taccttagtt   360
aatagaatcg aattaaaagg tattgatttt aagaagatg gtaacatttt aggtcacaaa    420
ttggaataca tttataactc tcacaatgtt tacatcactg ctgacaaaca aaagaatggt   480
atcaaagcta acttcaaaat tagacacaac attgaagatg gttctgttca attagctgac   540
cattatcaac aaaatactcc aattggtgat ggtccagtct tgttaccaga caaccattac   600
ttatccactc aatctagatt atccaaagat ccaaacgaaa agagagacca catggtcttg   660
ttagaatttg ttactgctgc tggtattacc catggtatgg atgaattgta caaataa      717
```

<210> SEQ ID NO 49
<211> LENGTH: 2448
<212> TYPE: DNA
<213> ORGANISM: Artificial Sequence
<220> FEATURE:
<223> OTHER INFORMATION: ORF encoding FRET construct

<400> SEQUENCE: 49

```
atgtcgggag aattgtggat taccctagtt gacacagcgg acattgtcgg cgtcaccctc    60
accttctgtg tcaacattgt tcttctcgga cttctgaaaa cacgtggaaa aaacttgggc   120
acttataaat atctcatggc gttttctca gtattctcga ttttttacgc catcatcgag    180
ttcatattac gacctataat gcatattgag aacaccactt tctttttgat ctcaaggaaa   240
agattcaact actccaccaa acttggaaaa atcaactctg cgttttactg tgcttgttt     300
```

-continued

```
gccaccagtt tgttgtctc aggagttcac tttgtttatc gatattttgc aacttgcaaa    360
ccgaatctac ttcgtttgtt caacttgcca actcttctac tttggccact tggttgcagt    420
gtacccgtga caatgtgggc tagtgtctca tatttttgt atccagatac cgagtacacg     480
gaagcggctg tcaccaatgt actaaataac cactataact ggatcaaaaa ggagaatgta    540
tcgtacattg catacgtcta ttaccaatac gaaaacggag taaggcatat ctacctcaaa    600
aacttgcttg gatgctttgt tcattacttt gtcatgtcga tgacgtttgt tgtgatgttc    660
tactgcggat atgccacgtg gaaaactatg aatgaacaca aggatgtatc tgatagaact    720
atgtctaaag gtgaagaatt attcactggt gttgtcccaa ttttggttga attagatggt    780
gatgttaatg gtcacaaatt ttctgtctcc ggtgaaggtg aaggtgatgc tacttacggt    840
aaattgacct aaaatttat ttgtactact ggtaaattgc cagttccatg gccaacctta     900
gtcactactt taacttgggg tgttcaatgt ttttctagat acccagatca tatgaaacaa    960
catgactttt tcaagtctgc catgccagaa ggttatgttc aagaaagaac tattttttc    1020 aaagatgacg gtaactacaa gaccagagct gaagtcaagt ttgaaggtga taccttagtt   1080
aatagaatcg aattaaaagg tattgatttt aaagaagatg gtaacatttt aggtcacaaa   1140
ttggaataca tttataactc tcacaatgtt tacatcactg ctgacaaaca aaagaatggt   1200
atcaaagcta acttcaaaat tagacacaac attgaagatg gttctgttca attagctgac   1260
cattatcaac aaaatactcc aattggtgat ggtccagtct tgttaccaga caaccattac   1320
ttatccactc aatctagatt atccaaagat ccaaacgaaa agagagacca catggtcttg   1380
ttagaatttg ttactgctgc tggtattacc catggtatgg atgaattgta caaacgagcg   1440
ctacagaaac aacttttcaa agctttagtt cttcagacac tcatcccaac tatcttcatg   1500
tacgccccaa ctggagtcat gttcatcgca ccgttttttg acgtgaattt gaatgcaaac   1560
gccaatttca ttgtgttttg ctcatttctg tacccgggac tcgatccact cattctgatt   1620
ttgatcattc gtgattccg aagaacaata ttcaattct tgtgtggaaa gaaaaacagt    1680
gttgatgaat cccgctcgac aacaagagcc aatttgtctc aagttccgac gatgtctaaa   1740
ggtgaagaat tattcactgg tgttgtccca attttggttg aattagatgg tgatgttaat   1800
ggtcacaaat tttctgtctc cggtgaaggt gaaggtgatg ctacttacgg taaattgacc   1860
ttaaaattta tttgtactac tggtaaattg ccagttccat ggccaacctt agtcactact   1920
ttaggttatg gtttgatgtg ttttgctaga tacccagatc atatgaaaca acatgacttt   1980
ttcaagtctg ccatgccaga aggttatgtt caagaaagaa ctatttttt caaagatgac   2040 ggtaactaca agaccagagc tgaagtcaag tttgaaggtg ataccttagt taatagaatc   2100
gaattaaaag gtattgattt taagaagat ggtaacattt taggtcacaa attggaatac    2160
aactataact ctcacaatgt ttacatcatg ctgacaaac aaaagaatgg tatcaaagtt    2220
aacttcaaaa ttagacacaa cattgaagat ggttctgttc aattagctga ccattatcaa   2280
caaaatactc caattggtga tggtccagtc ttgttaccag acaaccatta cttatcctat   2340
caatctagat tatccaaaga tccaaacgaa aagagagacc acatggtctt gttagaattt   2400
gttactgctg ctggtattac ccatggtatg gatgaattgt acaaataa                2448
```

<210> SEQ ID NO 50
<211> LENGTH: 815
<212> TYPE: PRT
<213> ORGANISM: Artificial Sequence
<220> FEATURE:
<223> OTHER INFORMATION: FRETConstruct -continued

<400> SEQUENCE: 50

```
Met Ser Gly Glu Leu Trp Ile Thr Leu Val Asp Thr Ala Asp Ile Val
1               5                   10                  15

Gly Val Thr Leu Thr Phe Cys Val Asn Ile Val Leu Leu Gly Leu Leu
            20                  25                  30

Lys Thr Arg Gly Lys Asn Leu Gly Thr Tyr Lys Tyr Leu Met Ala Phe
        35                  40                  45

Phe Ser Val Phe Ser Ile Phe Tyr Ala Ile Ile Glu Phe Ile Leu Arg
    50                  55                  60

Pro Ile Met His Ile Glu Asn Thr Thr Phe Phe Leu Ile Ser Arg Lys
65                  70                  75                  80

Arg Phe Asn Tyr Ser Thr Lys Leu Gly Lys Ile Asn Ser Ala Phe Tyr
                85                  90                  95

Cys Ala Cys Phe Ala Thr Ser Phe Val Val Ser Gly Val His Phe Val
            100                 105                 110

Tyr Arg Tyr Phe Ala Thr Cys Lys Pro Asn Leu Leu Arg Leu Phe Asn
        115                 120                 125

Leu Pro Thr Leu Leu Leu Trp Pro Leu Gly Cys Ser Val Pro Val Thr
    130                 135                 140

Met Trp Ala Ser Val Ser Tyr Phe Leu Tyr Pro Asp Thr Glu Tyr Thr
145                 150                 155                 160

Glu Ala Ala Val Thr Asn Val Leu Asn Asn His Tyr Asn Trp Ile Lys
                165                 170                 175

Lys Glu Asn Val Ser Tyr Ile Ala Tyr Val Tyr Tyr Gln Tyr Glu Asn
            180                 185                 190

Gly Val Arg His Ile Tyr Leu Lys Asn Leu Leu Gly Cys Phe Val His
        195                 200                 205

Tyr Phe Val Met Ser Met Thr Phe Val Val Met Phe Tyr Cys Gly Tyr
    210                 215                 220

Ala Thr Trp Lys Thr Met Asn Glu His Lys Asp Val Ser Asp Arg Thr
225                 230                 235                 240

Met Ser Lys Gly Glu Glu Leu Phe Thr Gly Val Val Pro Ile Leu Val
                245                 250                 255

Glu Leu Asp Gly Asp Val Asn Gly His Lys Phe Ser Val Ser Gly Glu
            260                 265                 270

Gly Glu Gly Asp Ala Thr Tyr Gly Lys Leu Thr Leu Lys Phe Ile Cys
        275                 280                 285

Thr Thr Gly Lys Leu Pro Val Pro Trp Pro Thr Leu Thr Thr Leu
    290                 295                 300

Thr Trp Gly Val Gln Cys Phe Ser Arg Tyr Pro Asp His Met Lys Gln
305                 310                 315                 320

His Asp Phe Phe Lys Ser Ala Met Pro Glu Gly Tyr Val Gln Glu Arg
                325                 330                 335

Thr Ile Phe Phe Lys Asp Asp Gly Asn Tyr Lys Thr Arg Ala Glu Val
            340                 345                 350

Lys Phe Glu Gly Asp Thr Leu Val Asn Arg Ile Glu Leu Lys Gly Ile
        355                 360                 365

Asp Phe Lys Glu Asp Gly Asn Ile Leu Gly His Lys Leu Glu Tyr Ile
    370                 375                 380

Tyr Asn Ser His Asn Val Tyr Ile Thr Ala Asp Lys Gln Lys Asn Gly
385                 390                 395                 400

Ile Lys Ala Asn Phe Lys Ile Arg His Asn Ile Glu Asp Gly Ser Val
                405                 410                 415
```

```
Gln Leu Ala Asp His Tyr Gln Gln Asn Thr Pro Ile Gly Asp Gly Pro
            420                 425                 430

Val Leu Pro Asp Asn His Tyr Leu Ser Thr Gln Ser Arg Leu Ser
        435                 440                 445

Lys Asp Pro Asn Glu Lys Arg Asp His Met Val Leu Leu Glu Phe Val
450                 455                 460

Thr Ala Ala Gly Ile Thr His Gly Met Asp Glu Leu Tyr Lys Arg Ala
465                 470                 475                 480

Leu Gln Lys Gln Leu Phe Lys Ala Leu Val Leu Gln Thr Leu Ile Pro
                485                 490                 495

Thr Ile Phe Met Tyr Ala Pro Thr Gly Val Met Phe Ile Ala Pro Phe
            500                 505                 510

Phe Asp Val Asn Leu Asn Ala Asn Ala Asn Phe Ile Val Phe Cys Ser
        515                 520                 525

Phe Leu Tyr Pro Gly Leu Asp Pro Leu Ile Leu Ile Leu Ile Ile Arg
        530                 535                 540

Asp Phe Arg Arg Thr Ile Phe Asn Phe Leu Cys Gly Lys Lys Asn Ser
545                 550                 555                 560

Val Asp Glu Ser Arg Ser Thr Thr Arg Ala Asn Leu Ser Gln Val Pro
                565                 570                 575

Thr Met Ser Lys Gly Glu Glu Leu Phe Thr Gly Val Val Pro Ile Leu
            580                 585                 590

Val Glu Leu Asp Gly Asp Val Asn Gly His Lys Phe Ser Val Ser Gly
        595                 600                 605

Glu Gly Glu Gly Asp Ala Thr Tyr Gly Lys Leu Thr Leu Lys Phe Ile
610                 615                 620

Cys Thr Thr Gly Lys Leu Pro Val Pro Trp Pro Thr Leu Val Thr Thr
625                 630                 635                 640

Leu Gly Tyr Gly Leu Met Cys Phe Ala Arg Tyr Pro Asp His Met Lys
                645                 650                 655

Gln His Asp Phe Phe Lys Ser Ala Met Pro Glu Gly Tyr Val Gln Glu
            660                 665                 670

Arg Thr Ile Phe Phe Lys Asp Asp Gly Asn Tyr Lys Thr Arg Ala Glu
        675                 680                 685

Val Lys Phe Glu Gly Asp Thr Leu Val Asn Arg Ile Glu Leu Lys Gly
        690                 695                 700

Ile Asp Phe Lys Glu Asp Gly Asn Ile Leu Gly His Lys Leu Glu Tyr
705                 710                 715                 720

Asn Tyr Asn Ser His Asn Val Tyr Ile Met Ala Asp Lys Gln Lys Asn
                725                 730                 735

Gly Ile Lys Val Asn Phe Lys Ile Arg His Asn Ile Glu Asp Gly Ser
            740                 745                 750

Val Gln Leu Ala Asp His Tyr Gln Gln Asn Thr Pro Ile Gly Asp Gly
        755                 760                 765

Pro Val Leu Leu Pro Asp Asn His Tyr Leu Ser Tyr Gln Ser Arg Leu
770                 775                 780

Ser Lys Asp Pro Asn Glu Lys Arg Asp His Met Val Leu Leu Glu Phe
785                 790                 795                 800

Val Thr Ala Ala Gly Ile Thr His Gly Met Asp Glu Leu Tyr Lys
                805                 810                 815

<210> SEQ ID NO 51
<211> LENGTH: 2694
<212> TYPE: DNA
<213> ORGANISM: Artificial Sequence
```

-continued

<220> FEATURE:
<223> OTHER INFORMATION: ORF encoding BRET construct

<400> SEQUENCE: 51

| | |
|---|---|
| atgggttctg gtcaattatg gttggcttta gttgatgctg cagatatggt tggttttact | 60 |
| ttgacaatct caattaatat cattttgtta ggtttgatta gaactagagg taaaaccttg | 120 |
| ggtacttaca agtacttgat gtctttcttt tctttctttt ctattttcta tgcaatcgtt | 180 |
| gaatctatct tgagaccaat catgcatatc gaaaacacta cattttttctt aatctccaga | 240 |
| aagagattcg attacagtac tagattgggt aaaattaatt cagctttcta ctgtgcttgt | 300 |
| ttcgcaacat ccttcgtttt gagtgcagtt catttcgttt acagatactt cgctgcttgt | 360 |
| aagcctaatt tgttgagatt gtttaactta cctcatttgt tattgtggcc attgatgtgt | 420 |
| tcaattcctg ttactgcttg ggcatctgtt tcatactttt tgtacccaga tacagaatat | 480 |
| accgaagctg cagttaccta tgttttgaag actcattacg aagttattaa aaaggaaaac | 540 |
| gtttcttaca ttgcttacgt ttactaccaa tacgaaaacg gtgaaagaca tatctatatt | 600 |
| aaaaacttat tgggttgttt cgttcattac ttcgttatgt ctatgacatt cgttgttgtt | 660 |
| ttctattgtg gtttctcaac ttggtggaca attagagaac atagaggtgc ttccgataga | 720 |
| acaatggtta gtaagggtga agaattattc accggtgttg ttccaatttt ggttgaatta | 780 |
| gatggtgacg ttaatggtca taaattttcc gttagtggtg aaggtgaagg tgacgcaaca | 840 |
| tacggtaaat tgaccttgaa gtttatttgt accactggta aattgccagt ccttggcca | 900 |
| accttggtta caaccttaac ttatggtgtt caatgttttt ccagataccc tgatcatatg | 960 |
| aagcaacatg atttctttaa gagtgctatg ccagaaggtt acgttcaaga agaacaatt | 1020 |
| ttctttaagg atgatggtaa ctacaagact agagcagagg ttaagttcga aggtgacaca | 1080 |
| ttggttaaca gaatcgaatt gaagggtatc gatttcaagg aagatggtaa catcttgggt | 1140 |
| cataagttgg aatacaatta caactcccat aacgtttaca tcatggctga taagcaaaag | 1200 |
| aatggtatta agttaacttt caagatcaga cataacatcg aagatggttc agttcaattg | 1260 |
| gcagatcatt accaacaaaa caccccctatt ggtgacggtc ctgttttgtt gccagataac | 1320 |
| cattacttat caactcaatc cgctttgagt aaggatccaa acgaaaagag agatcatatg | 1380 |
| gttttgttgg aattcgttac tgctgcaggt atcacattgg gtatggatga attgtacaag | 1440 |
| agacatttgc atagacaatt gtttaaagct ttggttttcc aaaccttggt tccatcaatt | 1500 |
| tttatgtaca tccctactgg tgttatgttc atcgcaccat ttttcgatat caatttgaac | 1560 |
| gctaacgcaa acttcatcgt tttctgttca tttttgtatc ctggtttgga tccattgatc | 1620 |
| ttgattttca ttatcagaga attcagagtt acaattttaa acattattcg tggtaatgaa | 1680 |
| cgtggtaacg ctgttggtga agcatactct acctcaagaa ttaaatcttc acaaccagct | 1740 |
| gcagttaatt tgtctggtat gacatcaaag gtttacgatc ctgaacaaag aaaaagaatg | 1800 |
| attaccggtc cacaatggtg ggctcgttgt aagcaaatga cgttttgga ttctttcatt | 1860 |
| aactactacg attcagaaaa gcatgctgaa acgctgtta ttttcttgca tggtaacgct | 1920 |
| gcatccagtt atttgtggag acatgttgtt cctcatattg aaccagttgc tagatgtatc | 1980 |
| atccctgatt tgatcggtat gggtaaatct ggtaaatctg gtaacggttc ttacagattg | 2040 |
| ttggatcatt acaagtactt aactgcatgg ttcgaattgt tgaatttgcc aaagaaaatt | 2100 |
| atcttcgttg gtcatgattg gggtgcttgt ttggcatttc attactctta cgaacatcaa | 2160 |
| gataaaatta aggctatcgt tcatgcagaa tccgttgttg atgttattga agttgggat | 2220 |
| gaatggccag atatcgaaga agatatcgct ttaattaagt ccgaagaagg tgaaaagatg | 2280 |

```
gttttggaaa caacttttt cgttgaaact atgttgccta gtaagatcat gagaaagttg    2340
gaacctgaag aatttgctgc atatttggaa ccattcaaag aaaagggtga agttagaaga    2400
cctacattat cttggcctag agaaattcca ttggttaaag gtggtaaacc agatgttgtt    2460
caaatcgtta gaaactacaa cgcttactta agagcatctg atgatttgcc aaagatgttc    2520
atcgaatctg atcctggttt cttttctaat gctattgttg aaggtgctaa gaaattccct    2580
aacacagaat tcgttaaggt taagggtttg catttctctc aagaagatgc tccagatgaa    2640
atgggtaaat acatcaagtc atttgttgaa agagttttga aaaatgaaca ataa          2694
```

<210> SEQ ID NO 52
<211> LENGTH: 897
<212> TYPE: PRT
<213> ORGANISM: Artificial Sequence
<220> FEATURE:
<223> OTHER INFORMATION: BRET Construct

<400> SEQUENCE: 52

```
Met Gly Ser Gly Gln Leu Trp Leu Ala Leu Val Asp Ala Ala Asp Met
 1               5                  10                  15

Val Gly Phe Thr Leu Thr Ile Ser Ile Asn Ile Ile Leu Gly Leu
                20                  25                  30

Ile Arg Thr Arg Gly Lys Thr Leu Gly Thr Tyr Lys Tyr Leu Met Ser
            35                  40                  45

Phe Phe Ser Phe Phe Ser Ile Phe Tyr Ala Ile Val Glu Ser Ile Leu
        50                  55                  60

Arg Pro Ile Met His Ile Glu Asn Thr Thr Phe Phe Leu Ile Ser Arg
65                  70                  75                  80

Lys Arg Phe Asp Tyr Ser Thr Arg Leu Gly Lys Ile Asn Ser Ala Phe
                85                  90                  95

Tyr Cys Ala Cys Phe Ala Thr Ser Phe Val Leu Ser Ala Val His Phe
            100                 105                 110

Val Tyr Arg Tyr Phe Ala Ala Cys Lys Pro Asn Leu Leu Arg Leu Phe
        115                 120                 125

Asn Leu Pro His Leu Leu Leu Trp Pro Leu Met Cys Ser Ile Pro Val
    130                 135                 140

Thr Ala Trp Ala Ser Val Ser Tyr Phe Leu Tyr Pro Asp Thr Glu Tyr
145                 150                 155                 160

Thr Glu Ala Ala Val Thr Tyr Val Leu Lys Thr His Tyr Glu Val Ile
                165                 170                 175

Lys Lys Glu Asn Val Ser Tyr Ile Ala Tyr Val Tyr Gln Tyr Glu
            180                 185                 190

Asn Gly Glu Arg His Ile Tyr Ile Lys Asn Leu Leu Gly Cys Phe Val
        195                 200                 205

His Tyr Phe Val Met Ser Met Thr Phe Val Val Phe Tyr Cys Gly
    210                 215                 220

Phe Ser Thr Trp Trp Thr Ile Arg Glu His Arg Gly Ala Ser Asp Arg
225                 230                 235                 240

Thr Met Val Ser Lys Gly Glu Glu Leu Phe Thr Gly Val Val Pro Ile
                245                 250                 255

Leu Val Glu Leu Asp Gly Asp Val Asn Gly His Lys Phe Ser Val Ser
            260                 265                 270

Gly Glu Gly Glu Gly Asp Ala Thr Tyr Gly Lys Leu Thr Leu Lys Phe
        275                 280                 285

Ile Cys Thr Thr Gly Lys Leu Pro Val Pro Trp Pro Thr Leu Val Thr
```

```
                  290                 295                 300
Thr Leu Thr Tyr Gly Val Gln Cys Phe Ser Arg Tyr Pro Asp His Met
305                 310                 315                 320

Lys Gln His Asp Phe Lys Ser Ala Met Pro Glu Gly Tyr Val Gln
                    325                 330                 335

Glu Arg Thr Ile Phe Phe Lys Asp Asp Gly Asn Tyr Lys Thr Arg Ala
                    340                 345                 350

Glu Val Lys Phe Glu Gly Asp Thr Leu Val Asn Arg Ile Glu Leu Lys
                    355                 360                 365

Gly Ile Asp Phe Lys Glu Asp Gly Asn Ile Leu Gly His Lys Leu Glu
                    370                 375                 380

Tyr Asn Tyr Asn Ser His Asn Val Tyr Ile Met Ala Asp Lys Gln Lys
385                 390                 395                 400

Asn Gly Ile Lys Val Asn Phe Lys Ile Arg His Asn Ile Glu Asp Gly
                    405                 410                 415

Ser Val Gln Leu Ala Asp His Tyr Gln Gln Asn Thr Pro Ile Gly Asp
                    420                 425                 430

Gly Pro Val Leu Leu Pro Asp Asn His Tyr Leu Ser Thr Gln Ser Ala
                    435                 440                 445

Leu Ser Lys Asp Pro Asn Glu Lys Arg Asp His Met Val Leu Leu Glu
450                 455                 460

Phe Val Thr Ala Ala Gly Ile Thr Leu Gly Met Asp Glu Leu Tyr Lys
465                 470                 475                 480

Arg His Leu His Arg Gln Leu Phe Lys Ala Leu Val Phe Gln Thr Leu
                    485                 490                 495

Val Pro Ser Ile Phe Met Tyr Ile Pro Thr Gly Val Met Phe Ile Ala
                    500                 505                 510

Pro Phe Phe Asp Ile Asn Leu Asn Ala Asn Ala Asn Phe Ile Val Phe
                    515                 520                 525

Cys Ser Phe Leu Tyr Pro Gly Leu Asp Pro Leu Ile Leu Ile Phe Ile
                    530                 535                 540

Ile Arg Glu Phe Arg Val Thr Ile Leu Asn Ile Ile Arg Gly Asn Glu
545                 550                 555                 560

Arg Gly Asn Ala Val Gly Glu Ala Tyr Ser Thr Ser Arg Ile Lys Ser
                    565                 570                 575

Ser Gln Pro Ala Ala Val Asn Leu Ser Gly Met Thr Ser Lys Val Tyr
                    580                 585                 590

Asp Pro Glu Gln Arg Lys Arg Met Ile Thr Gly Pro Gln Trp Trp Ala
                    595                 600                 605

Arg Cys Lys Gln Met Asn Val Leu Asp Ser Phe Ile Asn Tyr Tyr Asp
                    610                 615                 620

Ser Glu Lys His Ala Glu Asn Ala Val Ile Phe Leu His Gly Asn Ala
625                 630                 635                 640

Ala Ser Ser Tyr Leu Trp Arg His Val Val Pro His Ile Glu Pro Val
                    645                 650                 655

Ala Arg Cys Ile Ile Pro Asp Leu Ile Gly Met Gly Lys Ser Gly Lys
                    660                 665                 670

Ser Gly Asn Gly Ser Tyr Arg Leu Leu Asp His Tyr Lys Tyr Leu Thr
                    675                 680                 685

Ala Trp Phe Glu Leu Leu Asn Leu Pro Lys Lys Ile Ile Phe Val Gly
                    690                 695                 700

His Asp Trp Gly Ala Cys Leu Ala Phe His Tyr Ser Tyr Glu His Gln
705                 710                 715                 720
```

-continued

```
Asp Lys Ile Lys Ala Ile Val His Ala Glu Ser Val Asp Val Ile
                725                 730                 735

Glu Ser Trp Asp Glu Trp Pro Asp Ile Glu Asp Ile Ala Leu Ile
            740                 745                 750

Lys Ser Glu Glu Gly Glu Lys Met Val Leu Glu Asn Asn Phe Phe Val
        755                 760                 765

Glu Thr Met Leu Pro Ser Lys Ile Met Arg Lys Leu Glu Pro Glu Glu
    770                 775                 780

Phe Ala Ala Tyr Leu Glu Pro Phe Lys Glu Lys Gly Glu Val Arg Arg
785                 790                 795                 800

Pro Thr Leu Ser Trp Pro Arg Glu Ile Pro Leu Val Lys Gly Gly Lys
                805                 810                 815

Pro Asp Val Val Gln Ile Val Arg Asn Tyr Asn Ala Tyr Leu Arg Ala
            820                 825                 830

Ser Asp Asp Leu Pro Lys Met Phe Ile Glu Ser Asp Pro Gly Phe Phe
        835                 840                 845

Ser Asn Ala Ile Val Glu Gly Ala Lys Lys Phe Pro Asn Thr Glu Phe
    850                 855                 860

Val Lys Val Lys Gly Leu His Phe Ser Gln Glu Asp Ala Pro Asp Glu
865                 870                 875                 880

Met Gly Lys Tyr Ile Lys Ser Phe Val Glu Arg Val Leu Lys Asn Glu
                885                 890                 895

Gln
```

```
<210> SEQ ID NO 53
<211> LENGTH: 2673
<212> TYPE: DNA
<213> ORGANISM: Artificial Sequence
<220> FEATURE:
<223> OTHER INFORMATION: ORF encoding 2A adrenergic receptor-BRET
      construct

<400> SEQUENCE: 53
```

| | | | | | |
|---|---|---|---|---|---|
| atgggttatc | cttacgatgt | tccagattat | gcttcaatgg | gttccttaca | accagatgct | 60 |
| ggtaattctt | catggaacgg | tacagaagct | ccaggtggtg | gtaccagagc | aactccatac | 120 |
| tcattgcaag | ttacattgac | cttagtttgt | ttggctggtt | tgttgatgtt | gtttactgtt | 180 |
| ttcggtaacg | ttttggttat | tatcgcagtt | tttacatcta | gagctttgaa | ggcaccacaa | 240 |
| aatttgttct | tagttagttt | ggcttctgca | gatatcttgg | ttgctacatt | agttattcct | 300 |
| ttttctttgg | caaacgaagt | tatgggttat | tggtacttcg | gtaaagtttg | gtgtgaaata | 360 |
| tatttggctt | tggatgtttt | ggttttgtact | tccagtatcg | ttcatttgtg | tgctatctct | 420 |
| ttggatagat | actggtcaat | cacacaagca | atcgaataca | atttgaagag | aaccccaaga | 480 |
| agaattaaag | ctatcatcgt | tactgtttgg | ttatttccg | cagttattag | ttttccacct | 540 |
| ttgatttcca | ttgaaaagaa | aggtgctggt | ggtggtcaac | aacctgcaga | accaagttgt | 600 |
| aagattaatg | atcaaaagtg | gtatgttatt | tcttcatcca | ttggttcttt | ctttgctcca | 660 |
| tgtttgatca | tgatcttggt | ttacgttaga | atctatcaaa | tcgctaagag | aagaactaga | 720 |
| gttccacctt | ctagaagagg | tccagatgca | atggtttcaa | aaggtgaaga | attgttact | 780 |
| ggtgttgttc | ctatttttggt | tgaattagat | ggtgacgtta | atggtcataa | gtttagtgtt | 840 |
| tctggtgaag | gtgaaggtga | cgctacatac | ggtaaattga | ccttgaagtt | tatttgtact | 900 |
| actggtaaat | tgccagttcc | ttggccaacc | ttggttacca | cttaacttaa | tggtgttcaa | 960 |
| tgttttttcca | gatacccaga | tcatatgaag | caacatgatt | tctttaagag | tgctatgcct | 1020 |

```
gaaggttacg ttcaagaaag aactattttc tttaaggatg atggtaacta caagacaaga    1080
gcagaggtta agtttgaagg tgacaccttg gttaacagaa tcgaattgaa gggtatcgat    1140
ttcaaggaag atggtaacat cttgggtcat aagttggaat acaattacaa ctcccataac    1200
gtttacatca tggctgataa gcaaaagaat ggtattaaag ttaacttcaa gatcagacat    1260
aacatcgaag atggttcagt tcaattggca gatcattacc aacaaaacac accaattggt    1320
gacggtcctg ttttgttacc agataaccat tacttgtcaa cccaatccgc tttaagtaaa    1380
gatcctaacg aaaagagaga tcatatggtt ttgttggaat tcgttactgc tgcaggtatc    1440
acattgggta tggatgaatt gtacaagaga tggagaggta gacaaaacag agaaaagaga    1500
ttcactttcg ttttggctgt tgttattggt gttttcgttg tttgttggtt cccatttttc    1560
tttacttaca cattgatcgc agttggttgt cctgttccat ctcaattgtt caacttcttt    1620
ttctggttcg gttactgtaa cagttctttg aacccagtta tatatactat tttcaatcat    1680
gatttcagaa gagcttttaa aaagattttg tgtagaggtg acagaaagag aatcgttatg    1740
acctctaagg tttacgatcc agaacaaaga aagagaatga ttactggtcc tcaatggtgg    1800
gcacgttgta agcaaatgaa cgttttggat tctttttatta actactacga ttcagaaaag    1860
```

```
catgctgaaa acgcagttat tttcttgcat ggtaacgctg catcatccta tttgtggaga    1920
catgttgttc ctcatattga accagttgct agatgtatca tcccagattt gatcggtatg    1980
ggtaaatctg gtaaatctgg taacggttct tacagattgt tggatcatta caagtacttg    2040
acagcatggt tcgaattgtt gaatttgcca agaaaaatta tcttcgttgg tcatgattgg    2100
ggtgcttgtt tggcattcca ttactcatac gaacatcaag ataaaattaa ggctatcgtt    2160
catgcagaat ccgttgttga tgttattgaa agttgggatg aatggccaga tatcgaagaa    2220
gatatcgctt taattaagtc tgaagaaggt gaaagatgg ttttggaaaa caacttttc    2280 gttgaaacca tgttgccttc aaagatcatg agaaagttgg aaccagaaga attcgctgca    2340
tatttggaac ctttaaaga aaagggtgaa gttagaagac caactttgtc atggcctaga    2400
gaaattccat tagttaaagg tggtaaacct gatgttgttc aaatcgttag aaactacaac    2460
gcttacttga gagcatctga tgatttgcct aagatgttca tcgaatccga tccaggtttc    2520
ttttctaatg ctattgttga aggtgctaag aaattcccaa acactgaatt cgttaaggtt    2580
aagggtttgc atttctctca agaagatgct cctgatgaaa tgggtaaata catcaagtca    2640
ttcgttgaaa gagttttgaa aaatgaacaa taa    2673
```

<210> SEQ ID NO 54
<211> LENGTH: 890
<212> TYPE: PRT
<213> ORGANISM: Artificial Sequence
<220> FEATURE:
<223> OTHER INFORMATION: 2A adrenergic receptor-BRET construct

<400> SEQUENCE: 54

```
Met Gly Tyr Pro Tyr Asp Val Pro Asp Tyr Ala Ser Met Gly Ser Leu
1               5                   10                  15

Gln Pro Asp Ala Gly Asn Ser Ser Trp Asn Gly Thr Glu Ala Pro Gly
            20                  25                  30

Gly Gly Thr Arg Ala Thr Pro Tyr Ser Leu Gln Val Thr Leu Thr Leu
        35                  40                  45

Val Cys Leu Ala Gly Leu Leu Met Leu Phe Thr Val Phe Gly Asn Val
    50                  55                  60

Leu Val Ile Ile Ala Val Phe Thr Ser Arg Ala Leu Lys Ala Pro Gln
65                  70                  75                  80
```

-continued

```
Asn Leu Phe Leu Val Ser Leu Ala Ser Ala Asp Ile Leu Val Ala Thr
                 85                  90                  95
Leu Val Ile Pro Phe Ser Leu Ala Asn Glu Val Met Gly Tyr Trp Tyr
            100                 105                 110
Phe Gly Lys Val Trp Cys Glu Ile Tyr Leu Ala Leu Asp Val Leu Phe
        115                 120                 125
Cys Thr Ser Ser Ile Val His Leu Cys Ala Ile Ser Leu Asp Arg Tyr
    130                 135                 140
Trp Ser Ile Thr Gln Ala Ile Glu Tyr Asn Leu Lys Arg Thr Pro Arg
145                 150                 155                 160
Arg Ile Lys Ala Ile Ile Val Thr Val Trp Val Ile Ser Ala Val Ile
                165                 170                 175
Ser Phe Pro Pro Leu Ile Ser Ile Glu Lys Lys Gly Ala Gly Gly Gly
            180                 185                 190
Gln Gln Pro Ala Glu Pro Ser Cys Lys Ile Asn Asp Gln Lys Trp Tyr
        195                 200                 205
Val Ile Ser Ser Ser Ile Gly Ser Phe Phe Ala Pro Cys Leu Ile Met
    210                 215                 220
Ile Leu Val Tyr Val Arg Ile Tyr Gln Ile Ala Lys Arg Arg Thr Arg
225                 230                 235                 240
Val Pro Pro Ser Arg Arg Gly Pro Asp Ala Met Val Ser Lys Gly Glu
                245                 250                 255
Glu Leu Phe Thr Gly Val Val Pro Ile Leu Val Glu Leu Asp Gly Asp
            260                 265                 270
Val Asn Gly His Lys Phe Ser Val Ser Gly Glu Gly Glu Gly Asp Ala
        275                 280                 285
Thr Tyr Gly Lys Leu Thr Leu Lys Phe Ile Cys Thr Thr Gly Lys Leu
    290                 295                 300
Pro Val Pro Trp Pro Thr Leu Val Thr Thr Leu Thr Tyr Gly Val Gln
305                 310                 315                 320
Cys Phe Ser Arg Tyr Pro Asp His Met Lys Gln His Asp Phe Phe Lys
                325                 330                 335
Ser Ala Met Pro Glu Gly Tyr Val Gln Glu Arg Thr Ile Phe Phe Lys
            340                 345                 350
Asp Asp Gly Asn Tyr Lys Thr Arg Ala Glu Val Lys Phe Glu Gly Asp
        355                 360                 365
Thr Leu Val Asn Arg Ile Glu Leu Lys Gly Ile Asp Phe Lys Glu Asp
    370                 375                 380
Gly Asn Ile Leu Gly His Lys Leu Glu Tyr Asn Tyr Asn Ser His Asn
385                 390                 395                 400
Val Tyr Ile Met Ala Asp Lys Gln Lys Asn Gly Ile Lys Val Asn Phe
                405                 410                 415
Lys Ile Arg His Asn Ile Glu Asp Gly Ser Val Gln Leu Ala Asp His
            420                 425                 430
Tyr Gln Gln Asn Thr Pro Ile Gly Asp Gly Pro Val Leu Leu Pro Asp
        435                 440                 445
Asn His Tyr Leu Ser Thr Gln Ser Ala Leu Ser Lys Asp Pro Asn Glu
    450                 455                 460
Lys Arg Asp His Met Val Leu Leu Glu Phe Val Thr Ala Ala Gly Ile
465                 470                 475                 480
Thr Leu Gly Met Asp Glu Leu Tyr Lys Arg Trp Arg Gly Arg Gln Asn
                485                 490                 495
Arg Glu Lys Arg Phe Thr Phe Val Leu Ala Val Val Ile Gly Val Phe
```

```
                500             505             510
Val Val Cys Trp Phe Pro Phe Phe Thr Tyr Thr Leu Ile Ala Val
            515             520             525

Gly Cys Pro Val Pro Ser Gln Leu Phe Asn Phe Phe Trp Phe Gly
            530             535             540

Tyr Cys Asn Ser Ser Leu Asn Pro Val Ile Tyr Thr Ile Phe Asn His
545             550             555             560

Asp Phe Arg Arg Ala Phe Lys Lys Ile Leu Cys Arg Gly Asp Arg Lys
            565             570             575

Arg Ile Val Met Thr Ser Lys Val Tyr Asp Pro Glu Gln Arg Lys Arg
            580             585             590

Met Ile Thr Gly Pro Gln Trp Trp Ala Arg Cys Lys Gln Met Asn Val
            595             600             605

Leu Asp Ser Phe Ile Asn Tyr Tyr Asp Ser Glu Lys His Ala Glu Asn
            610             615             620

Ala Val Ile Phe Leu His Gly Asn Ala Ala Ser Ser Tyr Leu Trp Arg
625             630             635             640

His Val Val Pro His Ile Glu Pro Val Ala Arg Cys Ile Ile Pro Asp
            645             650             655

Leu Ile Gly Met Gly Lys Ser Gly Lys Ser Gly Asn Gly Ser Tyr Arg
            660             665             670

Leu Leu Asp His Tyr Lys Tyr Leu Thr Ala Trp Phe Glu Leu Leu Asn
            675             680             685

Leu Pro Lys Lys Ile Ile Phe Val Gly His Asp Trp Gly Ala Cys Leu
            690             695             700

Ala Phe His Tyr Ser Tyr Glu His Gln Asp Lys Ile Lys Ala Ile Val
705             710             715             720

His Ala Glu Ser Val Val Asp Val Ile Glu Ser Trp Asp Glu Trp Pro
            725             730             735

Asp Ile Glu Glu Asp Ile Ala Leu Ile Lys Ser Glu Glu Gly Glu Lys
            740             745             750

Met Val Leu Glu Asn Asn Phe Phe Val Glu Thr Met Leu Pro Ser Lys
            755             760             765

Ile Met Arg Lys Leu Glu Pro Glu Glu Phe Ala Ala Tyr Leu Glu Pro
            770             775             780

Phe Lys Glu Lys Gly Glu Val Arg Arg Pro Thr Leu Ser Trp Pro Arg
785             790             795             800

Glu Ile Pro Leu Val Lys Gly Gly Lys Pro Asp Val Val Gln Ile Val
            805             810             815

Arg Asn Tyr Asn Ala Tyr Leu Arg Ala Ser Asp Asp Leu Pro Lys Met
            820             825             830

Phe Ile Glu Ser Asp Pro Gly Phe Phe Ser Asn Ala Ile Val Glu Gly
            835             840             845

Ala Lys Lys Phe Pro Asn Thr Glu Phe Val Lys Val Lys Gly Leu His
            850             855             860

Phe Ser Gln Glu Asp Ala Pro Asp Glu Met Gly Lys Tyr Ile Lys Ser
865             870             875             880

Phe Val Glu Arg Val Leu Lys Asn Glu Gln
            885             890

<210> SEQ ID NO 55
<211> LENGTH: 1389
<212> TYPE: DNA
<213> ORGANISM: Mus musculus
```

<400> SEQUENCE: 55

```
atgggctacc catacgacgt cccagactac gccagcatgg gctcactgca gccggatgcc      60
ggcaacagca gctggaacgg gaccgaagcg cccggaggcg gcacccgagc cacccctttac   120
tccctgcagg tgacactgac gctggtttgc ctggctggcc tgctcatgct gttcacagta    180
tttggcaacg tgctggttat tatcgcggtg ttcaccagtc gcgcgctcaa agctccccaa    240
aacctcttcc tggtgtccct ggcctcagcg gacatcctgg tggccacgct ggtcattccc    300
ttttctttgg ccaacgaggt tatgggttac tggtactttg gtaaggtgtg gtgtgagatc    360
tatttggctc tcgacgtgct cttttgcacg tcgtccatag tgcacctgtg cgccatcagc    420
cttgaccgct actggtccat cacgcaggcc atcgagtaca acctgaagcg cacgccgcgt    480
cgcatcaagg ccatcattgt caccgtgtgg gtcatctcgg ctgtcatctc cttcccgcca    540
ctcatctcca tagagaagaa gggcgctggc ggcgggcagc agccggccga gccaagctgc    600
aagatcaacg accagaagtg gtatgtcatc tcctcgtcca tcggttcctt cttcgcgcct    660
tgcctcatca tgatcctggt ctacgtgcgt atttaccaga tcgccaagcg tcgcacccgg    720
tgcctcccag ccgccggggt ccggacgcct cgttccgcgc cgccgggggg cgccgatcgc    780
aggcccaacg ggctgggccc ggagcgcggc gcgggtccca cgggcgctga ggcggagccg    840
ctgcccaccc agcttaacgg tgccccgggg gagcccgcgc ccgccgggcc ccgcgatggg    900
gatgcgctgg acctagagga gagttcgtcg tccgagcacg ccgagcggcc cccggggccc    960
cgcagacccg accgcggccc ccgagccaag ggcaagaccc gggcgagtca ggtgaagccg   1020
ggggacagtc tgccgcggcg cgggcccggg gccgcggggc cggggggcttc ggggtccggg   1080
cacggagagg agcgcggcgg gggcgccaaa gcgtcgcgct ggcgcgggag gcaaaaccgg   1140
gagaaacgct tcacgttcgt gctggcggtg gtgatcggcg tgttcgtggt gtgttggttt   1200
ccgttctttt tcacctacac gctcatagcg gtcggctgcc cggtgcccag ccagctcttc   1260
aacttcttct tctggttcgg ctactgcaac agctcgctga accctgttat ctacaccatc   1320
ttcaaccacg acttccgacg cgccttcaag aagatcctct gccgtgggga cagaaaacgc   1380
atcgtgtga                                                           1389
```

<210> SEQ ID NO 56
<211> LENGTH: 462
<212> TYPE: PRT
<213> ORGANISM: Mus musculus

<400> SEQUENCE: 56

```
Met Gly Tyr Pro Tyr Asp Val Pro Asp Tyr Ala Ser Met Gly Ser Leu
1               5                   10                  15

Gln Pro Asp Ala Gly Asn Ser Ser Trp Asn Gly Thr Glu Ala Pro Gly
            20                  25                  30

Gly Gly Thr Arg Ala Thr Pro Tyr Ser Leu Gln Val Thr Leu Thr Leu
        35                  40                  45

Val Cys Leu Ala Gly Leu Leu Met Leu Phe Thr Val Phe Gly Asn Val
    50                  55                  60

Leu Val Ile Ile Ala Val Phe Thr Ser Arg Ala Leu Lys Ala Pro Gln
65                  70                  75                  80

Asn Leu Phe Leu Val Ser Leu Ala Ser Ala Asp Ile Leu Val Ala Thr
                85                  90                  95

Leu Val Ile Pro Phe Ser Leu Ala Asn Glu Val Met Gly Tyr Trp Tyr
            100                 105                 110

Phe Gly Lys Val Trp Cys Glu Ile Tyr Leu Ala Leu Asp Val Leu Phe
```

-continued

```
            115                 120                 125
Cys Thr Ser Ser Ile Val His Leu Cys Ala Ile Ser Leu Asp Arg Tyr
            130                 135                 140

Trp Ser Ile Thr Gln Ala Ile Glu Tyr Asn Leu Lys Arg Thr Pro Arg
145                 150                 155                 160

Arg Ile Lys Ala Ile Ile Val Thr Val Trp Val Ile Ser Ala Val Ile
                    165                 170                 175

Ser Phe Pro Pro Leu Ile Ser Ile Glu Lys Lys Gly Ala Gly Gly Gly
                180                 185                 190

Gln Gln Pro Ala Glu Pro Ser Cys Lys Ile Asn Asp Gln Lys Trp Tyr
                195                 200                 205

Val Ile Ser Ser Ser Ile Gly Ser Phe Phe Ala Pro Cys Leu Ile Met
            210                 215                 220

Ile Leu Val Tyr Val Arg Ile Tyr Gln Ile Ala Lys Arg Arg Thr Arg
225                 230                 235                 240

Val Pro Pro Ser Arg Arg Gly Pro Asp Ala Cys Ser Ala Pro Pro Gly
                245                 250                 255

Gly Ala Asp Arg Arg Pro Asn Gly Leu Gly Pro Glu Arg Gly Ala Gly
                260                 265                 270

Pro Thr Gly Ala Glu Ala Glu Pro Leu Pro Thr Gln Leu Asn Gly Ala
            275                 280                 285

Pro Gly Glu Pro Ala Pro Ala Gly Pro Arg Asp Gly Asp Ala Leu Asp
            290                 295                 300

Leu Glu Glu Ser Ser Ser Ser Glu His Ala Glu Arg Pro Pro Gly Pro
305                 310                 315                 320

Arg Arg Pro Asp Arg Gly Pro Arg Ala Lys Gly Lys Thr Arg Ala Ser
                325                 330                 335

Gln Val Lys Pro Gly Asp Ser Leu Pro Arg Arg Gly Pro Gly Ala Ala
                340                 345                 350

Gly Pro Gly Ala Ser Gly Ser Gly His Gly Glu Glu Arg Gly Gly Gly
            355                 360                 365

Ala Lys Ala Ser Arg Trp Arg Gly Arg Gln Asn Arg Glu Lys Arg Phe
        370                 375                 380

Thr Phe Val Leu Ala Val Val Ile Gly Val Phe Val Val Cys Trp Phe
385                 390                 395                 400

Pro Phe Phe Phe Thr Tyr Thr Leu Ile Ala Val Gly Cys Pro Val Pro
                405                 410                 415

Ser Gln Leu Phe Asn Phe Phe Trp Phe Gly Tyr Cys Asn Ser Ser
                420                 425                 430

Leu Asn Pro Val Ile Tyr Thr Ile Phe Asn His Asp Phe Arg Arg Ala
            435                 440                 445

Phe Lys Lys Ile Leu Cys Arg Gly Asp Arg Lys Arg Ile Val
450                 455                 460
```

MEASURING G PROTEIN COUPLED RECEPTOR ACTIVATION

FIELD OF THE INVENTION

The present invention relates to methods and polypeptides for detecting a compound in a sample. In particular, the present invention relates to the use of a cell-free composition comprising at least one G protein coupled receptor embedded in a lipid bilayer which when expressed in a cell the N-terminus of the G protein coupled receptor, or subunits thereof, is outside the cell and the C-terminus is inside the cell, and which is capable of binding the compound. Optionally, the composition also comprises at least one accessory molecule that directly or indirectly binds an intracellular loop and/or the C-terminus of the G protein coupled receptor. The G protein coupled receptor, and/or accessory molecule when present, in combination comprise a bioluminescent protein and an acceptor molecule, which enables bioluminescent resonance energy transfer (BRET) to be used to detect the compound binding the receptor.

BACKGROUND OF THE INVENTION

G protein coupled receptors (GPCRs) are a family of transmembrane receptors that sense molecules outside the cell and activate inside signal transduction pathways and, ultimately, cellular responses. GPCRs are found only in eukaryotes including yeast and animals. The ligands that bind and activate GPCRs include light-sensitive compounds, odors, pheromones, hormones, and neurotransmitters, and vary in size from small molecules to peptides to large proteins. G protein-coupled receptors are involved in many diseases, and are also the target of therapeutic drugs.

Vertebrate and *C. elegans* odorant receptors (ORs) are members of the G-protein coupled receptor (GPCR) family (Buck et al., 1991; Troemel et al., 1995). GPCRs are characterised by their seven transmembrane spanning domains with ligand binding domains inferred to be on the extracellular side of the membrane and G-protein binding domains on the intracellular side. When a receptor binds the ligand, a conformational change occurs in the receptor allowing it to activate a heterotrimeric G-protein (Kobilka et al., 2007). The activated G-protein can then activate signal transduction pathways such as the guanyl cyclase or phospholipase C pathways, transducing the signal to higher processing centres (Gaillard et al., 2004).

Forster resonance energy transfer, or simply resonance energy transfer (RET), is the non-radiative transfer of energy from an excited state donor molecule to a ground state acceptor molecule (Ghanouni et al., 2001). Energy transfer efficiency is dependent on the distance between the donor and acceptor, the extent of the spectral overlap and the relative orientation of the acceptor and donor dipoles. Previous cases where intramolecular RET has been used to monitor GPCR activation have employed a fluorescent donor and acceptor, a method referred to as fluorescence resonance energy transfer (FRET). In most cases both the fluorescent donor and acceptor are engineered variants of green fluorescent protein (GFP) from *Aequoria victoria* (Tsien, 1998). The most widely used FRET pair is cyan fluorescent protein (CFP) as the donor alongside yellow fluorescent protein (YFP) as the acceptor (Piston and Kremers, 2007) and this FRET system has previously been used to quantify direct ligand binding by a number of GPCRs (Lohse et al., 2003 and 2007; Vilardaga et al., 2003; Rochais et al., 2007; Lisenbee et al., 2007).

One method for monitoring receptor activation involves dual labelling a single GPCR with CFP and YFP at insertion sites within the third intracellular loop and C-terminus, respectively. Excitation of CFP with light at 436 nm causes CFP emission at 480 nm and FRET to YFP, which emits at 535 nm. The efficiency of FRET varies with the sixth power of the distance between donor and acceptor, providing an exquisitively sensitive indication of conformational changes in the GPCR. This was demonstrated with α2AR, parathyroid hormone receptor (PTHR), β1-AR and secretin receptors in intact cells. Interaction of the agonists noreadrenaline with α2AR (Lohse et al., 2003), parathyroid hormone with PTHR (Vilardaga et al., 2003), norepinephrine with β1-AR (Rochais et al., 2007) and secretin with secretin receptors (Lisenbee et al., 2007) changed the distance between CFP and YFP thus causing a change in FRET signal.

Replacement of the YFP acceptor with F1AsH, a fluorescein arsenical hairpin binder, in a FRET system (Hoffman et al., 2005; Nakanishi et al., 2006) resulted in a five-fold greater increase in agonist-induced FRET signal compared with the CFP/YFP system when used to monitor α2-adrenergic receptor activation (Nakanishi et al., 2006). However, F1AsH involves a more difficult labelling and washing procedure which has limited use in the wider research community. The CFP/YFP system remains the most frequently reported FRET system for monitoring intramolecular conformational change. A major disadvantage associated with FRET is the need for a light source to energise the donor fluorophore (Piston and Kremers, 2007). This causes unwanted direct excitation of the acceptor at the donor excitation wavelength (a problem referred to as 'cross-talk").

In bioluminescence resonance energy transfer (BRET), the donor fluorophore of FRET is replaced with a luciferase and the acceptor can be any suitable fluorophore. The use of a luciferase avoids the need for illumination as the addition of a substrate initiates bioluminescent emission and hence, RET. Two common implementations of BRET comprise *Renilla* luciferase (RLuc) with either coelenterazine h (BRET[1]; $\lambda_{em}$=~475 nm) or coelenterazine 400a (Clz400a) substrate (BRET[2]; $\lambda_{em}$=~395 nm) as the donor system coupled to either of the GFP mutants, YFP (BRET[1]; $\lambda_{em}$=~530 nm) or GFP[2] (BRET[2]; $\lambda_{em}$=~510 nm). The BRET system offers superior spectral separation between the donor and acceptor emission peaks of ~115 nm compared to ~55 nm for the BRET[1] system at the expense of the quantum yield (Pfleger and Eidne et al., 2006).

FRET with odorant receptors has only previously been demonstrated for Class A (a₂-adrenergic and parathyroid hormone, (Vilardaga et al., 2003)) and Class B (secretin, (Lisenbee et al., 2007)) GPCRs. Unlike mammalian ORs, which belong to GPCR Class A, nematode ORs (Robertson, 1998 and 2001) belong to neither of these classes and are evolutionarily and structurally distinct. Furthermore, all ORs, including mammalian ORs, which sit within Class A of the GPCR superfamily, are atypical in respect of their expression. Generally these proteins cannot be functionally expressed other than in neurons derived from the chemosensory lineage. A number of accessory proteins have been identified whose presence is required for proper expression of mammalian and nematode ORs.

Thus, there is a need for suitably sensitive methods and molecules which enable the detection of compounds which bind G protein coupled receptors for use in, for example, biosensors.

SUMMARY OF THE INVENTION

The present inventors have surprisingly found that cell-free bioluminescence resonance energy transfer (BRET) using chimeric G protein coupled receptors (GPCRs), such as odorant receptors (ORs), to detect a target compound is more sensitive than other detection methods such as BRET using whole cells or FRET.

Thus, in a first aspect the present invention provides a method of detecting a compound, the method comprising,
  i) contacting a sample with a cell-free composition comprising
    a) at least one G protein coupled receptor embedded in a lipid bilayer, and which is capable of binding the compound, and
    b) optionally at least one accessory molecule that directly or indirectly binds an intracellular loop and/or the C-terminus of the G protein coupled receptor, wherein the G protein coupled receptor comprises one or more subunits that are the same or different, and wherein the G protein coupled receptor, and/or accessory molecule when present, in combination comprise a bioluminescent protein and an acceptor molecule,
  ii) simultaneously or sequentially with step i) providing a substrate of the bioluminescent protein, and allowing the bioluminescent protein to modify the substrate,
  iii) determining if step ii) modulates bioluminescent resonance energy transfer (BRET) between the bioluminescent protein and the acceptor molecule,
wherein the spatial location and/or dipole orientation of the bioluminescent protein relative to the acceptor molecule is altered when the compound binds the G protein coupled receptor, and wherein when expressed in a cell the N-terminus of the G protein coupled receptor, or subunits thereof, is outside the cell and the C-terminus inside the cell.

In one embodiment, a subunit of the G protein coupled receptor which is capable of binding the compound comprises
  i) the bioluminescent protein, and
  ii) the acceptor molecule,
and wherein the spatial location and/or dipole orientation of the bioluminescent protein relative to the acceptor molecule is altered when the compound binds the subunit. For example, the subunit may comprise
  i) an amino acid sequence provided as SEQ ID NO:13, 15, 52 or 54, or
  ii) an amino acid sequence which is at least 40% identical to any one or more of SEQ ID NO:13, 15, 52 or 54.

In an alternate embodiment, the G protein coupled receptor comprises
  i) a first subunit comprising
    a) the bioluminescent protein, and
    b) the acceptor molecule, and
  ii) a second subunit which is capable of binding the compound,
and wherein the spatial location and/or dipole orientation of the bioluminescent protein relative to the acceptor molecule is altered when the compound binds the second subunit.

In a further embodiment,
  i) the bioluminescent protein forms part of the third non-transmembrane loop of the subunit, and the acceptor molecule forms part of the fifth non-transmembrane loop, or
  ii) the acceptor molecule forms part of the third non-transmembrane loop of the subunit, and the bioluminescent protein forms part of the fifth non-transmembrane loop, or
  iii) the bioluminescent protein forms part of the first non-transmembrane loop of the subunit, and the acceptor molecule forms part of the third non-transmembrane loop, or
  iv) the acceptor molecule forms part of the first non-transmembrane loop of the subunit, and the bioluminescent protein forms part of the third non-transmembrane loop, or
  v) the bioluminescent protein forms part of the fifth non-transmembrane loop of the subunit, and the acceptor molecule forms part of the C-terminus, or
  vi) the acceptor molecule forms part of the fifth non-transmembrane loop of the subunit, and the bioluminescent protein forms part of the C-terminus.

In yet another alternate embodiment, the G protein coupled receptor comprises
  i) a first subunit comprising the bioluminescent protein, and
  ii) a second subunit comprising the acceptor molecule. For example, the first or second subunit may comprise:
    i) an amino acid sequence provided as SEQ ID NO: 17 or 19, or
    ii) an amino acid sequence which is at least 40% identical to SEQ ID NO: 17 and/or 19.

In an embodiment,
  i) the bioluminescent protein forms part of the third non-transmembrane loop of the first subunit, and the acceptor molecule forms part of the fifth non-transmembrane loop of the second subunit, or
  ii) the acceptor molecule forms part of the third non-transmembrane loop of the first subunit, and the bioluminescent protein forms part of the fifth non-transmembrane loop of the second subunit, or
  iii) the bioluminescent protein forms part of the first non-transmembrane loop of the first subunit, and the acceptor molecule forms part of the third non-transmembrane loop of the second subunit, or
  iv) the acceptor molecule forms part of the first non-transmembrane loop of the first subunit, and the bioluminescent protein forms part of the third non-transmembrane loop of the second subunit, or
  v) the bioluminescent protein forms part of the fifth non-transmembrane loop of the first subunit, and the acceptor molecule forms part of the C-terminus of the second subunit, or
  vi) the acceptor molecule forms part of the fifth non-transmembrane loop of the first subunit, and the bioluminescent protein forms part of the C-terminus of the second subunit.

In a further alternate embodiment,
  i) the G protein coupled receptor comprises a subunit comprising the bioluminescent protein, and the accessory molecule comprises the acceptor molecule, or
  ii) the G protein coupled receptor comprises a subunit comprising the acceptor molecule, and the accessory molecule comprises the bioluminescent protein.

In another alternate embodiment, the accessory molecule comprises
  i) the bioluminescent protein, and
  ii) the acceptor molecule.

In a further alternate embodiment, the composition comprises at least two accessory molecules, and wherein a first accessory molecule comprises the bioluminescent protein and a second accessory molecule comprises the acceptor molecule.

The present inventors were particularly surprised to find how superior the present invention is when compared to FRET-cellfree and BRET-whole cell detection systems. Thus, in a preferred embodiment, the method of the invention is at least 2 fold, 3 fold or 4 fold more sensitive than if a non-bioluminescent protein is used as a donor molecule and a modulation of fluorescence resonance energy transfer (FRET) is determined. In a further preferred embodiment, the method of the invention provides at least a 10 fold, 20 fold, 30 fold or 40 fold more intense BRET signal than if the method used the same G protein coupled receptor present in an intact cell instead of being in a cell-free composition.

Given the atypical nature of Class A GPCRs, ORs generally and nematode ORs in particular, it was surprising that a chimera comprising a Class A GPCR with BRET donor and acceptor tags would a) retain structural integrity and b) be capable of transducing receptor activation by an odorant into an optical signal. Thus, in a preferred embodiment, the G protein coupled receptor is a Class A GPCR. In a further preferred embodiment, the class A GPCR is an odorant receptor. The odorant receptor can be from any source as long as when expressed in a cell the N-terminus of the receptor is outside the cell and the C-terminus is inside the cell. Examples include, but are not limited to, a chordate receptor, a nematode receptor, or a biologically active variant or fragment of any one thereof. Examples of chordate receptors include, but are not limited to mammalian receptors, avian receptors and fish receptors. In a preferred embodiment, the odorant receptor is a nematode receptor or biologically active variant or fragment thereof. In an embodiment, the nematode receptor is a *Caenorhabditis elegans* receptor, or biologically active variant or fragment thereof.

In an embodiment, the odorant receptor comprises:
  i) an amino acid sequence as provided in any one of SEQ ID NOs 1 to 6, and
  ii) an amino acid sequence which is at least 40% identical to any one or more of SEQ ID NO:1 to 6.

In another embodiment, the subunit is a chimera of a portion of two or more different G protein coupled receptor subunits.

The accessory molecule can be any molecule that directly or indirectly associates with the G protein coupled receptor. Examples include, but are not limited to, G protein and arrestin.

The effect of changing compound concentrations on the amplitude of the change in BRET has provided the first demonstration that the response is dose-dependent. Thus, in a preferred embodiment the level of BRET is indicative of the relative amount of the compound in the sample.

Examples of bioluminescent proteins include, but are not limited to, a luciferase, a β-galactosidase, a lactamase, a horseradish peroxidase, an alkaline phophatase, a β-glucuronidase or a β-glucosidase.

Examples of luciferases include, but are not limited to, a *Renilla* luciferase, a Firefly luciferase, a Coelenterate luciferase, a North American glow worm luciferase, a click beetle luciferase, a railroad worm luciferase, a bacterial luciferase, a *Gaussia* luciferase, Aequorin, a *Arachnocampa* luciferase, or a biologically active variant or fragment of any one, or chimera of two or more, thereof.

Examples of substrates include, but are not limited to, beetle luciferin, other luciferins, coelenterazine, or a derivative of coelenterazine. Also, in the case of some luminescent proteins such as aequorin, the substrate may be a cofactor such as calcium ions.

In one embodiment, the acceptor molecule is a protein, examples of which include, but are not limited to, green fluorescent protein (GFP), blue fluorescent variant of GFP (BFP), cyan fluorescent variant of GFP(CFP), yellow fluorescent variant of GFP (YFP), enhanced GFP (EGFP), enhanced CFP (ECFP), enhanced YFP (EYFP), GFPS65T, Emerald, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pocilloporin, *Renilla* GFP, Monster GFP, paGFP, Kaede protein or a Phycobiliprotein, or a biologically active variant or fragment of any one thereof.

In an alternate embodiment, the acceptor molecule is a non-protein, examples of which include, but are not limited to, an Alexa Fluor dye, Bodipy dye, Cy dye, fluorescein, dansyl, umbelliferone, fluorescent microsphere, luminescent microsphere, fluorescent nanocrystal, Marina Blue, Cascade Blue, Cascade Yellow, Pacific Blue, Oregon Green, Tetramethylrhodamine, Rhodamine, Texas Red, rare earth element chelates, or any combination or derivatives thereof.

In another embodiment, the methods further comprise simultaneously or sequentially with step i) or step ii) providing a co-factor of the bioluminescent protein. Examples include, but are not limited to, ATP, magnesium, oxygen, $FMNH_2$, calcium, or a combination of any two or more thereof.

In an embodiment, the cell-free composition was obtained by producing the G protein coupled receptor in a recombinant cell and disrupting the membrane of the cell.

In an embodiment, the recombinant cell does not produce any non-endogenous proteins which associate with the G protein coupled receptor.

The cell from which the cell-free composition can be obtained is any cell type capable of expressing the G protein coupled receptor and incorporating the receptor into its cell membrane. In a particularly preferred embodiment, the recombinant cell is a yeast cell.

In an alternate embodiment, the G protein coupled receptor is embedded in the lipid bilayer of a liposome.

In a further embodiment, the method is preformed using microfluidics.

In another aspect, the present invention provides a purified and/or recombinant polypeptide for detecting a compound, the polypeptide comprising,
  i) a subunit of a G protein coupled receptor, and
  ii) a bioluminescent protein and/or an acceptor molecule, wherein when expressed in a cell the N-terminus of the subunit is outside the cell and the C-terminus inside the cell.

In an embodiment, the polypeptide forms part of a protein complex which is a G protein coupled receptor comprising one or more different G protein coupled receptor subunits, and optionally one or more different accessory molecules.

In an embodiment,
  i) the bioluminescent protein forms part of the third non-transmembrane loop of the subunit, and the acceptor molecule forms part of the fifth non-transmembrane loop, or
  ii) the acceptor molecule forms part of the third non-transmembrane loop of the subunit, and the bioluminescent protein forms part of the fifth non-transmembrane loop, or
  iii) the bioluminescent protein forms part of the first non-transmembrane loop of the subunit, and the acceptor molecule forms part of the third non-transmembrane loop, or
  iv) the acceptor molecule forms part of the first non-transmembrane loop of the subunit, and the bioluminescent protein forms part of the third non-transmembrane loop, or
  v) the bioluminescent protein forms part of the fifth non-transmembrane loop of the subunit, and the acceptor molecule forms part of the C-terminus, or
  vi) the acceptor molecule forms part of the fifth non-transmembrane loop of the subunit, and the bioluminescent protein forms part of the C-terminus, or vii) the bioluminescent protein or the acceptor molecule forms part of the first non-transmembrane loop of the subunit, or
  viii) the bioluminescent protein or the acceptor molecule forms part of the third non-transmembrane loop of the subunit, or
  ix) the bioluminescent protein or the acceptor molecule forms part of the fifth non-transmembrane loop of the subunit, or x) the bioluminescent protein or the acceptor molecule forms part of the C-terminus of the subunit.

In a further embodiment, the polypeptide comprises the bioluminescent protein and the acceptor molecule, and wherein the spatial location and/or dipole orientation of the bioluminescent protein relative to the acceptor molecule is altered when the compound binds the polypeptide.

In an alternate embodiment, the polypeptide comprises the subunit and the bioluminescent protein, and the polypeptide is directly or indirectly bound to a second polypeptide comprising an acceptor molecule, and wherein the spatial location and/or dipole orientation of the bioluminescent protein relative to the acceptor molecule is altered when the compound binds the polypeptide and/or the second polypeptide.

In a further alternate embodiment, the polypeptide comprises the subunit and the acceptor molecule, and the polypeptide is directly or indirectly bound to a second polypeptide comprising a bioluminescent protein, and wherein the spatial location and/or dipole orientation of the bioluminescent protein relative to the acceptor molecule is altered when the compound binds the polypeptide and/or the second polypeptide.

In the above two embodiments, the second polypeptide either comprises an G protein coupled receptor subunit (to form a homo- or hetero-dimer or higher multimer as defined herein) or an accessory molecule.

In a further aspect, the present invention provides a purified and/or recombinant polypeptide for detecting a compound, the polypeptide comprising,
  i) an accessory molecule that directly or indirectly binds an intracellular loop and/or the C-terminus of the G protein coupled receptor, and
  ii) a bioluminescent protein and/or an acceptor molecule,
wherein when expressed in a cell the N-terminus of the G protein coupled receptor, or subunits thereof, is outside the cell and the C-terminus inside the cell.

As the skilled reader will appreciate, many of the above embodiments relating to the methods of detection also apply to the polypeptide aspects of the invention.

Also provided is an isolated and/or exogenous polynucleotide encoding a polypeptide of the invention.

In an embodiment, the polynucleotide comprises:
  i) a nucleotide sequence as provided in any one of SEQ ID NO's 7 to 12, 14, 16, 18, 20, 51 or 53, or
  ii) a nucleotide sequence which is at least 40% identical to any one or more of SEQ ID NO's 7 to 12, 14, 16, 18, 20, 51 or 53.

In another aspect, provided is a vector comprising a polynucleotide of the invention. In a preferred embodiment, the polynucleotide is operably linked to a promoter.

In a further aspect, provided is a host cell comprising the polynucleotide of the invention and/or the vector of the invention.

Preferably, the host cell produces, and hence comprises, a polypeptide of the invention.

The host cell can be any cell type.

The present inventors are also the first to show the functional expression of a nematode odorant receptor, which are evolutionarily different to mammalian odorant receptors, in yeast membranes. Thus, in a preferred embodiment the host cell is a yeast cell.

In a further aspect, the present invention provides a composition comprising the polypeptide of the invention, the polynucleotide of the invention, the vector of the invention, and/or the host cell of the invention.

Preferably, the polypeptide is embedded in a lipid bilayer.

Also provided is a cell-free composition comprising,
  i) the polypeptide of the invention comprising a G protein coupled receptor subunit, wherein the polypeptide is embedded in a lipid bilayer, and/or
  ii) the polypeptide of the invention comprising an accessory molecule which is directly or indirectly bound to an intracellular loop and/or the C-terminus of a G protein coupled receptor, wherein the G protein coupled receptor is embedded in a lipid bilayer, and wherein when expressed in a cell the N-terminus of the G protein coupled receptor, or subunits thereof, is outside the cell and the C-terminus inside the cell.

Preferably, the lipid bilayer is a yeast lipid bilayer.

In an embodiment, the cell-free composition further comprises a substrate of the bioluminescent protein and/or a co-factor of the bioluminescent protein.

As the skilled reader will appreciate, many of the above embodiments relating to the methods of detection also apply to the cell-free aspect of the invention.

In a further aspect, the present invention provides a method of producing a cell-free composition of the invention, the method comprising obtaining a cell of the invention and disrupting the membrane of the cells.

In an embodiment, the cells are permeabilized or lysed.

In an embodiment, the cells are lysed in a French press.

In another aspect, the present invention provides a biosensor comprising a polypeptide of the invention, a host cell of the invention, a composition of the invention and/or a cell-free composition of the invention.

In a further aspect, the present invention provides a method for screening for a compound that binds a G protein coupled receptor, the method comprising,
  i) contacting a candidate compound with a cell-free composition comprising
    a) at least one G protein coupled receptor embedded in a lipid bilayer, and which is capable of binding the compound, and
    b) optionally at least one accessory molecule that directly or indirectly binds an intracellular loop and/or the C-terminus of the G protein coupled receptor, wherein the G protein coupled receptor comprises one or more subunits that are the same or different, and wherein the G protein coupled receptor, and/or accessory molecule when present, in combination comprise a bioluminescent protein and an acceptor molecule,
  ii) simultaneously or sequentially with step i) providing a substrate of the bioluminescent protein, and allowing the bioluminescent protein to modify the substrate,
  iii) determining if step ii) modulates bioluminescent resonance energy transfer (BRET) between the bioluminescent protein and the acceptor molecule,
wherein a modulation of BRET indicates that the compound binds the G protein coupled receptor, and wherein when expressed in a cell the N-terminus of the G protein coupled receptor, or subunits thereof, is outside the cell and the C-terminus inside the cell.

As the skilled reader will appreciate, many of the above embodiments relating to the methods of detection also apply to the method of screening aspect of the invention.

In a further aspect, the present invention provides a kit comprising a polypeptide of the invention, a polynucleotide of the invention, a vector of the invention, a host cell of the invention, a composition of the invention, a cell-free composition of the invention, and/or a biosensor of the invention.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Principle of resonance energy transfer in ODR-10 receptor fused to $GFP^2$ and RLuc. $GFP^2$ is inserted in the third intracellular loop of the GPCR and RLuc to the C-terminus Diacetyl binding could result in a conformational change resulting in a decrease (top right), or increase (bottom right), in the distance between RLuc and $GFP^2$ or a change in the relative orientations of their chromophore dipoles, which would alter the $BRET^2$ signal in a dose-dependent manner.

Figure 2:
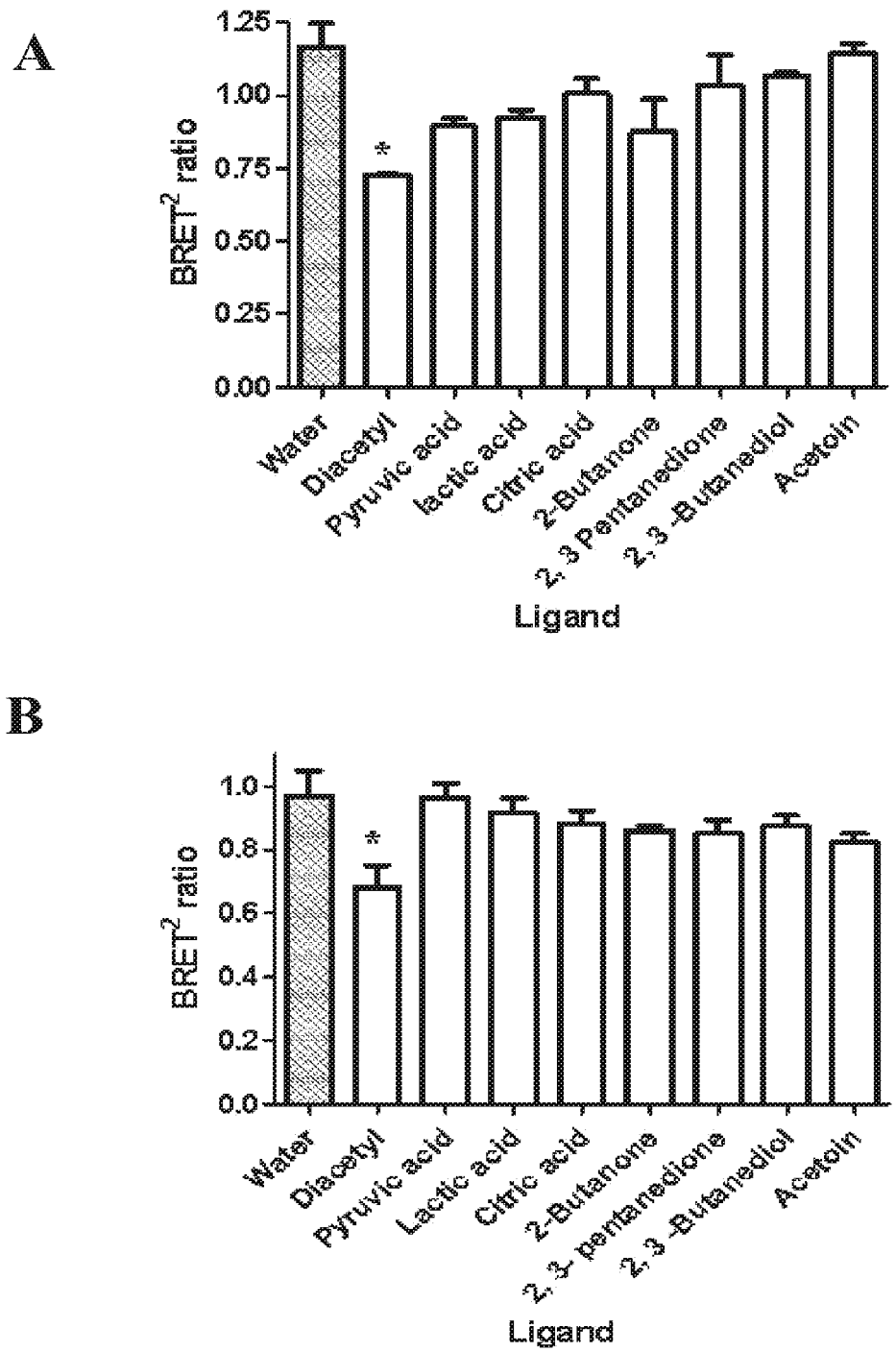

FIG. 2. The response of OGOR to (A) μM (mean±SEM, n=2) and (B) nM (mean±SEM, n=6) concentration of ligand or water (* denotes a significant different ($P \leq 0.05$) compared to water).

Figure 3:
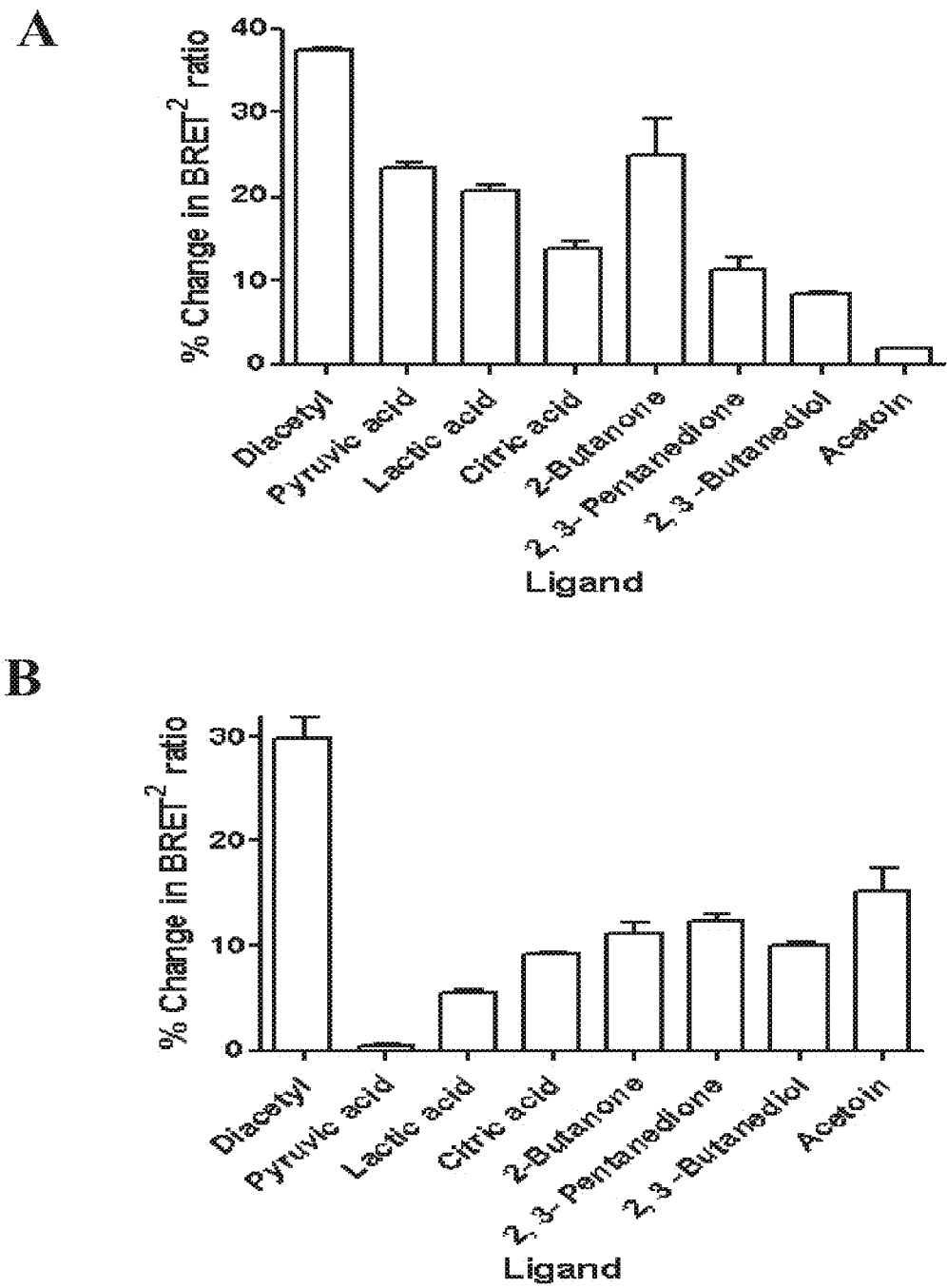

FIG. 3. The change in $BRET^2$ ratio (%) of OGOR to (A) μM (mean±SEM, n=2) and (B) nM (mean±SEM, n=6) concentration of ligand compared to water alone.

Figure 4:
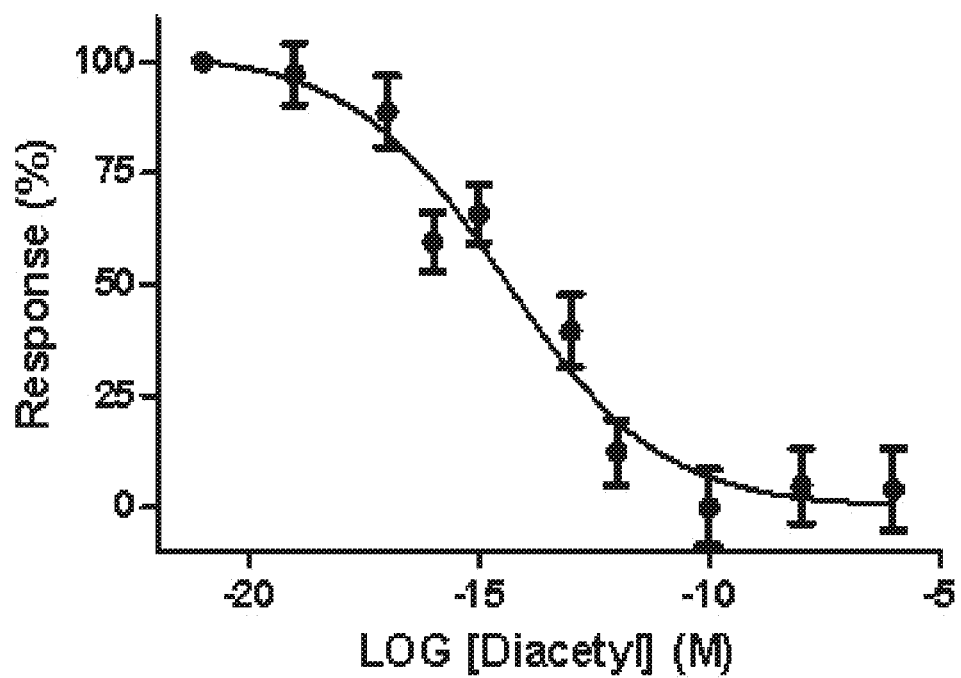

FIG. 4. Diacetyl concentration dependence of the OGOR $BRET^2$ response (mean±SEM, n=12)

Figure 5:
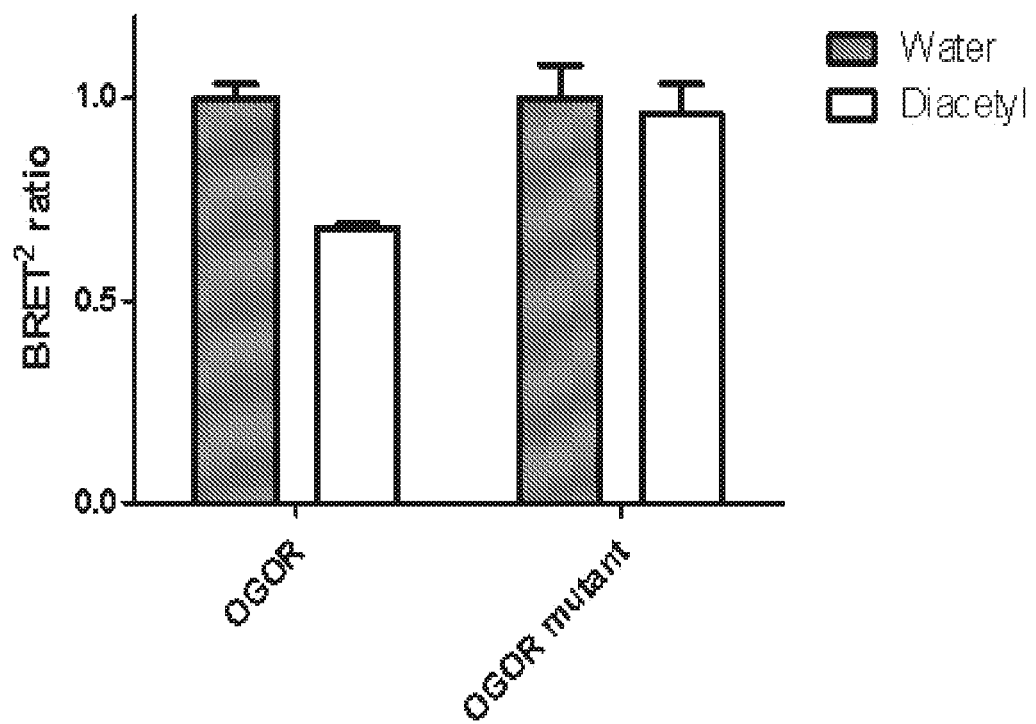

FIG. 5. Comparison of the response of OGOR (mean±SEM, n=3) and the OGOR mutant (mean±SEM, n=6) to water or one μM of diacetyl in water.

Figure 6:
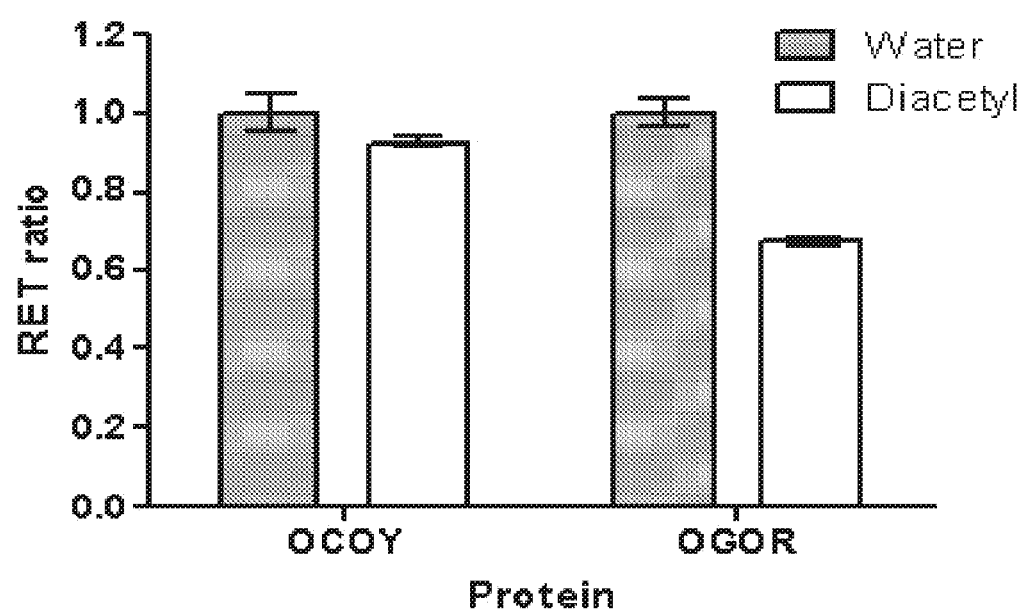

FIG. 6. Comparison of the response of OCOY (mean±SEM, n=5) and OGOR (mean±SEM, n=3) to water or one μM of diacetyl in water.

Figure 7:
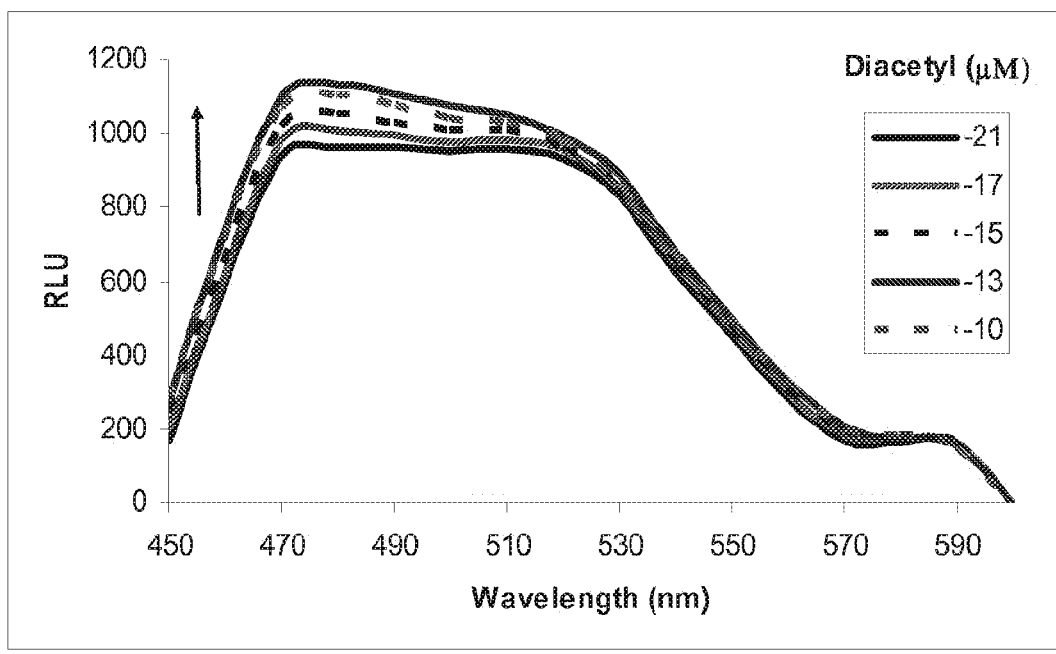
Figure 7:
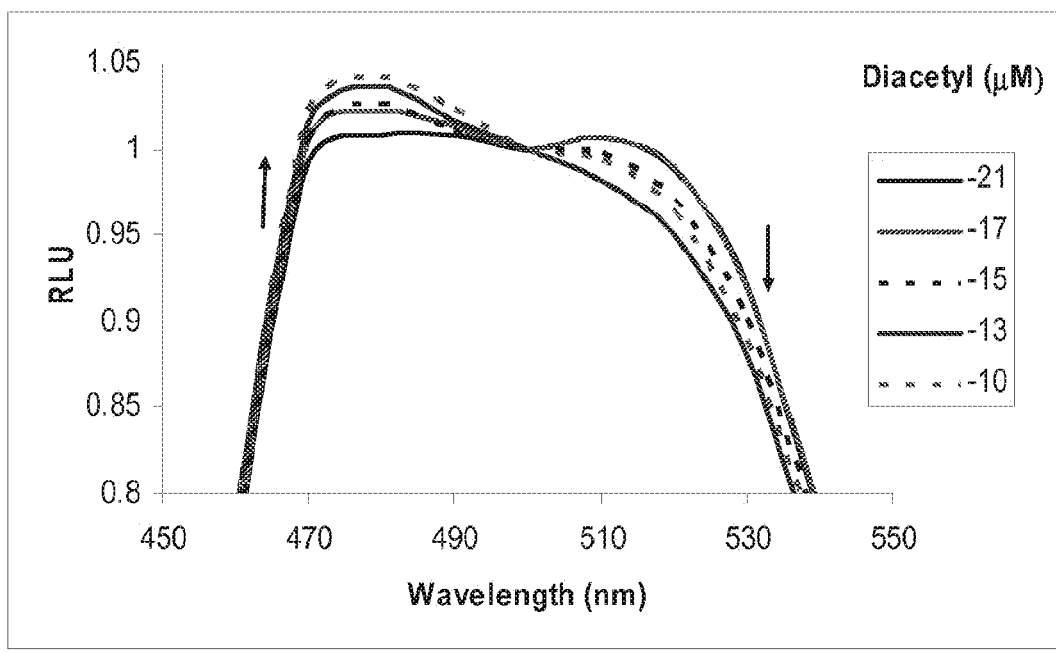

FIG. 7. Spectral scans of OCOY upon the addition of different concentrations of diacetyl. Top: Raw data. Bottom: Normalized (500 nm) data.

Figure 8:
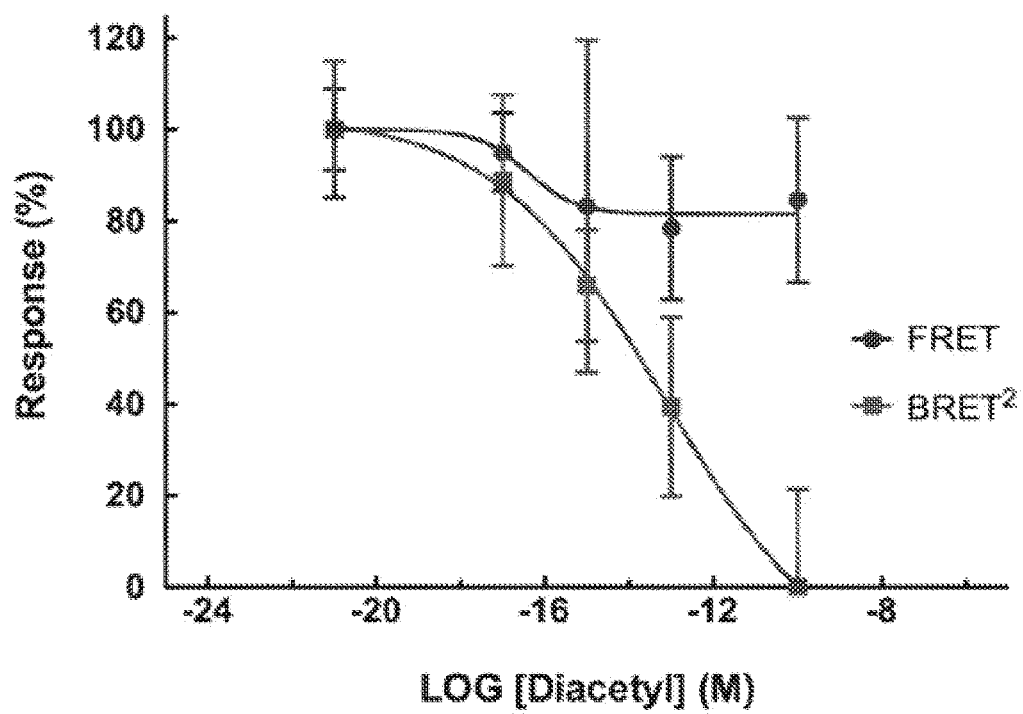

FIG. 8. Normalized dose response curve for ODR-10 tagged with both FRET (mean±SEM, n=5) and $BRET^2$ (mean±SEM, n=12).

Figure 9:
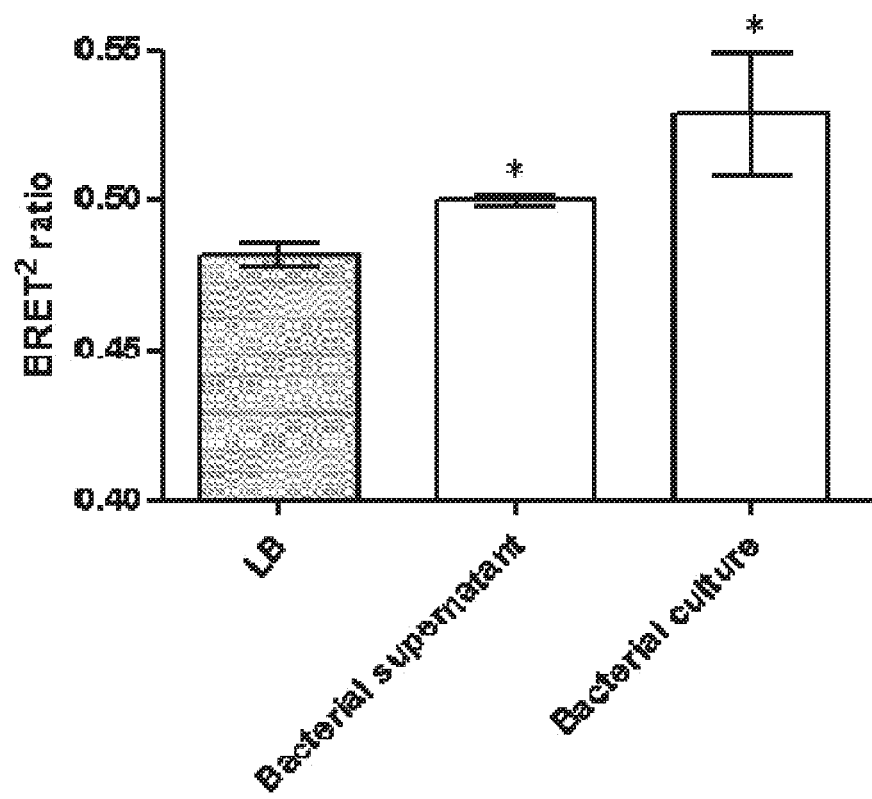

FIG. 9. The response of TGTR to 10 μL (mean±SD, n=3) of OP50 bacterial supernatant (LB) or OP50 bacterial culture in LB compared to LB alone (* denotes a significant different ($P \leq 0.05$) compared to LB).

Figure 10:
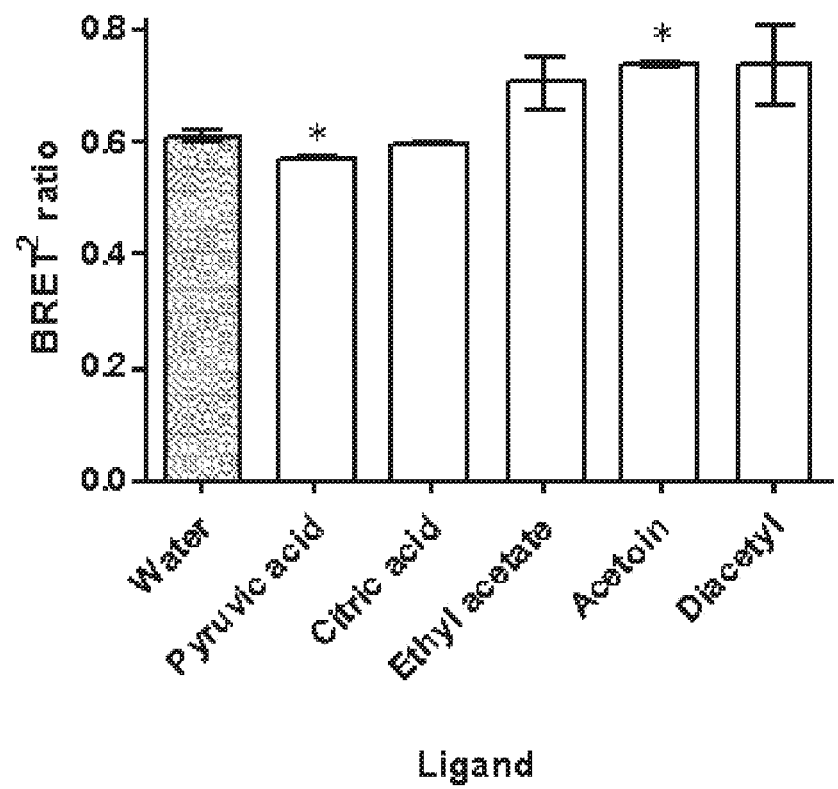

FIG. 10. The response of TGTR to μM (mean±SD, n=3) concentration of ligand or water (* denotes a significant different ($P \leq 0.05$) compared to water).

Figure 11:
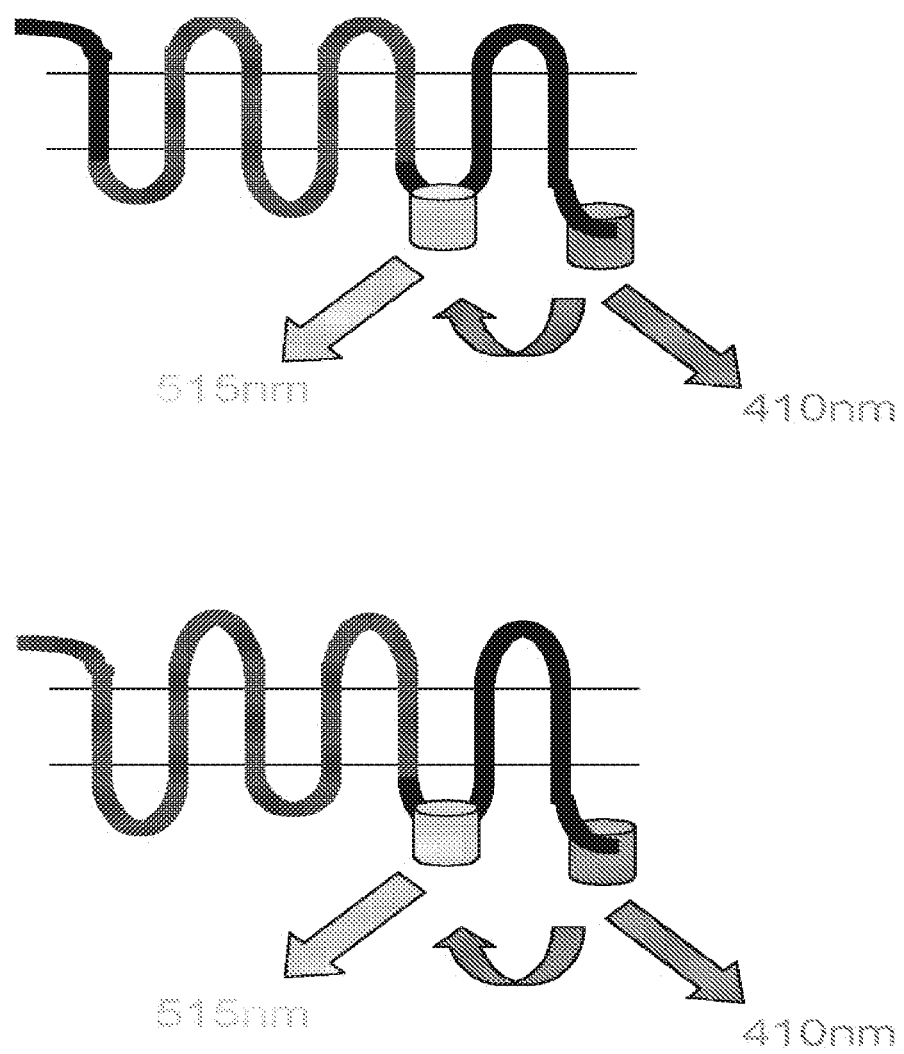

FIG. 11. ODR-10 transduction cassette. Dark—ODR-10 sequence, Light—variable receptor ligand binding domains. A) N-terminal fixed in cassette, B) N-terminal variable OR sequence. Rluciferase denoted as emitting at 410 nm, and $GFP^2$ denoted as emitting at 515 nm.

Figure 12:
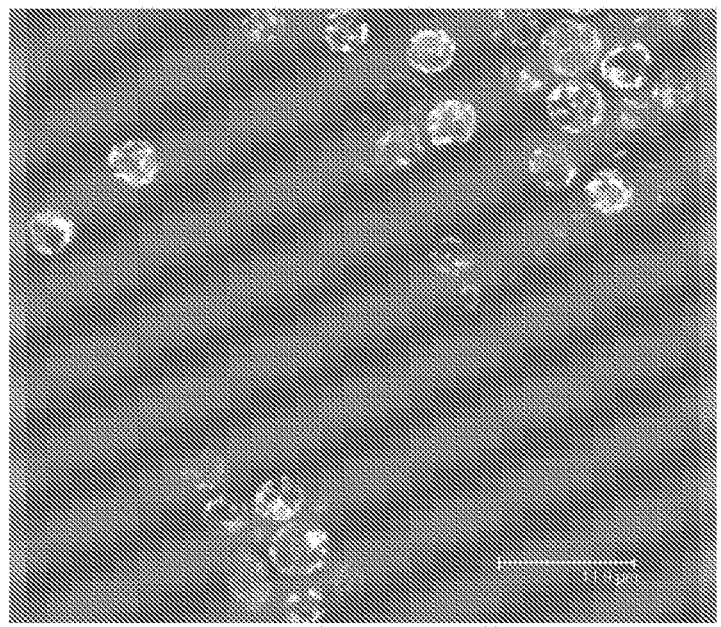

FIG. 12. Co-expressed odr-10-Rluc and odr-10-$GFP^2$ yeast cells to show odr-10 receptor localization and tagged odr-10 expression level by confocal microscopy (Ex488 nm, Leica SP2 confocal laser scanning microscope).

Figure 13:
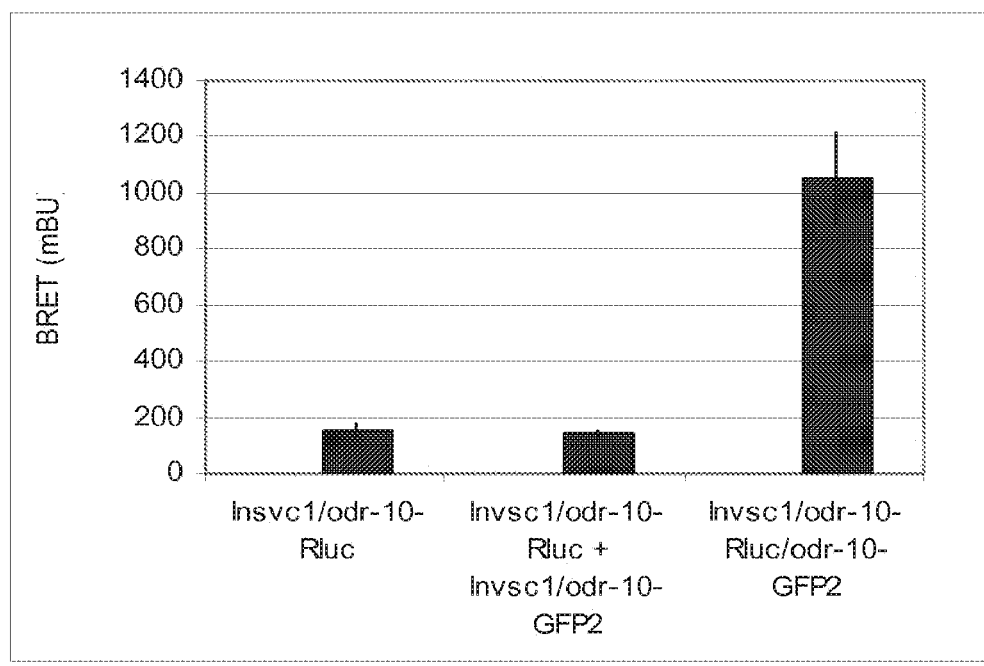

FIG. 13. Constitutive $BRET^2$ of nematode odr-10 in living Invsc1yeast cells. All tested yeast strains were induced for expressing tagged odr-10 proteins for 24 hours at 15° C. Energy transfer measurements were performed in living cells by adding 10 uM coelenterazine h (DeepBlueC) and measuring light emissions in a dual wavelength microplate reader with Rluc and GFP2 filter settings as described in the method. Data are means±StD of two independent experiments.

Insvc1/odr-10-RLuc—negative control.

Invsc1/odr-10-RLuc+Invsc1/odr-10-GFP2—OR and OG in separate cells. Cells mixed together for plate reading—BRET is not expected because the two constructs were expressed in separate cells.

Invsc1/odr-10-RLuc; odr-10-GFP2—both constructs expressed in same cell. BRET is present, therefore dimerisation is occurring.

Figure 14:
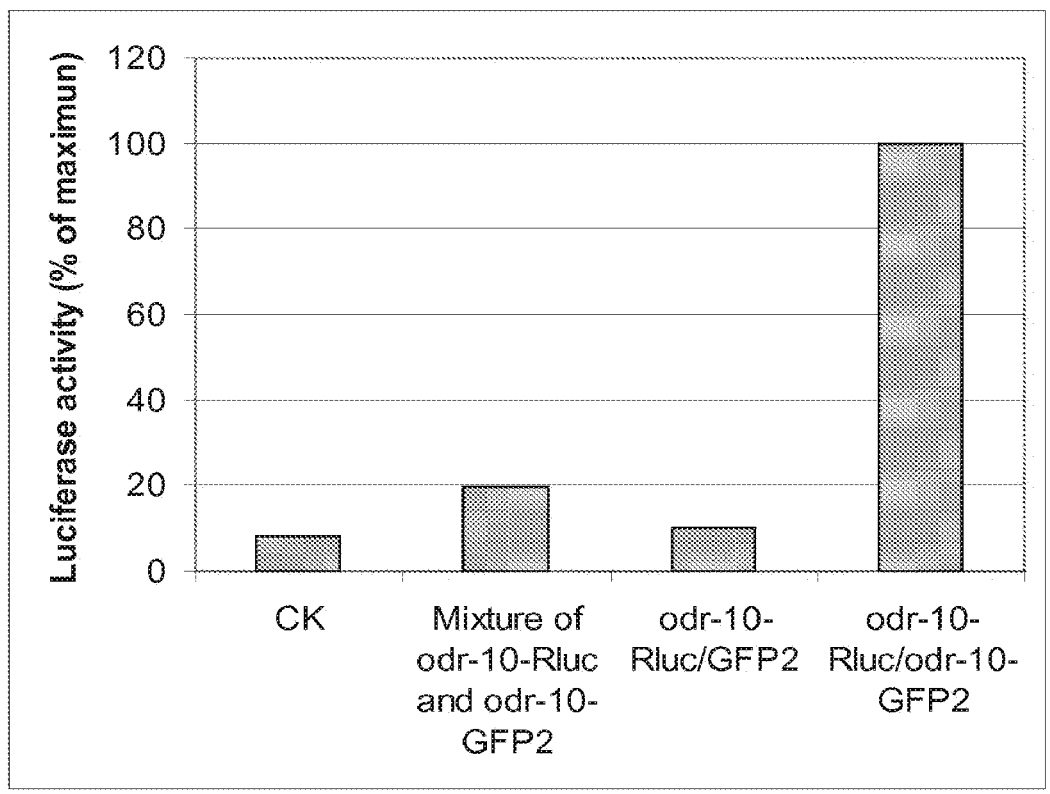

FIG. 14. Detection of Odr-10 oligomers by immunoprecipitation. Crude membrane from Invsc1 yeast cells co-expressing the indicated receptors were solubilised and adjusted to the same amount of luciferase activity. Receptors were then immunoprecipitated with anti-GFP antibody and luciferase activity determined in precipitates. Values are presented as % of maximal amount of precipitated luciferase activity. Data are mean of two biological repeats.

Figure 15:
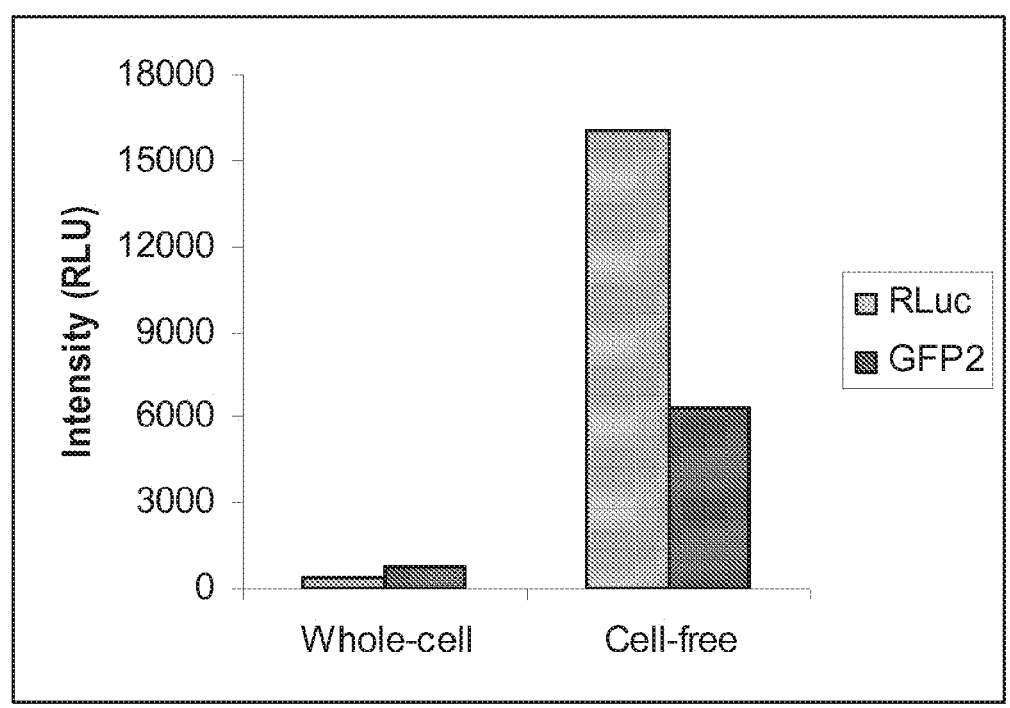

FIG. 15. Measured light output in the $BRET^2$ channels upon the addition of 5 μM of coelenterazine 400a to 100 μL, of a whole-cell assay sample of 100 μL, of the cell-free membrane preparations following ultracentrifugation.

Figure 16:
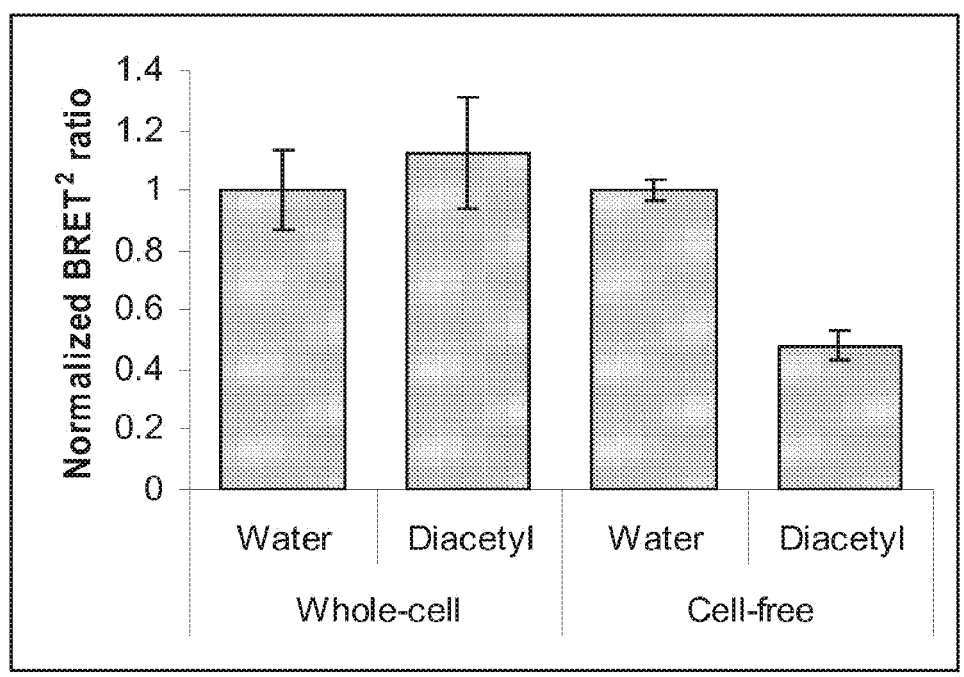

FIG. 16. $BRET^2$ signal upon incubation (45 minutes) with 1 μM of diacetyl (mean±S.D., n=3) monitored using a whole-cell and cell-free assay systems.

KEY TO THE SEQUENCE LISTING

SEQ ID NO:1—*C. elegans* Odr10 receptor.
SEQ ID NO:2—*C. elegans* Str112 receptor.
SEQ ID NO:3—*C. elegans* Str113 receptor.
SEQ ID NO:4—*C. elegans* Str114 receptor.
SEQ ID NO:5—*C. elegans* Str115 receptor.
SEQ ID NO:6—*C. elegans* Str116 receptor.
SEQ ID NO:7—ORF encoding *C. elegans* Odr10 receptor.
SEQ ID NO:8—ORF encoding *C. elegans* Str112 receptor.
SEQ ID NO:9—ORF encoding *C. elegans* Str113 receptor.
SEQ ID NO:10—ORF encoding *C. elegans* Str114 receptor.
SEQ ID NO:11—ORF encoding *C. elegans* Str115 receptor.
SEQ ID NO:12—ORF encoding *C. elegans* Str116 receptor.
SEQ ID NO:13—Polypeptide of the invention comprising *C. elegans* Odr10 receptor, RLuc inserted into the third intracellular loop (fifth non-transmembrane loop) and GFP inserted at the C-terminus.
SEQ ID NO:14—Open reading frame encoding polypeptide of the invention comprising *C. elegans* Odr10 receptor, RLuc inserted into the third intracellular loop (fifth non-transmembrane loop) and GFP inserted at the C-terminus
SEQ ID NO:15—Polypeptide of the invention comprising *C. elegans* Odr10 receptor, GFP inserted into the third intracellular loop (fifth non-transmembrane loop) and RLuc inserted at the C-terminus.
SEQ ID NO:16—Open reading frame encoding polypeptide of the invention comprising *C. elegans* Odr10 receptor, GFP inserted into the third intracellular loop (fifth non-transmembrane loop) and RLuc inserted at the C-terminus.
SEQ ID NO:17—Polypeptide of the invention comprising *C. elegans* Odr10 receptor and RLuc inserted at the C-terminus.
SEQ ID NO:18—Open reading frame encoding polypeptide of the invention comprising *C. elegans* Odr10 receptor RLuc inserted at the C-terminus.
SEQ ID NO:19—Polypeptide of the invention comprising *C. elegans* Odr10 receptor and GFP2 inserted at the C-terminus SEQ ID NO:20—Open reading frame encoding polypeptide of the invention comprising *C. elegans* Odr10 receptor GFP2 inserted at the C-terminus.
SEQ ID NO's 21 to 44—Oligonucleotide primers.
SEQ ID NO:45—mCitrine derivative.
SEQ ID NO:46—mCFP derivative.
SEQ ID NO:47—Open reading frame encoding mCitrine derivative.
SEQ ID NO:48—Open reading frame encoding mCFP derivative.
SEQ ID NO:49—Open reading frame encoding Odr10 FRET dual labelled fusion protein.
SEQ ID NO:50—Odr10 FRET dual labelled fusion protein.
SEQ ID NO:51—Open reading frame encoding Str112 BRET dual labelled fusion protein.
SEQ ID NO:52—Str112 BRET dual labelled fusion protein.
SEQ ID NO:53—Open reading frame encoding mouse $\alpha_{2A}$ adrenergic receptor BRET dual labelled fusion protein.
SEQ ID NO:54—Mouse $\alpha_{2A}$ adrenergic receptor BRET dual labelled fusion protein.
SEQ ID NO:55—Open reading frame encoding mouse $\alpha_{2A}$ adrenergic receptor.
SEQ ID NO:56—Mouse $\alpha_{2A}$ adrenergic receptor.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, biosensors, G-coupled protein receptor biology, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, unless specified otherwise, the term "G protein coupled receptor" refers to a seven transmembrane receptor which signals through G proteins. The receptor may be a single subunit, or two or more receptor subunits. When two or more receptor subunits are present they may be the same, different, or a combination thereof (for example, two of one subunit and a single of another subunit). Furthermore, unless specified or implied otherwise the terms "G protein coupled receptor" and "subunit of a G protein coupled receptor", or variations thereof, are used interchangeably.

As used herein, the term "odorant receptor", "olfactory receptor", "OR" or variations thereof refers to a polypeptide which, when present in a cell of an organism, is involved in chemosensory perception. In an embodiment, the cell is a neuron. Furthermore, the term "odorant receptor" or "olfactory receptor" refers to a polypeptide which binds an odorant ligand, or forms part of a protein complex that binds to an odorant ligand, resulting in a physiologic response.

As used herein, the term "bioluminescent protein" refers to any protein capable of acting on a suitable substrate to generate luminescence.

As used herein, the term "substrate" refers to any molecule that can be used in conjunction with a bioluminescent protein to generate or absorb luminescence.

As used herein, the phrase "allowing the bioluminescent protein to modify the substrate" refers to any enzymatic activity of the bioluminescent protein on the substrate that produces energy.

As used herein, the term "acceptor molecule" refers to any compound which can accept energy emitted as a result of the activity of a bioluminescent protein, and re-emit it as light energy.

As used herein, bioluminescent resonance energy transfer (BRET) is a proximity assay based on the non-radioactive transfer of energy between the bioluminescent protein donor and the acceptor molecule.

As used herein, the terms "modulate" or "modulation" or variations thereof refer to an alteration in the intensity and/or emission spectra of the bioluminescent protein and/or acceptor molecule.

As used herein, the term "spatial location" refers to the three dimensional positioning of the bioluminescent protein relative to the acceptor molecule which changes as a result of the compound binding a polypeptide defined herein comprising a G protein coupled receptor.

As used herein, the term "dipole orientation" refers to the direction in three-dimensional space of the dipole moment associated either with the bioluminescent protein and/or the acceptor molecule relative their orientation in three-dimensional space. The dipole moment is a consequence of a variation in electrical charge over a molecule.

As used herein, the term "more sensitive" refers to a greater change in resonance energy transfer ratio between the ligand unbound form to the ligand bound form of one reporter system (for example, BRET) to another reporter system (for example, FRET). As used herein, the term "cell free composition" refers to an isolated composition which contains few, if any, intact cells comprising the polypeptide of the invention. Examples of cell free compositions include cell extracts and compositions containing the isolated polypeptide comprising an odorant receptor. Preferably, the cell-free composition comprises no live cells, whether they comprise a polypeptide of the invention or not.

As used herein, the term "contacting" refers to the addition of a sample comprising, or which may comprise, the compound to be detected in a way that the compound is capable of binding the G protein coupled receptor.

As used herein, the term "lipid bilayer" refers to two layers of, typically amphiphilic, molecular arrays arranged opposite to each other with a common hydrophobic bilayer interior and two hydrophilic surfaces. The lipid bilayer can be naturally occurring or artificial. Most preferably, the lipid bilayer is a cellular or bio-membrane into which a polypeptide defined herein comprising an G protein coupled receptor is inserted, for example a mammalian, insect, plant or yeast cell membrane, most preferably of a yeast cell membrane.

As used herein, the term "yeast lipid bilayer" refers to the lipid bilayer being derived from a yeast cell expressing a polypeptide defined herein comprising an G protein coupled receptor. The skilled person can readily determine if a lipid bilayer is derived from a yeast by detecting proteins naturally occurring in yeast which are embedded in the membrane such as, but not limited to, Fus1p protein (Trueheart and Fink, 1989), SNARE complex which comprises the Sso1/2p, Sncip and Sec9p proteins (Strop et al., 2007), pheromone receptor Step 2p (Celic et al., 2003), and/or Alr1 (Graschopf et al., 2001).

As used herein, the term "simultaneously or sequentially" means that the substrate can be provided before, during or after the sample is contacted with a polypeptide as defined herein. Preferably, the substrate is provided at the same time or after the sample.

The "sample" can be any substance or composition suspected of comprising a compound to be detected. Examples of samples include air, liquid, biological material and soil. The sample may be obtained directly from the environment or source, or may be at least partially purified by a suitable procedure before a method of the invention is performed.

As used herein, the term "G protein coupled receptor, and/or accessory molecule when present, in combination comprise a bioluminescent protein and an acceptor molecule" means that the bioluminescent protein is associated, preferably covalently attached, more preferably produced as a fusion protein, with a subunit of the G protein coupled receptor or with an accessory molecule, and the acceptor molecule is associated, preferably covalently attached, more preferably produced as a fusion protein, with a subunit of the G protein coupled receptor or with an accessory molecule. The bioluminescent protein and accessory molecule may be associated, preferably covalently attached, more preferably produced as a fusion protein, with the same or different subunits of the G protein coupled receptor or the same or different accessory molecules. Furthermore, one of the bioluminescent protein and accessory molecule may be associated, preferably covalently attached, more preferably produced as a fusion protein, with a subunit of the G protein coupled receptor, and the other of the bioluminescent protein and accessory molecule may be associated with an accessory molecule. In addition, multiple bioluminescent protein and accessory molecule pairs may be present in the combination for multiplexing to detect different ligands, or increase the sensitivity of the detection of the same ligand.

As used herein, the term "forms part of" refers to the bioluminescent protein or acceptor molecule being located within the specified region of the G protein coupled receptor, or subunit thereof. This term also includes the possibility that the bioluminescent protein and/or acceptor molecule is attached to or binds the G protein coupled receptor but does not form a continuous chain of amino acids. In one embodiment, the bioluminescent protein or acceptor molecule completely replaces the specified region of the G protein coupled receptor. In another embodiment, some, but not all, of the specified region of the G protein coupled receptor is replaced. In yet another embodiment, none of the specified region of the G protein coupled receptor is replaced. As the skilled addressee will appreciate, the bioluminescent protein or acceptor molecule will not be inserted such that it makes the G protein coupled receptor portion of a polypeptide of the invention incapable of binding the target compound to result in a spatial change to the location and/or dipole orientation of the bioluminescent protein relative to the acceptor molecule.

As used herein, the term "at least a majority" of a specified portion (domain) of a G protein coupled receptor, refers to at least 51%, more preferably at least 75% and even more preferably at least 90% of the specified region.

By "substantially purified" or "purified" we mean a polypeptide that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. However, at present there is no evidence that the polypeptides of the invention exist in nature.

The term "recombinant" in the context of a polypeptide refers to the polypeptide when produced by a cell, or in a cell-free expression system, in an altered amount or at an altered rate compared to its native state. In one embodiment, the cell is a cell that does not naturally produce the polypeptide. However, the cell may be a cell which comprises a non-endogenous gene that causes an altered, preferably increased, amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, biologically active fragments, modifications, analogous and/or derivatives of the polypeptides described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

As used herein, a "biologically active fragment" is a portion of a polypeptide as described herein which maintains a defined activity of the full-length polypeptide. For example, a biologically active fragment of a G protein coupled receptor must be capable of binding the target compound resulting in a conformational change. Biologically active fragments can be any size as long as they maintain the defined activity. Preferably, biologically active fragments are at least 150, more preferably at least 250 amino acids in length.

As used herein, a "biologically active variant" is a molecule which differs from a naturally occurring and/or defined molecule by one or more amino acids but maintains a defined activity, such as defined above for biologically active fragments. Biologically active variants are typically least 50%, more preferably at least 80%, more preferably at least 90%, more preferably at least 95%, more preferably at least 97%, and even more preferably at least 99% identical to the naturally occurring and/or defined molecule.

With regard to a defined polypeptide or polynucleotide, it will be appreciated that % identity figures higher than those provided above will encompass preferred embodiments. Thus, where applicable, in light of the minimum % identity figures, it is preferred that the polypeptide or polynucleotide comprises an amino acid sequence which is at least 50%, more preferably at least 60%, more preferably at least 70%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

By an "isolated polynucleotide", including DNA, RNA, or a combination of these, single or double stranded, in the sense or antisense orientation or a combination of both, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated.

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

Furthermore, the term "polynucleotide" is used interchangeably herein with the term "nucleic acid". Polynucleotides of the present invention may possess, when compared to molecules provided herewith, one or more mutations which are deletions, insertions, or substitutions of nucleotide residues, or modified residues. Mutants can be either naturally occurring (that is to say, isolated from a natural source) or synthetic (for example, by performing site-directed mutagenesis on the nucleic acid). Usually, monomers of a polynucleotide are linked by phosphodiester bonds or analogs thereof. Analogs of phosphodiester linkages include: phosphorothioate, phosphorodithioate, phosphoroselenoate, phosphorodiselenoate, phosphoroanilothioate, phosphoranilidate and phosphoramidate.

Compositions of the present invention may include an "acceptable carrier". Examples of such acceptable carriers include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. The exact nature of the "acceptable carrier" will depend on the use of the composition. Considering the uses described herein, and the nature of the component of the invention in the composition, the skilled person can readily determine suitable a "acceptable carrier(s)" for a particular use.

Bioluminescent Proteins

It is understood in the art that a bioluminescent protein is an enzyme which converts a substrate into an activated product which then releases energy as it relaxes. The activated product (generated by the activity of the bioluminescent protein on the substrate) is the source of the bioluminescent protein-generated luminescence that is transferred to the acceptor molecule.

There are a number of different bioluminescent proteins that can be employed in this invention (see, for example, Table 1). Given the size of bioluminescent proteins it was surprising that functional polypeptides useful for the present invention could be produced. Light-emitting systems have been known and isolated from many luminescent organisms including bacteria, protozoa, coelenterates, molluscs, fish, millipedes, flies, fungi, worms, crustaceans, and beetles, particularly click beetles of genus *Pyrophorus* and the fireflies of the genera *Photinus, Photuris,* and *Luciola*. Additional organisms displaying bioluminescence are listed in WO 00/024878, WO 99/049019 and Viviani (2002).

One very well known example is the class of proteins known as luciferases which catalyze an energy-yielding chemical reaction in which a specific biochemical substance, a luciferin (a naturally occurring fluorophore), is oxidized by an enzyme having a luciferase activity (Hastings, 1996). A great diversity of organisms, both prokaryotic and eukaryotic, including species of bacteria, algae, fungi, insects, fish and other marine forms can emit light energy in this manner and each has specific luciferase activities and luciferins which are chemically distinct from those of other organisms. Luciferin/luciferase systems are very diverse in form, chemistry and function. Bioluminescent proteins with luciferase activity are thus available from a variety of sources or by a variety of means. Examples of bioluminescent proteins with luciferase activity may be found in U.S. Pat. Nos. 5,229,285, 5,219,737, 5,843,746, 5,196,524, and 5,670,356. Two of the most widely used luciferases are: (i) *Renilla* luciferase (from *R. reniformis*), a 35 kDa protein, which uses coelenterazine as a substrate and emits light at 480 nm (Lorenz et al., 1991); and (ii) Firefly luciferase (from *Photinus pyralis*), a 61 kDa protein, which uses luciferin as a substrate and emits light at 560 nm (de Wet et al., 1987).

TABLE 1

Exemplary bioluminescent proteins.

| Species | Name | Organism | MW $kDa \times 10^{-3}$ | Emission (nm) | Substrate |
|---------|------|----------|--------------------------|---------------|-----------|
| Insect | FFluc | *Photinus pyralis* (North American Firefly) | ~61 | 560 | D-(−)-2-(6′-hydroxybenzothiazolyl)-$\Delta^2$-thiazoline-4-carboxylic acid, HBTTCA |

TABLE 1-continued

Exemplary bioluminescent proteins.

| Species | Name | Organism | MW kDa × $10^{-3}$ | Emission (nm) | Substrate |
|---|---|---|---|---|---|
| Insect | FF'luc | Luciola cruciata (Japanese Firefly) | | 560-590 (many mutants) | ($C_{11}H_8N_2O_3S_2$) (luciferin) Luciferin |
| Insect | | Phengodid beetles (railroad worms) | | | |
| Insect | | Arachnocampa sp. | | | Luciferin |
| Insect | | Orphelia fultoni (North American glow worm) | | | |
| Insect | Clluc | Pyrophorus plagiophthalamus (click beetle) | | 546, 560, 578 and 593 | Luciferin |
| Jellyfish | Aequorin | Aequorea | 44.9 | 460-470 | Coelenterazine |
| Sea pansy | Rluc | Renilla Reniformis | 36 | 480 | Coelenterazine |
| Sea pansy (modified) | Rluc8 | Renilla reniformis (modified) | 36 | 487 (peak) | Coelenterazine/ Deep Blue C |
| Sea pansy | Rmluc | Renilla mullerei | 36.1 | ~480 | Coelenterazine |
| Sea pansy | | Renilla kollikeri | | | |
| Crustacea (shimp) | Vluc | Vargula hilgendorfii | ~62 | ~460 | coelenterazine * |
| Crustacea | | Cypridina (sea firefly) | 75 | 460 | coelenterazine ** |
| Dinofagellate (marine alga) | | Gonyaulax polyedra | 130 | ~475 | Tetrapyrrole |
| Mollusc | | Latia (fresh water limpet) | 170 | 500 | Enol formate, terpene, aldehyde |
| Hydroid | | Obelia biscuspidata | ~20 | ~470 | Coelenterazine |
| Shrimp | | Oplophorus gracilorostris | 31 | 462 | Coelenterazine |
| Others | Ptluc | Ptilosarcus | | ~490 | Coelenterazine |
| | Glue | Gaussia | ~20 | ~475 | Coelenterazine |
| | Plluc | Pleuromamma | 22.6 | ~475 | Coelenterazine |

*Gaussia* luciferase (from *Gaussia princeps*) has been used in biochemical assays (Verhaegen et al., 2002). *Gaussia* luciferase is a 20 kDa protein that oxidises coelenterazine in a rapid reaction resulting in a bright light emission at 470 nm.

Luciferases useful for the present invention have also been characterized from *Anachnocampa* sp (WO 2007/019634). These enzymes are about 59 kDa in size and are ATP-dependent luciferases that catalyze luminescence reactions with emission spectra within the blue portion of the spectrum.

Alternative, non-luciferase, bioluminescent proteins that can be employed in this invention are any enzymes which can act on suitable substrates to generate a luminescent signal. Specific examples of such enzymes are β-galactosidase, lactamase, horseradish peroxidase, alkaline phophatase, β-glucuronidase and β-glucosidase. Synthetic luminescent substrates for these enzymes are well known in the art and are commercially available from companies, such as Tropix Inc. (Bedford, Mass., USA).

An example of a peroxidase useful for the present invention is described by Hushpulian et al. (2007).

In a preferred embodiment, a bioluminescent protein with a small molecular weight is used to prevent an inhibition of the interaction due to steric hindrance. The bioluminescent protein preferably consists of a single polypeptide chain. Also the bioluminescent proteins preferably do not form oligomers or aggregates. The bioluminescent proteins *Renilla* luciferase, *Gaussia* luciferase and Firefly luciferase meet all or most of these criteria.

Substrates

The choice of the substrate can impact on the wavelength and the intensity of the light generated by the bioluminescent protein.

A widely known substrate is coelenterazine which occurs in cnidarians, copepods, chaetgnaths, ctenophores, decapod shrimps, mysid shrimps, radiolarians and some fish taxa (Greer and Szalay, 2002). For *Renilla* luciferase for example, coelenterazine analogues/derivatives are available that result in light emission between 418 and 512 nm (Inouye et al., 1997). A coelenterazine analogue/derivative (400A, Deep-BlueC) has been described emitting light at 400 nm with *Renilla* luciferase (WO 01/46691). Other examples of coelenterazine analogues/derivatives are EnduRen and ViviRen.

As used herein, the term "luciferin" refers to a class of light-emitting biological pigments found in organisms capable of bioluminescence, which are oxidised in the presence of the enzyme luciferase to produce oxyluciferin and energy in the form of light. Luciferin, or 2-(6-hydroxybenzothiazol-2-yl)-2-thiazoline-4-carboxylic acid, was first isolated from the firefly *Photinus pyralis*. Since then, various forms of luciferin have been discovered and studied from various different organisms, mainly from the ocean, for example fish and squid, however, many have been identified in land dwelling organisms, for example, worms, beetles and various other insects (Day et al., 2004; Viviani, 2002).

There are at least five general types of luciferin, which are each chemically different and catalysed by chemically and structurally different luciferases that employ a wide range of different cofactors. First, is firefly luciferin, the substrate of firefly luciferase, which requires ATP for catalysis (EC 1.13.12.7). Second, is bacterial luciferin, also found in some squid and fish, that consists of a long chain aldehyde and a reduced riboflavin phosphate. Bacterial luciferase is FMNH-dependent. Third, is dinoflagellate luciferin, a tetrapyrrolic chlorophyll derivative found in dinoflagellates (marine plankton), the organisms responsible for night-time ocean phosphorescence. Dinoflagellate luciferase catalyses the oxidation of dinoflagellate luciferin and consists of three identical and catalytically active domains. Fourth, is the imidazolopyrazine vargulin, which is found in certain ostracods and deep-sea fish, for example, Porichthys. Last, is coelanterazine (an imidazolpyrazine), the light-emitter of the protein aequorin, found in radiolarians, ctenophores, cnidarians, squid, copepods, chaetognaths, fish and shrimp.

Acceptor Molecules

There are a number of different acceptor molecules that can be employed in this invention. The acceptor molecules may be a protein or non-proteinaceous. Examples of acceptor molecules that are protein include, but are not limited to, green fluorescent protein (GFP), blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz, GFPuv, destabilised EGFP (dEGFP), destabilised ECFP (dECFP), destabilised EYFP (dEYFP), HcRed, t-HcRed, DsRed, DsRed2, t-dimer2, t-dimer2(12), mRFP1, pocilloporin, *Renilla* GFP, Monster GFP, paGFP, Kaede protein or a Phycobiliprotein, or a biologically active variant or fragment of any one thereof. Examples of acceptor molecules that are not proteins include, but are not limited to, Alexa Fluor dye, Bodipy dye, Cy dye, fluorescein, dansyl, umbelliferone, fluorescent microsphere, luminescent microsphere, fluorescent nanocrystal, Marina Blue, Cascade Blue, Cascade Yellow, Pacific Blue, Oregon Green, Tetramethylrhodamine, Rhodamine, Texas Red, rare earth element chelates, or any combination or derivatives thereof.

One very well known example is the group of fluorophores that includes the green fluorescent protein from the jellyfish *Aequorea victoria* and numerous other variants (GFPs) arising from the application of molecular biology, for example mutagenesis and chimeric protein technologies (Tsien, 1998). GFPs are classified based on the distinctive component of their chromophores, each class having distinct excitation and emission wavelengths: class 1, wild-type mixture of neutral phenol and anionic phenolate: class 2, phenolate anion: class 3, neutral phenol: class 4, phenolate anion with stacked s-electron system: class 5, indole: class 6, imidazole: and class 7, phenyl.

A naturally occurring acceptor molecule which has been mutated (variants) can also be useful for the present invention. One example of an engineered system which is suitable for BRET is a *Renilla* luciferase and enhanced yellow mutant of GFP (EYFP) pairing which do not directly interact to a significant degree with one another alone in the absence of a mediating protein(s) (in this case, the G protein coupled receptor) (Xu et al., 1999).

In another embodiment, the acceptor molecule is a fluorescent nanocrystal. Nanocrystals, or "quantum dots", have several advantages over organic molecules as fluorescent labels, including resistance to photodegradation, improved brightness, non-toxicity, and size dependent, narrow emission spectra that enables the monitoring of several processes simultaneously. Additionally, the absorption spectrum of nanocrystals is continuous above the first peak, enabling all sizes, and hence all colors, to be excited with a single excitation wavelength.

Fluorescent nanocrystals may be attached, or "bioconjugated", to proteins in a variety of ways. For example, the surface cap of a "quantum dot" may be negatively charged with carboxylate groups from either dihydrolipoic acid (DHLA) or an amphiphilic polymer. Proteins can be conjugated to the DHLA-nanocrystals electrostatically, either directly or via a bridge consisting of a positively charged leucine zipper peptide fused to recombinant protein. The latter binds to a primary antibody with specificity for the intended target. Alternatively, antibodies, streptavidin, or other proteins are coupled covalently to the polyacrylate cap of the nanocrystal with conventional carbodiimide chemistry.

There are colloidal methods to produce nanocrystals, including cadmium selenide, cadmium sulfide, indium arsenide, and indium phosphide. These quantum dots can contain as few as 100 to 100,000 atoms within the quantum dot volume, with a diameter of 10 to 50 atoms. Some quantum dots are small regions of one material buried in another with a larger band gap. These can be so-called core-shell structures, for example, with CdSe in the core and ZnS in the shell or from special forms of silica called ormosil. The larger the dot, the redder (lower energy) its fluorescence spectrum. Conversely, smaller dots emit bluer (higher energy) light. The coloration is directly related to the energy levels of the quantum dot. Quantitatively speaking, the bandgap energy that determines the energy (and hence color) of the fluoresced light is inversely proportional to the square of the size of the quantum dot. Larger quantum dots have more energy levels which are more closely spaced. This allows the quantum dot to absorb photons containing less energy, i.e. those closer to the red end of the spectrum.

In an alternate embodiment, the acceptor molecule is a fluorescent microsphere. These are typically made from polymers, and contain fluorescent molecules (for example fluorescein GFP or YFP) incorporated into the polymer matrix, which can be conjugated to a variety of reagents. Fluorescent microspheres may be labelled internally or on the surface. Internal labelling produces very bright and stable particles with typically narrow fluorescent emission spectra. With internal labelling, surface groups remain available for conjugating ligands (for example, proteins) to the surface of the bead. Internally-labelled beads are used extensively in imaging applications, as they display a greater resistance to photobleaching.

Carboxylate-modified fluorescent microspheres are suitable for covalent coupling of proteins using water-soluble carbodiimide reagents such as 1-ethyl-3-(3-dimethylaminopropyl) carbodiimide hydrochloride (EDAC). Sulfate fluorescent microspheres are relatively hydrophobic and will passively and nearly irreversibly adsorb almost any protein. Aldehyde-sulfate fluorescent microspheres are sulfate microspheres that have been modified to add surface aldehyde groups, and react with proteins.

In another embodiment, the acceptor molecule is a luminescent microsphere. These are typically made from polymers, which contain luminescent molecules (for example complexes of europium or platinum) incorporated into the polymer matrix, which can be conjugated to a variety of reagents.

Bioluminescent Protein and Acceptor Molecule Pairs

A criteria which should be considered in determining suitable pairings for BRET is the relative emission/fluorescence spectrum of the acceptor molecule compared to that of the bioluminescent protein. The emission spectrum of the bioluminescent protein should overlap with the absorbance spectrum of the acceptor molecule such that the light energy from the bioluminescent protein luminescence emission is at a wavelength that is able to excite the acceptor molecule and thereby promote acceptor molecule fluorescence when the two molecules are in a proper proximity and orientation with respect to one another. For example, it has been demonstrated that an *Renilla* luciferase/EGFP pairing is not as good as an *Renilla* luciferase/EYEF pairing based on observable emission spectral peaks (Xu, 1999; Wang, et al. (1997) in Bioluminescence and Chemiluminescence: Molecular Reporting with Photons, eds. Hastings et al. (Wiley, New York), pp. 419-422). To study potential pairing, protein fusions are prepared containing the selected bioluminescent protein and acceptor molecule and are tested, in the presence of an appropriate substrate.

It should also be confirmed that the bioluminescent protein and acceptor molecule do not spuriously associate with each other. This can be accomplished by separate co-expression of the bioluminescent protein and acceptor molecule in the same cells and then monitoring the luminescence spectrum in order to determine if BRET occurs. This may be achieved, for example, using the method of Xu et al. (1999). The selected bioluminescent protein and acceptor molecule form a suitable BRET pair if little or no BRET is observed.

The bioluminescent protein emission can be manipulated by modifications to the substrate. In the case of luciferases the substrate is coelenterazine. The rationale behind altering the bioluminescent protein emission is to improve the resolution between donor emission and acceptor emissions. The original BRET system uses the *Renilla* luciferase as donor, EYFP (or Topaz) as the acceptor and coelenterazine h derivative as the substrate. These components when combined in a BRET assay, generate light in the 475-480 nm range for the bioluminescent protein and the 525-530 nm range for the acceptor molecule, giving a spectral resolution of 45-55 nm.

Unfortunately, *Renilla* luciferase generates a broad emission peak overlapping substantially the GFP emission, which in turn contributes to decrease the signal to noise of the system. One BRET system of the present invention, using coe1400a as the *Renilla* luciferase substrate, provides broad spectral resolution between donor and acceptor emission wavelengths (~105 nm). *Renilla* luciferase with coe1400a generates light between 390-400 nm and a GFP was prepared which absorbs light in this range and re-emits light at 505-508 nm. Because of this increase in spectral resolution between *Renilla* luciferase and GFP emissions, this BRET system provides an excellent biological tool to monitor small changes in conformation of a polypeptide of the invention. This is a significant improvement over the system described previously using the coelenterazine h derivative and EYFP, which has a wavelength difference between donor and acceptor of approximately 51 nm.

Various coelenterazine derivatives are known in the art, including coe1400a, that generate light at various wavelengths (distinct from that generated by the wild type coelenterazine) as a result of *Renilla* luciferase activity. A worker skilled in the art would appreciate that because the light emission peak of the donor has changed, it is necessary to select an acceptor molecule which will absorb light at this wavelength and thereby permit efficient energy transfer. This can be done, for example by altering a GFP class 4 such that it becomes a class 3 or 1 GFP. Spectral overlapping between light emission of the donor and the light absorption peak of the acceptor is one condition among others for an efficient energy transfer. Class 3 and 1 GFPs are known to absorb light at 400 nm and re-emit between 505-511 nm. This results in a wavelength difference between donor and acceptor emissions of approximately 111 nm.

Examples of further bioluminescent proteins and acceptor molecule pairs are provided in Table 2.

TABLE 2

Exemplary BRET bioluminescent proteins and acceptor molecule pairs.

| BDP | Substrate | Substrate wavelength (peak) | Fluorescence acceptor molecule (FAM) | Wavelength of acceptor (Ex/Em) |
|---|---|---|---|---|
| Rluc | Coelenterazine Wild type | 470 nm | Fluorescein | 490/525 nm |
| Rluc | Coelenterazine Wild type | 470 nm | Acridine yellow | 470/550 nm |
| Rluc | Coelenterazine Wild type | 470 nm | Nile red | 485/525 nm |
| Rluc | Coelenterazine cp | 442 nm | Lucifer yellow | 428/540 nm |
| Rluc | Coelenterazine 400 | 400 nm | Quin-2 | 365/490 nm |
| Rluc | Coelenterazine 400 | 400 nm | Dansychloride | 380/475 nm |
| Firefly luciferase | Luciferin | 560 nm | Cyanine Cy3 | 575/605 |
| Firefly luciferase | Luciferin | 560 nm | Texas red | 590/615 |

G Protein Coupled Receptors

G protein-coupled receptors (GPCRs) are also known as seven transmembrane receptors, 7TM receptors, heptahelical receptors, and G protein linked receptors (GPLR). GPCRs are a large protein family of transmembrane receptors that sense molecules outside the cell and activate inside signal transduction pathways and, ultimately, cellular responses. The ligands that bind and activate these receptors include light-sensitive compounds, odors, pheromones, hormones, and neurotransmitters, and vary in size from small molecules to peptides to large proteins. GPCRs are involved in many diseases, but are also the target of around half of all modern medicinal drugs. GPCRs can be grouped into at least 5 classes based on sequence homology and functional similarity:
  Class A rhodopsin-like,
  Class B secretin-like,
  Class C metabotropic/pheromone,
  Class D fungal pheromone, and
  Class E cAMP receptors.

Class A Rhodopsin like receptors include: Amine receptors: Acetylcholine, Alpha Adrenoceptors, Beta Adrenoceptors, Dopamine, Histamine, Serotonin, Octopamine, and Trace amine; Peptide receptors: Angiotensin, Bombesin, Bradykinin, C5a anaphylatoxin, Finet-leu-phe, APJ like, Interleukin-8, Chemokine receptors (C—C Chemokine, C—X—C Chemokine, BONZO receptors (CXC6R), C—X3-C Chemokine, and XC Chemokine), CCK receptors, Endothelin receptors, Melanocortin receptors, Neuropeptide Y receptors, Neurotensin receptors, Opioid receptors, Somatostatin receptors, Tachykinin receptors, (Substance P (NK1), Substance K (NK2), Neuromedin K (NK3), Tachykinin like 1, and Tachykinin like 2), Vasopressin-like receptors (Vasopressin, Oxytocin, and Conopressin), Galanin like receptors (Galanin, Allatostatin, and GPCR 54), Proteinase-activated like receptors (e.g., Thrombin), Orexin & neuropeptide FF, Urotensin II receptors, Adrenomedullin (G10D) receptors, GPR37/endothelin B-like receptors, Chemokine receptor-like receptors, and Neuromedin U receptors; Hormone protein receptors: Follicle stimulating hormone, Lutropin-choriogonadotropic hormone, Thyrotropin, and Gonadotropin; (Rhod)opsin receptors; Olfactory receptors; Prostanoid receptors: Prostaglandin, Prostacyclin, and Thromboxane; Nucleotide-like receptors: Adenosine and Purinoceptors; *Cannabis* receptors; Platelet activating factor receptors;

Gonadotropin-releasing hormone receptors; Thyrotropin-releasing hormone & Secretagogue receptors: Thyrotropin-releasing hormone, Growth hormone secretagogue, and Growth hormone secretagogue like; Melatonin receptors; Viral receptors; Lysosphingolipid & LPA (EDG) receptors; Leukotriene B4 receptor: Leukotriene B4 receptor BLT1 and Leukotriene B4 receptor BLT2; and Class A Orphan/other receptors: Platelet ADP & KI01 receptors, SREB, Mas protooncogene, RDC1, ORPH, LGR like (hormone receptors), GPR, GPR45 like, Cysteinyl leukotriene, Mas-related receptors (MRGs), and GP40 like receptors.

Class B (the secretin-receptor family) of the GPCRs includes receptors for polypeptide hormones (Calcitonin, Corticotropin releasing factor, Gastric inhibitory peptide, Glucagon, Glucagon-like peptide-1,-2, Growth hormone-releasing hormone, Parathyroid hormone, PACAP, Secretin, Vasoactive intestinal polypeptide, Diuretic hormone, EMR1, Latrophilin), molecules thought to mediate intercellular interactions at the plasma membrane (Brain-specific angiogenesis inhibitor (BAI)) and a group of *Drosophila* proteins (Methuselah-like proteins) that regulate stress responses and longevity.

Class C Metabotropic glutamate/pheromone receptors include Metabotropic glutamate, Metabotropic glutamate group I, Metabotropic glutamate group II, Metabotropic glutamate group III, Metabotropic glutamate other, Extracellular calcium-sensing, Putative pheromone Receptors, GABA-B, GABA-B subtype 1, GABA-B subtype 2, and Orphan GPRC5 receptors.

GPCRs are involved in a wide variety of physiological processes, including the visual sense, the sense of smell, behavioral and mood regulation, regulation of immune system activity and inflammation, autonomic nervous system transmission, cell density sensing, and many others. It is known that the inactive G protein is bound to the receptor in its inactive state. Once the ligand is recognized, the receptor or a subunit thereof shifts conformation and thus mechanically activates the G protein, which detaches from the receptor. The receptor can now either activate another G protein, or switch back to its inactive state. It is believed that a receptor molecule exists in a conformational equilibrium between active and inactive biophysical states. The binding of ligands to the receptor may shift the equilibrium toward the active receptor states. Polypeptides of the invention comprise G protein coupled receptors which, when expressed in a cell the N-terminus of the receptor is outside the cell and the C-terminus is inside the cell. The person skilled in the art is aware of suitable techniques for detecting the orientation of a transmembrane protein, Such techniques comprise but are not limited to crystallography, NMR-studies, modeling studies as well as microscopy techniques, like immunolabeling combined with detergent permeabilisation controls for light or electron microscopy preparation, fragment complementation tagging of two polypeptides and the like.

In a preferred embodiment, the G protein coupled receptor is a Class A GPCR. In a further preferred embodiment, the class A (rhodopsin-like) GPCR is an odorant receptor or an adrenergic receptor, more preferably an odorant receptor. The odorant receptor can be from any source as long as when expressed in a cell the N-terminus of the receptor is outside the cell and the C-terminus is inside the cell. Examples include, but are not limited to, a chordate receptor, a nematode receptor, or a biologically active variant or fragment of any one thereof. Examples of chordate receptors include, but are not limited to mammalian receptors, avian receptors and fish receptors. In a preferred embodiment, the odorant receptor is a nematode receptor or biologically active variant or fragment thereof. In an embodiment, the nematode receptor is a *Caenorhabditis elegans* receptor, or biologically active variant or fragment thereof. Examples of odorant receptors that can be used to produce polypeptides of the invention and/or used in the methods of the invention are described in Buck and Axel (1991), Robertson (1998 and 2001), Aloni et al, (2006), Feldmesser (2006), ° lender et al. (2004a and b), Glusman et al. (2000a, 2000b and 2001), Fuchs et al. (2001), Pilpel and Lancet (1999), Sharon et al. (1998), Zozulya et al. (2001), Niimura and Nei (2003), Lander et al. (2001), Zhang and Firestein (2002), Young et al. (2002). Furthermore, a comprehensive list of odorant receptors are available from the SenseLab website (http://senselab.med.yale.edu).

In other embodiments, the GPCR is a Class B or Class C receptor, with Class C being more preferred of these two embodiments.

In a particularly preferred embodiment, the G protein coupled receptor comprises seven transmembrane domains.

The bioluminescent protein can form part of the first, third, fifth non-transmembrane loops (domains) or the C-terminus of the G protein coupled receptor (or polypeptide of the invention). The acceptor molecule also can form part of the first, third, fifth non-transmembrane loops (domains) or the C-terminus of the G protein coupled receptor (or polypeptide of the invention). Each of these regions is intracellular when the G protein coupled receptor is expressed and present in a cell.

The acceptor molecule cannot be in the same region as the bioluminescent protein when part of the same molecule (namely, the same single polypeptide chain), however, the acceptor molecule can be in the equivalent region as the bioluminescent protein when the G protein coupled receptor is present as a dimer or higher multimer. For example, the bioluminescent protein can form part of the C-terminus of one subunit of the receptor, and the acceptor molecule can form part of the C-terminus of another subunit of the receptor. In this example, the subunit to which the label is associated can be the same or different, for instance the two subunits can be identical apart from one labelled with the bioluminescent protein and the other labelled with the acceptor molecule. In one embodiment, the bioluminescent protein forms part of the third non-transmembrane loop of the GPCR subunit, and the acceptor molecule forms part of the fifth non-transmembrane loop. In an alternate embodiment, the acceptor molecule forms part of the third non-transmembrane loop of the GPCR subunit, and the bioluminescent protein forms part of the fifth non-transmembrane loop.

In another embodiment, the bioluminescent protein forms part of the first non-transmembrane loop of the GPCR subunit, and the acceptor molecule forms part of the third non-transmembrane loop. In another embodiment, the acceptor molecule forms part of the first non-transmembrane loop of the GPCR subunit, and the bioluminescent protein forms part of the third non-transmembrane loop.

In a preferred embodiment, the bioluminescent protein forms part of the fifth non-transmembrane loop of the GPCR subunit, and the acceptor molecule forms part of the C-terminus. In an alternate embodiment, the acceptor molecule forms part of the fifth non-transmembrane loop of the GPCR subunit, and the bioluminescent protein forms part of the C-terminus.

In another embodiment, the G protein coupled receptor comprises at least two subunits, where the bioluminescent protein forms part of the third non-transmembrane loop of a first subunit, and the acceptor molecule forms part of the fifth non-transmembrane loop of a second subunit. In an alternate embodiment, the acceptor molecule forms part of the third non-transmembrane loop of a first subunit, and the bioluminescent protein forms part of the fifth non-transmembrane loop of a second subunit.

In another embodiment, the G protein coupled receptor comprises at least two subunits, where the bioluminescent protein forms part of the first non-transmembrane loop of a first subunit, and the acceptor molecule forms part of the third non-transmembrane loop of a second subunit. In another embodiment, the acceptor molecule forms part of the first non-transmembrane loop of a first subunit, and the bioluminescent protein forms part of the third non-transmembrane loop of a second subunit.

In another embodiment, the G protein coupled receptor comprises at least two subunits, where the bioluminescent protein forms part of the fifth non-transmembrane loop of a first subunit, and the acceptor molecule forms part of the C-terminus of a second subunit. In an alternate embodiment, the acceptor molecule forms part of the fifth non-transmembrane loop of a first subunit, and the bioluminescent protein forms part of the C-terminus of a second subunit.

In another embodiment, the G protein coupled receptor comprises at least two subunits and the donor and acceptor molecule are in the same site of the first and second subunits respectively.

In an embodiment, the bioluminescent protein or acceptor molecule is located after the second amino acid of the fifth transmembrane domain and before the second amino acid before the beginning of sixth transmembrane domain. In another embodiment, the bioluminescent protein or acceptor molecule is located after about amino acid 8 after the fifth transmembrane domain or after about amino acid 22 after the fifth transmembrane domain. In a further embodiment, the bioluminescent protein or acceptor molecule is inserted about 10 or 12 amino acids before the sixth transmembrane domain. Most preferably, the bioluminescent protein or acceptor molecule is located in the middle of the third non-transmembrane loop (domain).

With regard to the C-terminus, it is preferred that about 5 to 25 amino acids of the natural C-terminus remain at the end of seventh transmembrane domain. Preferably, the bioluminescent protein or acceptor molecule is inserted after about the 16 or 20 amino acids after the seventh transmembrane.

Turning to the location of the bioluminescent protein or acceptor molecule in the first non-transmembrane loop (domain), it is preferred that said label is inserted about two amino acids after the end of first transmembrane domain and about two amino acids before the beginning of the second transmembrane domain. Most preferably, the bioluminescent protein or acceptor molecule is located in the middle of the first non-transmembrane loop (domain).

In a further embodiment, the bioluminescent protein can form part of the N-terminus, second, fourth, or sixth non-transmembrane loops (domains) of the G protein coupled receptor (or polypeptide of the invention). The acceptor molecule also can form part of the N-terminus, second, fourth, or sixth non-transmembrane loops (domains) of the G protein coupled receptor (or polypeptide of the invention), however, it cannot be in the same region as the bioluminescent protein when part of the same molecule. Each of these regions is extracellular when the G protein coupled receptor is expressed and present in a cell.

The GPCR may be a non-naturally occurring chimera of two or more different GPCRs. In particular, this enables a transduction cassette to be produced where portions of one receptor are always present in the chimera into which other portions of a wide variety of GPCRs are inserted depending on the compound to be detected.

In one embodiment, the subunit comprises the N-terminus and at least a majority of the first transmembrane domain of a first G protein coupled receptor subunit, at least a majority of the first non-transmembrane loop through to at least a majority of the fifth transmembrane domain of a second G protein coupled receptor subunit, and at least a majority of the fifth non-transmembrane loop through to the C-terminal end of the first G protein coupled receptor subunit.

In another embodiment, the subunit comprises the N-terminus through to at least a majority of the fifth transmembrane domain of a first G protein coupled receptor subunit, and at least a majority of the fifth non-transmembrane loop through to the C-terminal end of a second G protein coupled receptor subunit.

The skilled person can readily determine the N-terminal end, transmembrane domains, non-transmembrane loops (domains) and C-terminus of a G protein coupled. For example, a variety of bioinformatics approaches may be used to determine the location and topology of transmembrane domains in a protein, based on its amino acid sequence and similarity with known transmembrane domain of G protein coupled receptors. Alignments and amino acid sequence comparisons are routinely performed in the art, for example, by using the BLAST program or the CLUSTAL W program. Based on alignments with known transmembrane domain-containing proteins, it is possible for one skilled in the art to predict the location of transmembrane domains. Furthermore, the 3 dimensional structures of some membrane-spanning proteins are known, for example, the seven transmembrane G-protein coupled rhodopsin photoreceptor structure has been solved by x-ray crystallography. Based on analyses and comparisons with such 3D structures, it may be possible to predict the location and topology of transmembrane domains in other membrane proteins. There are also many programs available for predicting the location and topology of transmembrane domains in proteins. For example, one may use one or a combination of the TMpred (Hofmann and Stoffel, 1993), which predicts membrane spanning proteins segments; TopPred (von Heijne et al., 1992.) which predicts the topology of membrane proteins; PREDATOR (Frishman and Argos, 1997), which predicts secondary structure from single and multiple sequences; TMAP (Persson and Argos, 1994), which predicts transmembrane regions of proteins from multiply aligned sequences; and ALOM2 (Klien et al., 1984), which predicts transmembrane regions from single sequences.

In accordance with standard nomenclature, the numbering of the transmembrane domains and non-transmembrane loops (domains) is relative to the N-terminus of the polypeptide.

Amino acid sequence mutants/variants of naturally occurring G protein coupled receptors can be prepared by introducing appropriate nucleotide changes into the encoding polynucleotide, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (variant) polypeptides can be prepared using any technique known in the art. For example, a polynucleotide described herein can be subjected to in vitro mutagenesis. Such in vitro mutagenesis techniques may include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides encoding G protein coupled receptors are subjected to DNA shuffling techniques as broadly described by Harayama (1998). Products derived from mutated/variant DNA can readily be screened using techniques described herein to determine if they are useful for the methods of the invention.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the G protein coupled receptor removed and a different residue inserted in its place. The sites of greatest interest for substitutional mutagenesis include sites identified as important for function. Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 3.

Furthermore, if desired, unnatural amino acids or chemical amino acid analogues can be introduced as a substitution or addition into a polypeptide described herein. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide.

TABLE 3

| Exemplary substitutions. | |
|---|---|
| Original Residue | Exemplary Substitutions |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |

TABLE 3-continued

| Exemplary substitutions. | |
|---|---|
| Original Residue | Exemplary Substitutions |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

Polypeptides described herein can be produced in a variety of ways, including production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Accessory Molecules

An accessory molecule is a protein which is involved in G coupled protein receptor signalling. Examples include G proteins and arrestins. Any labelled accessory molecule can be used in the methods of the present invention as long as they directly or indirectly associate with the G protein coupled receptor (and/or polypeptide defined herein) and following binding of the compound to the G protein coupled receptor there is a spatial alteration in the relative position of the two labels to allow for BRET detection.

The skilled person can readily identify accessory molecules that associate with a specific G protein coupled receptor using standard techniques in the art.

Details of mutants (variants) described above for G protein coupled receptors also apply to the accessory molecules.

The bioluminescent protein or acceptor molecule can be located anywhere in the accessory molecule as long as the accessory molecule is still able to directly or indirectly bind the receptor, and following binding of a compound of interest a change in BRET can be detected. In an embodiment, the bioluminescent protein or acceptor molecule is located at the C-terminus or N-terminus of the accessory molecule. The accessory molecule indirectly binds the receptor if it requires at least one other accessory molecule to form a complex with the GPCR, for instance a first accessory molecule binds the receptor and a second accessory molecule indirectly binds the receptor by directly binding to the first accessory molecule.

G Proteins

G-proteins are a family of proteins involved in second messenger cascades for intracellular signaling. G proteins function as "molecular switches," alternating between an inactive guanosine diphosphate (GDP) bound state and an active guanosine triphosphate (GTP) bound state. Ultimately, G proteins regulate downstream cell processes by initiating cascades of signal transduction networks Hofmann et al., 2009; Oldham and Hamm, 2008).

There are two distinct families of G proteins: Heterotrimeric G proteins, sometimes referred to as the "large" G proteins, that are activated by G protein-coupled receptors and made up of alpha (α), beta (β), and gamma (γ) subunits; and "small" G proteins (20-25 kDa) that belong to the Ras superfamily of small GTPases. These proteins are homologous to the alpha (α) subunit found in heterotrimeric G proteins, and also bind GTP and GDP and are involved in signal transduction. In order to associate with the plasma membrane, many G proteins are covalently modified with lipids, for example heterotrimeric G protein subunits may be myristolated, palmitoylated, or prenylated, while small G proteins may be prenylated.

As the skilled addressee will be aware, there are many known G-proteins. A number of heterotrimeric G proteins have been identified in nematodes, for example C. elegans has 21 Gα, 2 Gβ and 2 Gγ genes (Jansen et al., 1999; Cuppen et al., 2003). Based on sequence similarity, mammalian Gα subunits have been divided into four families: Gs, Gi/o, Gq and G12 (Neves et al., 2002). C. elegans expresses one ortholog of each of the mammalian families: GSA-1 (Gs), GOA-1 (Gi/o), EGL-30 (Gq) and GPA-12 (G12). The remaining C. elegans α subunits (GPA-1-11, GPA-13-17 and ODR-3) do not share sufficient homology to allow classification. The conserved Gα subunits, with the exception of GPA-12, are expressed broadly while 14 of the new Gα genes are expressed in subsets of chemosensory neurons.

The Gβ subunit, GPB-1, as well as the Gγ subunit, GPC-2, appear to function along with the α subunits in the classic G protein heterotrimer. The remaining Gβ subunit, GPB-2, is thought to regulate the function of certain RGS proteins, while the remaining Gγ subunit, GPC-1, has a restricted role in chemosensation. The functional difference for most G protein pathways in C. elegans, therefore, resides in the α subunit.

Arrestins

Arrestins are one of the key proteins for the termination of G protein signaling. Activated GPCRs are specifically phosphorylated by G protein-coupled receptor kinases (GRKs) and then bind to arrestins to preclude the receptor/G protein interaction, resulting in quenching of the following signal transduction. Arrestins bind GPCRs, including those that have been agonist-activated and bind more tightly to those that have been phosphorylated by GRKs than those that are not.

Two distinct patterns of arrestin trafficking within the cell have been delineated resulting in the classification of GPCRs as follows: Class A where arrestin interacts with the receptor at the cell surface but does not endocytose into vesicles, thus showing a transient interaction with the receptor, and class B in which R-arrestins and receptor traffic together from the cell membrane to endocytic vesicles. These two classes of receptors also differ with regard to their affinity for different arrestin isoforms. In addition, Class A receptors preferentially bind R-arrestin2 whereas class B receptors bind to β-arrestin1 and H-arrestin2 with equal affinity.

R-arrestin-binding leads to the uncoupling of the receptor from its cognate G-proteins, causing dampening or desensitization of GPCR signaling via the downstream second messenger molecules.

While terminating G-protein signals, arrestin binding can initiate new signaling from GPCRs. For example, R-arrestins serve as adaptors, which bring non-receptor tyrosine kinases, such as Src, to form signaling complexes with the internalizing receptor. H-arrestins function as GPCR-regulated scaffolds for MAPK modules such as ASK-MKK4-JNK3 and RAF-MEK-ERK1/2. In addition, arrestins interact with proteins of the endocytic machinery, such as clathrin, β-adaptin subunit2 of the AP2 complex, and Arf-6 and thus promote internalization of receptors via clathrin-coated vesicles.

An example of a nematode arrestin is ARR-1 from C. elegans, which is primarily expressed in the nervous system, including the HSN neuron and various chemosensory neurons, involved in detecting soluble and volatile odorants. Over 20 putative arrestins have now been identified in the nematode C. elegans. Such arrestins are expressed throughout the nervous system and support receptor internalization, similarly to the vertebrate non-visual arrestins, yet participate in olfaction and vision, similarly to the visual/sensory subtypes.

Recombinant Vectors

One embodiment of the present invention includes a recombinant vector, which comprises at least one isolated/exogenous polynucleotide encoding a polypeptide as described herein, inserted into any vector capable of delivering the polynucleotide molecule into a host cell. Such a vector contains heterologous polynucleotide sequences, that are polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and typically is a transposon (such as described in U.S. Pat. No. 5,792,294), a virus or a plasmid.

One type of recombinant vector comprises the polynucleotide(s) operably linked to an expression vector. The phrase operably linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors include any vectors that function (i.e., direct gene expression) in recombinant cells, including in bacterial, fungal, endoparasite, arthropod, animal, and plant cells. Vectors of the invention can also be used to produce the polypeptide in a cell-free expression system, such systems are well known in the art.

"Operably linked" as used herein refers to a functional relationship between two or more nucleic acid (e.g., DNA) segments. Typically, it refers to the functional relationship of transcriptional regulatory element to a transcribed sequence. For example, a promoter is operably linked to a coding sequence, such as a polynucleotide defined herein, if it stimulates or modulates the transcription of the coding sequence in an appropriate host cell and/or in a cell-free expression system. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

In particular, expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, arthropod, nematode, plant or animal cells, such as, but not limited to, tac, lac, trp, trc, oxy-pro, omp/lpp, rrnB, bacteriophage lambda, bacteriophage T7, T7lac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells.

Host Cells

Another embodiment of the present invention includes a host cell transformed with one or more recombinant molecules described herein or progeny cells thereof. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells of the present invention either can be endogenously (i.e., naturally) capable of producing polypeptides described herein or can be capable of producing such polypeptides after being transformed with at least one polynucleotide molecule as described herein. Host cells of the present invention can be any cell capable of producing at least one protein defined herein, and include bacterial, fungal (including yeast), parasite, nematode, arthropod, animal and plant cells. Examples of host cells include *Salmonella, Escherichia, Bacillus, Listeria, Saccharomyces, Spodoptera, Mycobacteria, Trichoplusia*, BHK (baby hamster kidney) cells, MDCK cells, CRFK cells, CV-1 cells, COS (e.g., COS-7) cells, and Vero cells. Further examples of host cells are *E. coli*, including *E. coli* K-12 derivatives; *Salmonella typhi; Salmonella typhimurium*, including attenuated strains; *Spodoptera frugiperda; Trichoplusia ni*; and non-tumorigenic mouse myoblast G8 cells (e.g., ATCC CRL 1246). Particularly preferred host cells are yeast cells such as, but not limited to, *Saccharomyces* spp., in particular, *Saccharomyces cerevisiae, Candida* spp., *Hansenula* spp. or *Pichia* spp.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

Cell-Free Compositions

Methods for preparing cell-free compositions from cells are well-known in the art and include repeated cycles of freezing and thawing, grinding, treatment of cells with ultrasound in a sonicator device, homogenization, the use of a French press, the addition of detergent and/or enzymes, glass-bead lysis, differential centrifugation, several density gradient procedures using a variety of gradient media. These techniques are familiar to the skilled worker and are dealt with in detail for example in "Current Protocols in Protein Science"; John E. Caligan; Ben M. Dunn; Hidde L. Ploegh; David W. Speicher; Paul T. Wingfield; Wiley and Sons).

For isolating or preparing cell membrane extracts, a combination of these methods is usually employed (Rieder and Emr, 2001). Generally, cells are lysed either by mechanical means, or using detergents, and the membrane fractions isolated via differential centrifugation, for example, as outlined in U.S. Pat. No. 7,393,934, The method outlined in Moore (1994) is commonly used. An example of such a method can be found in U.S. Pat. No. 7,320,875. Other methods are also available for the preparation of membrane fractions, for example, aqueous two-phase affinity partitioning (Persson and Jergil, 1994).

There are also many commercial kits available for purifying cell membrane fractions, for example, Qiagen's Qproteome Plasma Membrane Protein Kit Cells are incubated in a hypotonic buffer, causing them to swell. A mild detergent is added and the resulting cell suspension is homogenized by mechanical disruption. Intact cells, cell debris, nuclei and major organelles are removed by centrifugation. The resulting supernatant contains cytosolic proteins and microsomes, Golgi vesicles, and plasma. membranes. A ligand specific for molecules on the cell membrane is added to the supernatant. The ligand binds to the cell membrane vesicles and the ligand-vesicle complexes are precipitated using magnetic beads that bind to the ligand. After washing, plasma membrane vesicles are eluted under native conditions and the ligand remains bound to the beads.

For yeast cells, a commonly used method for preparing cell membranes is to spheroplast the cells. This gives high yields, and is ideally suited to the large-scale isolation of plasma membranes. Such a method generally entails coating the negatively charged surfaces of the spheroplasts with dense cationic silica beads. Which makes the membrane denser than any other membranous organelle of the cell. A washing procedure removes the excess cationic beads, followed by addition of polyacrylic acid to block the free cationic groups on the beads. The coated spheroplasts are subsequently lysed by hand homogenization in an EGTA-containing lysis buffer to prevent aggregation of membrane components. Centrifugation of the spheroplast lysate pellets the heavy plasma membrane-microbead assemblies, leaving intracellular membranous organelles in the supernatant.

Further examples of the production of cell-free composition comprising G protein coupled receptor-related polypeptides which can be used for the present invention are described in Kaiser et al. (2008).

In certain embodiments, a polypeptide of the invention comprising a GPCR are embedded in the lipid bilayer of a liposome preparation. As used herein, the term "liposome" refers to a closed vesicle comprising bilayers of amphiphilic phospholipids, for example phosphliatidyl ethanolamine and cholesterol. Liposomes can be composed of naturally-derived phospholipids with mixed lipid chains (like phosphatidylethanolamine), or of pure surfactant components like DOPE (dioleoylphosphatidylethanolamine).

Liposomes containing polypeptides described herein may be created by disrupting the phospholipid membrane of cells expressing the protein in water, for example by sonication. The phospholipids would reassemble into liposomal spheres containing a core of aqueous solution. Low shear rates would create multilamellar liposomes, which have many layers. Continued high-shear sonication would form smaller unilamellar liposomes, more suited to the application of the present invention. Experimentation to produce the optimal liposome size with optimal orientation and accessibility is within the routine capabilities of one of ordinary skill in the art.

Polypeptides described herein may also be produced and incorporated into liposomes by membrane reconstitution techniques involving dissociation in detergents, followed by their reconstitution in the presence of lipids and removal of the detergents. The liposome composition would be adjusted so as to ensure optimal orientation and accessibility of the polypeptides contained in the liposomes with binding partners (compounds). Such adjustments to achieve optimal liposome compositions are routine in the art.

Assays for BRET

In a preferred embodiment, the energy transfer occurring between the bioluminescent protein and acceptor molecule is presented as calculated ratios from the emissions measured using optical filters (one for the acceptor molecule emission and the other for the bioluminescent protein emission) that select specific wavelengths (see equation 1).

$$Ea/Ed = BRET \text{ ratio} \quad (1)$$

where Ea is defined as the acceptor molecule emission intensity (emission light is selected using a specific filter adapted for the emission of the acceptor) and Ed is defined as the bioluminescent protein emission intensity (emission light is selected using a specific filter adapted for the emission of the bioluminescent protein).

It should be readily appreciated by those skilled in the art that the optical filters may be any type of filter that permits wavelength discrimination suitable for BRET. For example, optical filters used in accordance with the present invention can be interference filters, long pass filters, short pass filters, etc. Intensities (usually in counts per second (CPS) or relative luminescence units (RLU)) of the wavelengths passing through filters can be quantified using either a photo-multiplier tube (PMT) or a CCD camera. The quantified signals are subsequently used to calculate BRET ratios and represent energy transfer efficiency. The BRET ratio increases with increasing intensity of the acceptor emission.

Generally, a ratio of the acceptor emission intensity over the donor emission intensity is determined (see equation 1), which is a number expressed in arbitrary units that reflects energy transfer efficiency. The ratio increases with an increase of energy transfer efficiency (see Xu et al., 1999).

Energy transfer efficiencies can also be represented using the inverse ratio of donor emission intensity over acceptor emission intensity (see equation 2). In this case, ratios decrease with increasing energy transfer efficiency. Prior to performing this calculation the emission intensities are corrected for the presence of background light and auto-luminescence of the substrate. This correction is generally made by subtracting the emission intensity, measured at the appropriate wavelength, from a control sample containing the substrate but no bioluminescent protein, acceptor molecule or polypeptide of the invention.

$$Ed/Ea = BRET \text{ ratio} \quad (2)$$

where Ea and Ed are as defined above.

The light intensity of the bioluminescent protein and acceptor molecule emission can also be quantified using a monochromator-based instrument such as a spectrofluorometer, a charged coupled device (CCD) camera or a diode array detector. Using a spectrofluorometer, the emission scan is performed such that both bioluminescent protein and acceptor molecule emission peaks are detected upon addition of the substrate. The areas under the peaks represent the relative light intensities and are used to calculate the ratios, as outlined above. Any instrument capable of measuring lights for the bioluminescent protein and acceptor molecule from the same sample, can be used to monitor the BRET system of the present invention.

In an alternative embodiment, the acceptor molecule emission alone is suitable for effective detection and/or quantification of BRET. In this case, the energy transfer efficiency is represented using only the acceptor emission intensity. It would be readily apparent to one skilled in the art that in order to measure energy transfer, one can use the acceptor emission intensity without making any ratio calculation. This is due to the fact that ideally the acceptor molecule will emit light only if it absorbs the light transferred from the bioluminescent protein. In this case only one light filter is necessary.

In a related embodiment, the bioluminescent protein emission alone is suitable for effective detection and/or quantification of BRET. In this case, the energy transfer efficiency is calculated using only the bioluminescent protein emission intensity. It would be readily apparent to one skilled in the art that in order to measure energy transfer, one can use the donor emission intensity without making any ratio calculation. This is due to the fact that as the acceptor molecule absorbs the light transferred from the bioluminescent protein there is a corresponding decrease in detectable emission from the bioluminescent protein. In this case only one light filter is necessary.

In an alternative embodiment, the energy transfer efficiency is represented using a ratiometric measurement which only requires one optical filter for the measurement. In this case, light intensity for the donor or the acceptor is determined using the appropriate optical filter and another measurement of the samples is made without the use of any filter (intensity of the open spectrum). In this latter measurement, total light output (for all wavelengths) is quantified. Ratio calculations are then made using either equation 3 or 4. For the equation 3, only the optical filter for the acceptor is required. For the equation 4, only the optical filter for the donor is required.

$$Ea/Eo-Ea=\text{BRET ratio or }=Eo-Ea/Ea \quad (3)$$

$$Eo-Ed/Ed=\text{BRET ratio or }=Ed/Eo-Ed \quad (4)$$

where Ea and Ed are as defined above and Eo is defined as the emission intensity for all wavelengths combined (open spectrum).

It should be readily apparent to one skilled in the art that further equations can be derived from equations 1 through 4. For example, one such derivative involves correcting for background light present at the emission wavelength for bioluminescent protein and/or acceptor molecule.

In performing a BRET assay, light emissions can be determined from each well using the BRETCount. The BRETCount instrument is a modified TopCount, wherein the TopCount is a microtiterplate scintillation and luminescence counter sold by Packard Instrument (Meriden, Conn.). Unlike classical counters which utilise two photomultiplier tubes (PMTs) in coincidence to eliminate background noise, TopCount employs single-PMT technology and time-resolved pulse counting for noise reduction to allow counting in standard opaque microtiterplates. The use of opaque microtiterplates can reduce optical crosstalk to negligible level. TopCount comes in various formats, including 1, 2, 6 and 12 detectors (PMTs) which allow simultaneous reading of 1, 2, 6 or 12 samples, respectively. Beside the BRETCount, other commercially available instrument are capable of performing BRET: the Victor 2 (Wallac, Finland (Perkin Elmer Life Sciences)) and the Fusion (Packard Instrument, Meriden). BRET can be performed using readers that can detect at least the acceptor molecule emission and preferably two wavelengths (for the acceptor molecule and the bioluminescent protein) or more.

In an embodiment of the invention, BRET is detected using a microfluidics device. Microfluidics devices conveniently require only an aliquot of the sample, generally not more than about 50 µL, to be transferred to the sample reservoir of the microfluidics device. This is performed either manually or by pneumatic injection via a syringe, capillary or the like.

An automated luminescence biochip device using microfluidics may be used to perform all the necessary BRET reaction steps. Automating BRET reactions in a microfluidic biochip platform is desirable as this avoids multiple manual handling steps and reduces human time and effort in performing experiments. The microfluidics device may contain a self-contained disposable biochip with patterned microchannels and compartments having storage means for storing a plurality of samples, reagents, and substrates. The steps of transferring sequentially at least one of the samples, or reagents, and then luminescent substrate from compartments through microchannels to the reaction sites could be automated. The luminescent substrates would then react with the donor molecules resulting in luminescence, which would be detected by an optical detector. An example of a microfluidics device for detecting luminescence is described in U.S. Pat. No. 6,949,377.

Uses

The present invention can be used to detect a wide variety of compounds, particularly odorants. Typically, the odorant will be a volatile organic or inorganic compound or inorganic gas that may be detected by chemosensory odorant receptors of at least one organism. These may include amine- and/or sulphydyrl-containing compounds, carboxylic acids, alcohols, aldehydes, alkanes, alkenes, aromatic compounds, esters, terpenes or terpene-derivatives, ethers, $CO_2$ etc. as well as compounds bearing combinations of these features.

Odorants may be indicative of some biological or chemical state of value or of interest to humans. Such indications may include:

The sensory appeal, quality or safety of food and beverages, pharmaceuticals or related materials.

The health, nutritional or exercise status of humans or animals.

The presence or absence of hazardous substances, including pathogens.

The progress or status of industrial processes.

An environmental contamination or state.

The sensory appeal, quality or safety of perfumes, fragrances or other cosmetics.

In a particularly preferred embodiment, the compound only binds the receptor portion of a polypeptide described herein.

In a particularly preferred embodiment, the polypeptide defined herein comprising an odorant receptor is used in a biosensor to detect a compound(s) of interest. A biosensor is a device for the detection of an analyte that combines a biological component with a physicochemical detector component. It typically consists of three parts, firstly at least one polypeptide defined herein comprising a G protein coupled receptor. Second, a transducer or detector element is required, which works in a physicochemical way (eg. optical, electrochemical) that transforms the signal resulting from the interaction of the compound with the polypeptide into another signal (i.e. transducers) that can be more easily measured and quantified. Third, an associated electronic or signal processor is required, which then displays the results of the interaction in a user-friendly way. An example of a biosensor involving BRET is described in Charest et al. (2005).

In another embodiment, the methods of screening are used for drug discovery and/or development. More specifically, the receptor is a target for potential therapeutics. Thus, in this embodiment it is preferred that the receptor is a clinically important molecule such as, but not limited to, an adrenergic receptor, a serotinin receptor, a dopamine receptor, metabotropic/glumtamte receptor, a GABA receptor, a vomeronasal receptor, a taste receptor, or a secretin-like receptor.

Within the scope of the present invention are also methods for identifying, characterizing and for screening of molecules which are capable of interacting with an G protein coupled receptor which comprise so-called high-throughput screening methods and similar approaches which are known in the art (Spencer, 1998; Oldenburg, 1998; Milligan, 1999) carried out using 96-well, 384-well, 1536-well (and other) commercially available plates. Further methods to be employed in accordance with the present invention comprise, but are not limited to, homogenous fluorescence readouts in high-throughput screenings (as described, inter alia, in Pope, 1999).

As the skilled person would be aware, the present invention can also be mutliplexed. In this system, two or more polypeptides comprising different G protein coupled receptors are provided which bind different compounds. Each different G protein coupled receptor is labelled with a different bioluminescent protein and/or acceptor molecule such that they emit at different wavelengths to enable the detection and quantification of different target compounds.

EXAMPLES

Example 1

Dual Labelled Bret ODR-10 (OGPR)Constructs

Materials and Methods
Design and Construction of Dual Labelled BRET OR Constructs $BRET^2$ receptor constructs were generated with $BRET^2$ components inserted into the third intracellular loop (IC3) and at the C-terminus. Two BRET constructs were made with; (1) $GFP^2$ in the middle of IC3 and RLuc(h) on the C-terminus; (2) OR with RLuc(h) in the middle of IC3 and $GFP^2$ on the C-terminus. The position of the third intracellular loop (IC3) was determined using TMAP on The Biology Workbench a web-based tool for prediction of transmembrane segments (http://seqtool.sdsc.edu). For ODR-10, the middle of the IC3 is amino acids 240-241. The amino acid sequence for this construct referred to as OGOR, is provided as SEQ ID NO:15 (encoding nucleotide sequence provided as SEQ ID NO:16).

ODR-10 was amplified from *C. elegans* cDNA, which was prepared with standard techniques using superscript II (Invitrogen). PCR conditions were as follows 94° C. 2 mins, 30 cycles of 94° C. 15 secs, 59° C. 30 secs, 68° C. 70 sec, and a final extension step of 68° C. for 5 min. Standard Pfx50 PCR ingredients were used with primers ODR-10Xba1F 5'-AGTCTAGAATGTCGGGAGAATTGTGGATTA-3' (SEQ ID NO: 21) and ODR-10-attb1-R 5'-GGGGA-CAAGTTTGTACAAAAAAGCAGGCTTCAT-CACGTCGGAACTTGAG-3' (SEQ ID NO:22). Amplified cDNA was cloned into pGEM-T (Promega) and sequenced.

The BRET components, $GFP^2$ and *Renilla* Luciferase, RLuc(h), were sourced from a commercially available plasmid $pGFP^2$-MCS-Rluc(h) (PerkinElmer; Lot#6310051-6D1).

BRET constructs were constructed by PCR amplification of individual fragments of the construct (see Table 4 for primers and annealing temperatures). PCR was performed with Pfx50™ standard ingredients (Invitrogen) and conditions were as follows 94° C. 2 min, 30 cycles of 94° C. 15 sec, 59° C. 30 sec, 68° C. 70 sec, and a final extension step of 68° C. for 5 min. Separate components of the constructs were amplified using overlapping primers.

TABLE 4

Primers for dual tagged ODR-10 receptor constructs.

| Construct | Fragment | cDNA Fragment size (bp) | Primers | Sequence | Oligo Anneal Temp (° C.) |
|---|---|---|---|---|---|
| ODR-10::$GFP^2$@AA240-241::RLuc(h) (Cterm) (OGOR) | (5') ODR-10::$GFP^2$ | 1452 | F: attB1 ODR-10Forward | AACCATGTCGGGAGAATTGTG (SEQ ID NO: 23) | 57.7 |
| | | | R: ODR-10-MidIC3GFP$^2$Jt2R | TGTAGCGCTCGCTTGTACAGCTCGTCCAT (SEQ ID NO: 24) | |
| | (3') ODR-10 | 321 | F: ODR-10-MidIC3GFP$^2$Jt2F | GAGCTGTACAAGCGAGCGCTACAGAAACAA (SEQ ID NO: 25) | 57.3 |
| | | | R: ODR-10-CtermRLuc(h)JtR | CTTGCTGGTCATCGTCGGAACTTGAGACA (SEQ ID NO: 26) | |
| | RLuc(h) (Cterm) | 949 | F: ODR-10-CtermRLuc(h)JtF | CAAGTTCCGACGATGACCAGCAAGGTGTA (SEQ ID NO: 27) | 56.5 |
| | | | R: attB2 RLuc(h)Reverse | GTTACTGCTCGTTCTTCA (SEQ ID NO: 28) | |
| | (3') ODR-10::RLuc(h) (Cterm) | 1246 | F: ODR-10-MidIC3GFP$^2$Jt2F | GAGCTGTACAAGCGAGCGCTACAGAAACAA (SEQ ID NO: 29) | 55.3 |
| | | | R: attB2 RLuc(h)Reverse | GTTACTGCTCGTTCTTCA (SEQ ID NO: 30) | |
| | ODR-10::$GFP^2$@AA240-241::RLuc(h) (Cterm) | 2675 | F: attB1 ODR-10Forward | AACCATGTCGGGAGAATTGTG (SEQ ID NO: 31) | 53.7 |
| | | | R: attB2 RLuc(h)Reverse | GTTACTGCTCGTTCTTCA (SEQ ID NO: 32) | |
| ODR-10::RLuc(h)@AA240-241::$GFP^2$ (Cterm) (OROG) | (5') ODR-10::RLuc(h) | 1669 | F: attB1 ODR-10Forward | AACCATGTCGGGAGAATTGTG (SEQ ID NO: 33) | 58 |
| | | | R: ODR-10-MidIC3RLuc(h)Jt2R | CTGTAGCGCTCGCTGCTCGTTCTTCAG (SEQ ID NO: 34) | |
| | (3') ODR-10 | 321 | F: ODR-10-MidIC3RLuc(h)Jt2F | AAGAACGAGCAGCGAGCGCTACAGAAACA (SEQ ID NO: 35) | 57.9 |
| | | | R: ODR-10-CtermGFP$^2$JtR | CTTGCTCACCATCGTCGGAACTTGAGACA (SEQ ID NO: 36) | |
| | GFP2 (Cterm) | 723 | F: ODR-10-CtermGFP$^2$JtF | CAAGTTCCGACGATGGTGAGCAAGGGCGA (SEQ ID NO: 37) | 56.3 |
| | | | R: attB2 GFP$^2$Reverse | GTTACTTGTACAGCTCGTC (SEQ ID NO: 38) | |
| | (3') Odr10::GFP2 (Cterm) | 1030 | F: ODR-10-MidIC3RLuc(h)Jt2F | AAGAACGAGCAGCGAGCGCTACAGAAACA (SEQ ID NO: 39) | 54.7 |
| | | | R: attB2 GFP$^2$Reverse | GTTACTTGTACAGCTCGTC (SEQ ID NO: 40) | |
| | Odr10::RLuc(h)@AA240-241::GFP2 (Cterm) | 2675 | F: attB1 ODR-10Forward | AACCATGTCGGGAGAATTGTG (SEQ ID NO: 41) | 53.0 |
| | | | R: attB2 GFP$^2$Reverse | GTTACTTGTACAGCTCGTC (SEQ ID NO: 42) | |

Components were then purified and placed in a paired reaction to denature at 94° C., anneal 52° C. (at overlapping primer sites) and extend 68° C. for 5 min for the required pairs. This was then used as template for PCR using the most 5' and 3' primers of the pairs. This was repeated until the full length constructs were made. They were then cloned into pGEM-T for sequencing. Error free clones were subcloned into pDONR201 (Invitrogen) using ApaLI. These were then subcloned into pYES-DEST52 (Invitrogen) using Gateway® technology (attB sites were included in original 5' and 3' primers) for subsequent expression in S. cerevisiae.

Construction of OGOR Mutant (H110Y)

Site-directed mutagensis was carried out with OGOR in pDONR201 vector (see above) as the double stranded template. The histidine 110 to tyrosine (H110Y) mutation was performed using the Stratagene Quickchange site directed mutagenesis kit according to standard protocols using the following primers; 5'-CACCAGTTTTGTTGTCTCAG-GAGTTTATTTTGTTTATCGATATTTTGCAACTT-3' (WT) (SEQ ID NO:43) and 5'-AAGTTGCAAAATATC-GATAAACAAAATAAACTCCTGAGACAACAAAACTG GTG-3' (H110Y antisense) (SEQ ID NO:44).

PCR was performed with Pfx50™ standard ingredients (Invitrogen) and conditions were as follows 94° C. 2 mins, 16 cycles of 94° C. 30 secs, 55° C. 1 minute, 68° C. 6.8 minutes. Following sequencing the OGOR mutant was then subcloned into pYES-DEST52 (Invitrogen) using Gateway® technology (5' and 3' attB sites were included in original OGOR sequence) for subsequent expression in S. cerevisiae.

Solution Preparations

20% (w/v) Glucose—Add 20 g of glucose to 100 mL of deionized water, heat on hot-plate (50° C.) until dissolved and filter purify (0.2 µm filters) solution.

20% (w/v) Raffinose—Add 20 g of glucose to 100 mL of deionized water, heat on hot-plate (50° C.) until dissolved and filter purify (0.2 µm filters) solution.

20% (w/v) Galactose—Add 20 g of galactose to 100 mL of deionized water, heat on hot-plate (50° C.) until dissolved and filter purify (0.2 µm filters) solution.

YPD medium—Add 20 g of bacteriological peptone, 10 g of yeast extract to 1 L of deionized water. Autoclave for 15 minutes.

YPD plates—Add 20 g of bacteriological peptone, 10 g of yeast extract and 20 g of agar to 1 L of deionized water. Autoclave for 15 minutes. Following autoclaving add 20 mL of 20% glucose and pour agar plates.

Yeast Synthetic prop-Out Media without Uracil (SCMM-U) medium—Add 6.7 g of yeast nitrogen base without amino acids (Product no. Y 0626, Sigma) and 1.92 g of yeast synthetic drop-out media supplement without uracil (Product no. Y 1501) to 1 L of deionized water. Autoclave for 15 minutes.

SCMM-U plates—Add 1.34 g of yeast nitrogen base without amino acids (Product no. Y 0626, Sigma), 0.384 g of yeast synthetic drop-out media supplement without uracil (Product no. Y 1501, Sigma) and 4 g of agar to 180 mL of deionized water. Autoclave for 15 minutes. Following autoclaving add 20 mL of 20% glucose and pour agar plates.

1× Sodium phosphate buffer (1×PBS, pH 7.4.)—A 10× stock solution was prepared by dissolving 82.33 g of sodium phosphate dibasic (0.58 M), 23.45 g of sodium phosphate monobasic (0.17 M) and 40 g sodium chloride (NaCl) in deionized water. The stock solution was diluted to a 1×PBS solution in deionized water.

Coelenterazine 400a—Dissolve 1 mg of Coelenterazine 400a (Clz400a, Biosynth) in 10.20 mL of pure ethanol to make a 250 µM stock solution. Pipette 40 or 400 µL aliquots of Coelenterazine 400a into microcentrifuge tubes and then dry down with a SpeedVac® Plus SC110A (Savant). Store aliquots at −80° C. Reconstitute samples in 100 or 1000 µL (40 or 400 µL aliquots, respectively) of absolute ethanol to give a concentration of 50 µM.

Odorant Preparation—A 1% stock solution of the odorants diacetyl, benzaldehyde and octanal were made up in the respective solvents water, ethanol and DMSO. The odorants were serially diluted in water to give the desired final concentration. The same dilutions of solvents without the addition of the odorants were also prepared.

Plasmid Transformation Protocol

Yeast transformations were carried out using a yeast transformation kit (YEAST-1, Sigma). A YPD plate was streaked with INVSC1 (Invitrogen) S. cervesiae strain and incubated at 28° C. for 2-3 days. Scrape a loop of InVSC1 cells from the YPD plate into a microcentrifuge tube. Resuspend cells in 0.5 mL of transformation buffer (Product code T 0809) and spin for 5 seconds. Remove the supernatant, leaving 50-100 µL of the buffer in the tube. Add 10 µL of 10 mg/mL salmon testes DNA (Product code D 9156) to the tube. Add 1 µg of the pYES-DEST52—OR plasmid DNA to be studied and vortex for 10 seconds. Add 600 µL of PLATE buffer (product code 8966) and vortex. Incubate for 4 hours at room temperature. Heat shock the sample for 15 minutes in a 42° C. heat block. Spin for 3 seconds in a microcentrifuge and remove the supernatant. Resuspend cells in 500 µL of sterile water. Plate 100 µL on SCMM-U plate. Incubate at 28° C. for 2-3 days until colonies appear.

Expression Protocol

Inoculate a single colony containing the pYES-DEST52—OR construct into 15 mL of SCMM-U media containing 2% glucose. Grow overnight at 28° C. with shaking (200 rpm).

The $OD_{600}$ of the overnight culture was determined. The amount of overnight culture required to obtain an $OD_{600}$ of 0.4 in 30 mL of induction medium (SCMM-U, 2% galactose, 2% raffinose) was removed and the cells pelleted at 1500×g for 5 minutes. The cells were resuspended in 1 mL of induction medium and inoculated into 29 mL of induction medium. Grow at 15° C. with shaking (200 rpm) for 72 hours. The culture was removed from the flask and the cells were centrifuged at 1500×g for 5 minutes at 4° C. Decant the supernatant and resuspend cells in 1 mL of sterile water. Transfer cells to a sterile microcentrifuge tube and centrifuge samples for 1 minute at 10,000×g. Remove the supernatant and carry out membrane isolation.

Membrane Preparations

Cells were harvested by centrifugation at 1500×g (4° C.) for 5 minutes, washed in water and resuspended in 4 mL of Dulbecco's phosphate buffered saline (D-PBS) or 1×PBS, containing 1000 mg/L glucose, 36 mg/L sodium pyruvate, calcium and magnesium (Invitrogen). The cells were lysed by French press (~18000 psi) and the soluble protein fractions were isolated by centrifugation at 9300×g (4° C.) for 15 minutes. Following this the soluble protein fraction was transferred to 13.15 mL polycarbonate thick wall centrifuge tubes and ultracentrifuged at 40,000 rpm (Beckman Coulter L-80 ultra-centrifuge) for 1 hour at 4° C. The supernatant was decanted and the membrane pellet resuspended in 1 mL of D-PBD or 1×PBS, and left overnight at 4° C. to solubilise.

Spectral Measurements

All spectral scans were recorded with a plate-reading SpectraMax M2 spectrofluorimeter (Molecular Devices). 100 µL aliquots of membrane preparations sample were scanned using 96-well plates (Perkin-Elmer). Fluorescence spectral scans recorded from 450 to 600 nm with an excitation wavelength of 420 nm using a 455 nm emission cut-off filter.

Simultaneous Dual Emission Detection

Simultaneous dual emission RET measurements were carried out with a POLARstar OPTIMA microplate reader (BMG LabTech). Simultaneous emission measurements used a BRET$^2$ filter set (410-80/515-30) with the set respective gains for each channel (3300/4095).

RET Analysis Protocol

Normalization of Sample Concentration

To assess the relative concentrations of BRET$^2$ tagged receptor samples the fluorescence intensity of the sample was determined from spectral scans and the sample amount normalized by the OGOR fluorescence intensity. To convert GFP$^2$ intensity into concentration purified GFP$^2$ protein was assayed at different concentrations to produce a calibration graph relating concentration to fluorescence intensity. GFP$^2$ proteins were purified using cobalt affinity chromatography according to the supplied instructions (BD Talon (BD Biosciences, Clontech)). Rearranging the line of best fit equation ($y=271x+233.31$) results in conversion of fluorescence intensity to concentration. An estimated concentration of 5 or 10 nM was used for assays in a final volume of 100 µL.

Selectivity

RET analysis was carried out in 96-well plates (Perkin-Elmer) and involved incubating the specified dual tagged receptor protein (OGOR) for 45 minutes with 1 µM of each particular odorant. The final volume was 100 µL and included 10 µL of odorant, receptor protein sample (see 'Normalization of sample concentration' section), D-PBS (or 1×PBS) and 5 µL of Clz400a (5 µM). A background signal was recorded by assaying a sample of D-PBS (or 1×PBS). During the incubation time the 96-well plate wells were sealed with Topseal™—A (Packard) with each sample area individually sealed. Non odorants samples (water, pyruvate, citric acid, lactic acid) were prepared and assayed first. Following this odorants solutions were prepared in the fume hood and assayed in the following order: 2-butanone, 2,3-pentanedione, 2,3-butanediol and diacetyl.

For BRET measurements Clz400a substrate (5 µM) was added following the 45 minute incubation time and the signal recorded using a 0.50s integration time over a 5 second period. Following addition of Clz400a the well was re-sealed while the signal was recorded to reduce cross-contamination of samples. The assays were sequentially carried out in the order the samples were added to the wells.

BRET$^2$ ratio is calculated as emission ratio measured as ((emission at 515 nm for receptor sample)−(emission at 515 nm for D-PBD (or 1×PBS))/(emission at 410 nm for receptor sample)−(emission at 410 nm for D-PBD) (or 1×PBS)).

Dose Response Curve

The OGOR concentration was normalized to 10 nM by GFP$^2$ intensity. A dose response curve was constructed by varying odorant concentrations over the concentration range as indicated in the text. The lowest concentration was always assayed first and the highest last.

A sigmoidal dose response curve was fitted, and $EC_{50}$ calculated, by non-linear regression analysis using GraphPad Prism for Windows XP.

Results

Ligand Response and Selectivity

The constructs produced have the BRET$^2$ donor and acceptor inserted within the third intracellular loop and at the C-terminus of the odorant receptor (FIG. 1). Diacetyl binding by ODR-10 would cause an increase in the BRET$^2$ ratio if the donor and acceptor components moved apart or an increase in the signal if the components moved closer together.

The BRET$^2$ signal was recorded following incubation of OGOR with 10 nM or 1 µM of the following ligands: water, pyruvate, citric acid, lactic acid, 2-butanone, 2,3-pentanedione, 2,3-butanediol and diacetyl (FIGS. 2a and b). The largest change in BRET$^2$ signal occurred upon incubating OGOR with µM concentrations of diacetyl, with a 37.5% difference in the signal compared to the solvent (water) response (FIG. 3a). This is the first example of monitoring ligand binding using a dual-labelled BRET$^2$ tagged receptor in a cell-free assay format.

The change in the BRET$^2$ ratio upon addition of both nM and µM concentrations of diacetyl to OGOR was significantly different (P>0.05) to the control response (water) (FIGS. 3a and b). The response of OGOR to diacetyl stimulation was the only response which was significantly different to the control response compared to all other ligands tested at both nM and µM concentrations. These results confirm that ODR-10 selectively binds diacetyl. Diacetyl was previously confirmed to be the only volatile compound to produce a $Ca^{2+}$ elevation response in ODR-10 expressing HEK 293 cells (Zhang et al., 1997).

The largest change in the BRET$^2$ response to ligand binding of 37.5% is substantially greater than the observed change in the FRET signal (~5%) upon binding of 10 nM norepinephrine by the $\alpha_{2A}$ receptor (Lohse et al., 2003) and 1 µM PTH by PTHR (~20%) (Vilardaga et al., 2003). The decrease in BRET$^2$ signal upon addition of diacetyl suggests that the BRET$^2$ components move apart upon odorant binding. This is the first demonstration that this BRET$^2$ transduction system exhibits superior sensitivity compared to a FRET transduction system for monitoring intramolecular changes.

Dose Response

The effect of changing odorant concentrations on the amplitude of the change in the BRET$^2$ signal of OGOR (FIG. 4) provides the first demonstration of a dose-dependent response. The $EC_{50}$ value was calculated to be 3.55 fM diacetyl, which is equivalent to 0.31 parts per quadrillion (ppq). The apparent affinity of ODR-10 for diacetyl when expressed in human cells, and monitored by calcium imaging technique, was calculated to be 2.3 µM (~0.2 part per million (ppm)), an $EC_{50}$ value consistent with chemotaxis results (Zhang et al., 1997).

The cell free assay presented here is more than nine orders of magnitude more sensitive for diacetyl quantification compared to whole cell assays and existing chemical detection systems such as fluorescence detection (Li et al., 2009) and a gas chromatographic technique with flame ionization detection (GC-FID) (Macciola et al., 2008).

Negative Control—OGOR Mutation (H110Y)

An ideal negative control for the OGOR response to diacetyl would place the BRET$^2$ components the same distance apart as in the OGOR receptor but the receptor would be unresponsive to diacetyl itself. Replacing the histidine with a tyrosine at position 110 in the 3$^{rd}$ membrane spanning residue of ODR-10 resulted in a strongly defective chemotaxis response to diacetyl (Troemel et al., 1995; Sengupta et al., 1996).

The introduction of a histidine 110 to tyrosine (H110Y) mutation to the OGOR construct reduced the response to µM concentrations of diacetyl from 32.4% for OGOR to 4.1% (FIG. 5). This reduced response to diacetyl was not significantly different (P<0.05) from the solvent (water) response indicating the mutation caused a loss of function. This infers that the response of OGOR to diacetyl is due to diacetyl interacting with the ODR-10 receptor and not non-specifically with the BRET$^2$ components themselves.

Example 2

Comparison of Dual-Labelled Fret ODR-10 (OCOY) To Dual-Labelled BRET$^2$ ODR-10 (OGOR)

To compare the sensitivity of the BRET$^2$ system to the FRET system for monitoring GPCR activation the BRET$^2$ components used to tag the ODR-10 receptor (OGOR) were replaced with FRET components resulting in the insertion of CFP into the 3$^{rd}$ intracellular loop and YFP at the C-terminus (OCOY). The CFP (mCFP) (SEQ ID NO:45) and YFP (mCitrine) (SEQ ID NO:46) derivatives were both monomeric and codon optimized (EUROSCARF) for yeast expression (SEQ ID NOs 47 and 48 respectively).

Materials and Methods

The OCOY sequence flanked by KpnI and XhoI restriction sites was synthesised by Genscript. The OCOY sequence was inserted into the KpnI and XhoI sites of the pENTR11 vector. These were then recombined into pYES-DEST52 (Invitrogen) using Gateway® technology for subsequent expression in *S. cerevisiae*. The OCOY coding sequence is provided as SEQ ID NO:49, whereas the amino acid sequence is provided as SEQ ID NO:50.

OCOY Expression

The same expression protocol was used for the expression of OCOY in InVSC1 as for OGOR expression.

Concentration Normalization

To assess the relative concentrations of dual-tagged receptor samples the fluorescence intensity of the sample was determined from spectral scans and the sample amount normalized by the OCOY fluorescence intensity. The YFP intensity (530 nm) was normalized to 721.32 a.u. for OCOY. 50 µL of OCOY was pipetted into the appropriate well and the volume made up to 100 µL with 1×PBS.

Results

Ligand Response

There was a 7.6% reduction in FRET ratio (intensity at 520 nm/intensity at 480 nm) of OCOY in response to µM concentrations of diacetyl compared to a 32.4% reduction for OGOR (FIG. 6). The OCOY response was shown to be significantly different (P<0.05) to the solvent (water) response. OGOR was shown to be more than four times more sensitive for monitoring diacetyl binding than OCOY.

The Förster distance ($R_0$), the RET probe separation corresponding to 50% of the maximum RET efficiency, for the BRET$^2$ system was recently determined to be 7.5 nm, the largest $R_0$ value determined for any genetically encoded RET pair (Dacres et al., 2009). The $R_0$ value for the FRET system was previously determined to be 4.8 nm (Evers et al., 2006) indicating that the BRET$^2$ system is able to probe a larger distance range (3.8-11.3 nm) than the FRET system (2.4-7.2 nm). The measured transfer efficiency for OGOR changed from 64.3% to 47% upon the addition of diacetyl (1 µM) indicating a distance change of 6.8 nm to 7.6 nm. A system with a Förster distance of 4.8 nm, such as the FRET system, would only exhibit a transfer efficiency change of 11.3% to 6.0% upon addition of diacetyl for this distance change. This confirms that the BRET$^2$ system is more suitable, in terms of detection sensitivity, for the measurement of this distance change in this distance range.

OCOY Dose Response Curve

Following the confirmation that the OCOY response to diacetyl was significantly different to the solvent (water) response a dose response was plotted. To generate this data spectral scans were recorded upon the addition of different concentrations of diacetyl (FIG. 7). As the concentration of diacetyl increased from $1\times10^{-21}$ M to $1\times10^{-10}$ M there was a decrease in the YFP emission intensity and an accompanying increase in CFP emission intensity (FIG. 7). Scaling the OCOY response with respect to the normalized OGOR response curve (FIG. 8) confirmed that BRET$^2$ detection is more sensitive than FRET detection for monitoring diacetyl binding by ODR-10. The calculated log EC50 value for the FRET detection system was −16.43±0.9741 M (mean±SEM, n=5) which is not significantly different (P<0.05) to the calculated log EC50 value of −14.43±0.5468 (mean±SEM, n=12) for the BRET$^2$ system. This demonstrates that the ODR-10 affinity for diacetyl is statistically similar for both detection systems inferring that diacetyl is specifically interacting with the ODR-10 receptor and not with the RET components themselves.

Example 3

Dual-Tagged Str112 (TGTR)

Materials and Methods

The TGTR sequence flanked by NcoI and NotI restriction sites was synthesised by Genscript. The TGTR sequence was inserted into the NcoI and NotI sites of the pENTR11 vector. These were then recombined into pYES-DEST52 (Invitrogen) using Gateway® technology for subsequent expression in *S. cerevisiae*.

TGTR Expression

The same expression protocol was used for the expression of TGTR in InVSC1 as for OGOR expression. The TGTR coding sequence is provided as SEQ ID NO:51, whereas the amino acid sequence is provided as SEQ ID NO:52.

RET Analysis Protocol

The same RET analysis protocol as described for the OGOR selectivity studies. 1 µM of the ligands pyruvic acid, citric acid, ethyl acetate, acetoin and diacetyl was assayed with 10 nM of TGTR Preparation of Bacterial Extract Assays The bacterial strain OP50 was grown in LB overnight at 37° C. with shaking (200 rpm). *E. coli* strain OP50 is usually used as a food source for nematode growth in the laboratory (Brenner, 1974). Two assays were performed using the OP50 bacterial culture. The first assay was the addition of 10 µL of the bacterial culture or 10 µL of LB to 10 nM TGTR. The second assay required that 1 mL of the bacterial culture was placed in a microcentrifuge tube and centrifuged at 10000×g for 1 minute. 10 µL of the supernatant, following decanting into a fresh microcentrifuge tube, or 10 µL of LB was added to 10 nM TGTR. Following bacterial sample addition the same protocol was followed as for the OGOR RET analysis.

Results

The response of TGTR to the addition of 10 µL of OP50 bacterial supernatant or bacterial culture in LB was significantly different (P≤0.05) to that of LB alone (FIG. 9). Stimulating the Str112 receptor to a complex odorant mixture as released from OP50 during growth causes an increase in the BRET$^2$ ratio suggesting that the BRET$^2$ components move towards each other upon odorant binding.

A number of ligands were tested individually (FIG. 10) and both pyruvic acid and acetoin produced significantly higher BRET$^2$ signals (P≤0.05) compared to the response of TGTR to water. This confirms that upon ligand binding the BRET$^2$ components move towards each other. An increase of 20.8% in the BRET$^2$ signal in response to acetoin is four times greater than the response of the FRET tagged $\alpha_{2A}$ adrenergic receptor to norepinephrine (Lohse et al., 2003). This is the first demonstration of odorant binding by the Str112 nematode receptor and also the first example of monitoring odorant binding by BRET$^2$ tagged Str112.

Example 4

Receptor Chimeras

An ODR-10 transduction cassette is engineered so the ODR-10 N-terminus (aa1-32) and IC3 to C terminus (aa225-aa339) with BRET tags flank a multiple cloning site (FIG. 11). The chimeric receptors are expressed in yeast. Ligand binding regions of ORs are shuffled "in-frame' into this cassette and these chimeric receptors can be used to assess ligand binding by BRET.

Example 5

Oligomerization of Olfactory Receptors

Odr10 labelled with Rluc at the C-terminus (SEQ ID NO:17) and Odr10 labelled with GFP2 at the C-terminus (SEQ ID NO:19) were co-expressed in yeast to show receptor oligomerization and BRET modulation.
Materials and Methods
Transformant Culture and Tagged-Gene Induction Conditions
A colony of transformed yeast cells was grown in yeast synthetic drop-out medium (SCMM, Sigma) lacking appropriate nutrients (such as uracil (U), tryptophan (T)) to select for plasmid-containing cells with 2% glucose for overnight at 28° C. with shaking 190 rpm; SCMM-U-T for Invsc1 co-expressed pYesDest52-Odr10-Rluc and pDestpESC-Odr10-GFP2 (Invsc1/OR/OG), SCMM-U for Invsc1 expresses pVV214-odr10-Rluc (Invsc1/OR) alone and pYesDest52 odr10-GFP2 (Invsc1/OG) alone respectively.

After overnight culture, OD600 was determined and the cells were suspended in induction medium (with 2% galactose and 1% raffinose instead of glucose as the culture medium) to give a final OD600 of 0.4. This induction culture was incubated for 24 hours with shaking at 15° C. to induce fusion receptor expression. The culture was then pelleted and washed twice with cold phosphate-buffered saline (PBS). Cell pellet can be stored at −80° C. and suspended in PBS buffer just before the BRET$^2$ assay.
Quantification of Yeast Cells for BRET$^2$ Assay First Invsc1/OR/OG was quantified by GFP intensity (about 3000 RLU or c.p.s in 100 µl per well) by direct excitation of GFP$^2$ at Ex420 nm in a white 96-well microplate (Perkin Elmer) using a SpectraMax M2 spectrofluorometer (Molecular Devices). The Renilla luciferase activity of the quantified Invsc1/OR/OG cells was determined by adding luciferin coelenterazine native (final concentration 5 µM) into a total volume of 100 µl cell in a 96-well white microplate and measuring luminescence signals immediately (Polarstar Optima, BMGLABTECH).

Invsc1/OG was normalised to have the similar GFP intensity as Invsc1/OR/OG. Invsc1/OR was normalised to have the similar Rluc activity as Invsc1/OR/OG. Negative control (host strain) Invsc1 was quantified to have same cell density as Invsc1/OR/OG.
Microplate BRET$^2$ Cell Based Assay Assay procedure was modified from Issad and Jockers (2006) and conducted in a 96-well white microplate in a total volume of 100 µl and two repeat for each sample. Three biological independent assays will be conducted and data are pooled. Coelenterazine h DeepBlueC substrate (Biosynth AG) was added at a final concentration of 10 µM, and readings were performed with a dual wavelength lumino/fluorometer mircoplate reader (BMGLabtech). The following optimized filter settings were used to measure Rluc light emission (410±80 nm) and GFP$^2$ light emission (515±30 nm). The BRET ratio was defined as the difference of the emission at 515 nm/410 nm of co-expressed Rluc and GFP2 fusion proteins and the emission at the 515 nm/410 nm of the Rluc fusion protein alone. Results were expressed in milliBRET units, 1 milliBRET corresponding to the BRET ratio value multiplied by 1000 (Ayoub, 2002). Illumination of control cells (host strain Invsc1) that do not express a Rluc or GFP2 fusion at the same settings results in detection of cell autofluorescencee. Subtraction of the autofluorescence from all tested samples was taken place before BRET ratio values were calculated.
Crude Membrane Preparation, Solubilisation, and Immunoprecipitation Properly induced yeast cells (GFP$^2$ level was not more than 2 fold over background of host strain Invsc1 cells) were washed three times with ice-cold Buffer A (75 mM tris-HCl, pH7.4, 12 mM MgCl2 and 2 mM EDTA) and the final pellet was suspended in Buffer B (Buffer A+protease inhibitor cocktail, complete Mini EDTA-free (Roche Applied Science)). Then the yeast cells are disrupted using a French Press and centrifuged for 15 mins at 10,000×g at 4° C. The supernatant was ultracentrifuged for 1 hour at 130000×g and the pellet was suspended in cold Buffer B.

Membrane protein solubilisation and immunoprecipitation procedures were modified according to the method described by Ayoub et al. (2002). Crude membrane was solubilised with 0.5% digitonin (Sigma) and this mixture was stirred for 3 h at 4° C. Non-solubilised membrane proteins were removed by centrifugation at 18,000×g for 30 mins at 4° C. The digitonin concentration was adjusted to 0.2% using cold Buffer B and the polyclonal anti-GFP antibodies (Sapphire Bioscience, Cat No 120-29000) were added to a final dilution of 1:1000. Immune complex formation was allowed to proceed for 12 h at 4° C. with gentle agitation and Protein A-agarose suspension (Sigma) was added to a final volume of 1:10 (agarose suspension:sample) for incubation for another 6 h with gentle agitation at 4° C. After centrifugation for 1 min at 5000×g, supernatant was decanted and the agarose beads washed five times with 0.5 ml of cold Buffer C (Buffer B+0.2% digitonin). Precipitates were analysed by assessing luciferase activity in a luminometer (BMGLabtech) using coelenterazine as substrate (Biosynth AG, Switzerland).
Results
Visualisation of Nematode odr-10 in Yeast Cells—Confocal Microscopy Confocal image of yeast strain Invsc1 co-expressed odr-10-Rluc and odr-10-GFP$^2$ after 24 hour induction reveals that GFP2 fusion protein mostly only expressed on the membrane of the cells and no over-expression of tagged odr-10 observed. About 32% of the cells expressed tagged odr-10 protein. Increasing induction time up to 48 hours, confocal image shows GFP$^2$ over-expression in the cells and aggregated GFP2 particles observed in the cytosol of the cells (FIG. 12).
Detection of Constitutive odr-10 Oligomers in Living Yeast Cells by BRET$^2$ BRET$^2$ experiment results shows that significant energy transfer was observed in yeast cells co-expressing odr-10-Rluc and odr-10-GFP$^2$ (FIG. 13) indicating that odr-10 forms homo-oligomers. No significant energy transfer was obtained in the sample at which half yeast cells expressed odr-10-Rluc and another half cells expressed odr-10-GFP2.

Detection of Constitutive Odr-10 Oligomers in Living Yeast Cells by Immunoprecipitation Oligomerisation of Odr-10 in the living yeast cells was confirmed by the pairwise expression of receptor-Rluc and -GFP$^2$ fusion, followed by precipitation using anti-green fluorescence protein antibodies and measuring co-immunoprecipitated luciferase activity. The results represented in FIG. 14 indicate that Odr-10 forms oligomers in the cells. To rule out the possibility that co-immunoprecipitation could result from receptor-independent, interaction between the GFP$^2$ and the Rluc, co-immunoprecipitation was also carried out using (1) odr-10-Rluc/GFP$^2$, (2) the mixture of solubilised membranes which either expressed receptor-GFP$^2$ or receptor-Rluc. Results from those samples in which less than 20% of luciferase activity was recovered comparing to co-expression of odr-10-GFP$^2$ and odr-10-Rluc in the same cells suggested the interaction between co-expressing odr-10-GFP$^2$ and odr-10-Rluc fusion proteins was specific.

Example 6

BRET$^2$ Tagged Mouse $\alpha_{2A}$ Adrenergic Receptor

The mouse $\alpha_{2A}$ adrenergic receptor (SEQ ID NO:56) was engineered so that the GFP$^2$ was inserted into the 3$^{rd}$ intracellular loop with its N-terminus following Ala250 and its C-terminus adjacent to Arg372. RLuc was fused to Val461 in the C-terminus of the receptor (amino acid sequence provided as SEQ ID NO:54 and encoding open reading frame as SEQ ID NO:53).

The dual-tagged adrenergic receptors are expressed in yeast. These receptors can be used to monitor ligand binding by the mouse $\alpha_{2A}$ adrenergic receptor via changes in the BRET$^2$ ratio.

Example 7

Whole-Cell Vs Cell-Free Bret Assay

Comparison of the cell-free assay system of the invention to a whole cell assay system demonstrates that the intensity of the BRET$^2$ signal was more than forty time greater, in terms of light output when measured in the RLuc channel, for the cell-free assay compared to the whole-cell assay (FIG. 15). Assaying 1 µM of diacetyl resulted in no significant change (P≤0.05) in the BRET$^2$ signal using the whole cell assay, whereas a significant decrease (P≤0.05) of 52% was observed using a cell-free assay system (FIG. 16).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/148,271 filed 29 Jan. 2009, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

References

Aloni et al. (2006) Genome Biol. 7:R88.
Ayoub et al. (2002) J. Biol. Chem. 277:21522-28.
Brenner (1974) Genetics 77:71-94.
Buck and Axel Cell (1991) 65: 175-187.
Celic et al. (2003) Biochemistry 42: 3004-3017.
Charest et al. (2005) EMBO Reports 6: 334-340.
Cuppen et al. (2003) Comp Funct Genomics 4:479-491.
Dacres et al. (2009) Anal. Biochem. 385:194-202.
Day et al. (2004) Luminescence 19:8-20.
de Wet et al. (1987) Mol. Cell. Biol. 2987:725-737.
Evers et al. (2006) Biochemistry 45: 13183-13192.
Feldmesser et al. (2006) BMC Genomics.7:121.
Frishman and Argos (1997) Proteins 27:329-335.
Fuchs et al. (2001) Human Genetics 108:1-13.
Gaillard et al. (2004) Cellular and Molecular Life Sciences 61: 456-469.
Ghanouni et al. (2001) proc. Natl. Acad. Sci. USA 98:5997-96002.
Glusman et al (2001) Genome Res. 11:685-702.
Glusman et al. (2000a) Mammalian Genome 11: 1016-1023
Glusman et al. (2000b) Genomics 63: 227-245.
Graschopf et al. (2001) J. Biol. Chem. 276:16216-16222.
Greer and Szalay (2002) Luminescence 17:43-74.
Harayama (1998) Trends Biotechnol. 16:76-82.
Hastings (1996) Gene 173:5-11.
Hoffman et al. (2005) Nature Methods 2:171-176.
Hofmann et al. (2009) Trends Biochem Sci 34:540-552.
Hofmann and Stoffel (1993) Biol. Chem. 374:166.
Hushpulian et al. (2007) Biotransformation 25:2-4.
Inouye et al. (1997) Biochem. J. 233:349-353.
Issad and Jockers (2008) Methods Mol. Biol. 332:195-209.
Jansen et al. (1999) Nat. Genet. 21:414-419.
Kaiser et al. (2008) Proc Natl Acad Sci USA 105:15726-31.
Klein et al. (1984) Biochim. Biophys. Acta 787:221-226
Kobilka et al. (2007) Biochimica et Biophysica Acta1768: 794-807.
Lander et al. (2001) Nature 409:860-921.
Li et al. (2009) Journal of Fluorescence 19:601-606.
Lisenbee et al. (2007) Molecular Endocrinology May 15: 17505057.
Lohse et al. (2003) Life Sciences. 74: 397-404.
Lohse et al. (2007) Current Opinion in Pharmacology 7: 547-553.
Lorenz et al. (1991) Proc. Natl. Acad. Sci. USA 88:4438-4442.
Macciola et al (2008) Food Control 19:873-878.
Milligan (1999) Trends Pharmacol. Sci. 20:118-124.
Moore et al. (1994) Methods Enzymol. 228:448-450 9.
Nakanishi et al. (2006) Biochemical and Biophysical Research Communications 343:1191-1196.
Needleman and Wunsch (1970) J. Mol. Biol. 45:443-453.
Neves et al. (2002) Science 296:1636-1639.
Niimura and Nei (2003) Proc. Natl. Acad. Sci. USA. 100: 12235-12240.
Oldenburg (1998) Annu. Rep. Med. Chem. 33:301-311.
Oldham abd Hamm (2008) Nature 9:60-71.
Olender et al. (2004a) Genet Mol. Res. 3:545-53.
Olender et al. (2004b) Genomics. 83:361-72.
Persson and Argos (1994) J. Mol. Biol. 237:182-192.
Persson and Jergil (1994) Analytical Biochemistry 204: 131-136.
Pfleger and Eidne (2006) Nature Methods 3:165-174.
Pilpel and Lancet (1999) Protein Science 8: 969-77.
Piston et al. (2007) TRENDS in Biochemical Sciences 32: 407-414.
Pope (1999) Drug Discovery Today 4:350-362.

Rieder and Emr (2001) Curr. Protocol. Cell. Biol. Ch. 3; Unit 3.8.
Robertson (1998) Genome Research 8:449-463.
Robertson (2001) Chem Senses 26:151-159.
Rochais et al. (2007) The Journal of Clinical Investigation 117: 229-235.
Sengupta et al. (1996) Cell 84:899-909.
Sharon et al. (1998) Ann N Y Acad. Sci. 30; 855:182-93
Spencer (1998) Biotechnol. Bioeng. 61:61-67.
Strop et al. (2007) J. Biol. Chem. 283:1113-1119.
Troemel et al. (1995) Cell 83: 207-218.
Trueheart and Fink (1989) Proc. Natl. Acad. Sci. USA. 86:9916-9920.
Tsien (1998) Ann. Rev. Biochem. 63:509-544.
Verhaegen et al. (2002) Anal. Chem. 74: 4378-4385
Vilardaga (2003) Nature Biotechnology 21: 807-812.
Viviani (2002) Cell. Mol. Life. Sci. 59:1833-1850.
von Heijne (1992) J. Mol. Biol. 225:487-494.
Wang et al (1997) In Bioluminescence and chemiluminescence: molecular reporting with photons, Wiley, NY, pp 419-422.
Xu et al. (1999) Proc. Natl. Acad. Sci. USA. 96:151-156.
Young et al. (2002) J. Human Mol. Genet. 11:535-4.
Zhang and Firestein (2002) Nat. Neurosci. 5:81.
Zhang et al. (1997) PNAS 94: 12162-12167.
Zozulya et al. (2001) Genome Biol. 2:0018.1-0018.12.

---

The invention claimed is:

1. A method of detecting a compound, the method comprising, i) contacting a sample with a cell-free composition comprising at least one G protein coupled receptor embedded in a lipid bilayer, and which is capable of binding the compound, wherein the G protein coupled receptor comprises one or more subunits that are the same or different, and wherein at least one of the subunits of the G protein coupled receptor comprises a bioluminescent protein and an acceptor molecule, ii) simultaneously or sequentially with step i) providing a substrate of the bioluminescent protein, and allowing the bioluminescent protein to modify the substrate, iii) determining if step ii) modulates bioluminescent resonance energy transfer (BRET) between the bioluminescent protein and the acceptor molecule, wherein the spatial location and/or dipole orientation of the bioluminescent protein relative to the acceptor molecule is altered when the compound binds the G protein coupled receptor, and wherein when expressed in a cell the N-terminus of the G protein coupled receptor, or subunits thereof, is outside the cell and the C-terminus inside the cell, and wherein the amplitude of the change in the BRET ratio is indicative of the relative amount of the compound in the sample, wherein a) the bioluminescent protein forms part of the fifth non-transmembrane loop of the subunit, and the acceptor molecule forms part of the C-terminus, or b) the acceptor molecule forms part of the fifth non-transmembrane loop of the subunit, and the bioluminescent protein forms part of the C-terminus, and wherein the method is at least 2 fold more sensitive than if a non-bioluminescent protein is used as a donor molecule and a modulation of fluorescence resonance energy transfer (FRET) is determined.

2. The method of claim 1, wherein the method is performed using microfluidics.

3. The method of claim 1, wherein the Förster distance of the bioluminescent protein and the acceptor molecule is between 6.8 and 7.6nm.

4. The method of claim 2, wherein the Förster distance of the bioluminescent protein and the acceptor molecule is between 6.8 and 7.6nm.

5. The method of claim 3, wherein the Förster distance of the bioluminescent protein and the acceptor molecule is 7.5nm.

6. The method of claim 4, wherein the Förster distance of the bioluminescent protein and the acceptor molecule is 7.5nm.

7. The method of claim 1, wherein
i) the subunit comprises the N-terminus and at least a majority of the first transmembrane domain of a first G protein coupled receptor subunit, at least a majority of the first non-transmembrane loop through to at least a majority of the fifth transmembrane domain of a second G protein coupled receptor subunit, and at least a majority of the fifth non-transmembrane loop through to the C-terminal end of the first G protein coupled receptor subunit, or
ii) the subunit comprises the N-terminus through to at least a majority of the fifth transmembrane domain of a first G protein coupled receptor subunit, and at least a majority of the fifth non-transmembrane loop through to the C-terminal end of a second G protein coupled receptor subunit.

8. The method of claim 2, wherein
i) the subunit comprises the N-terminus and at least a majority of the first transmembrane domain of a first G protein coupled receptor subunit, at least a majority of the first non-transmembrane loop through to at least a majority of the fifth transmembrane domain of a second G protein coupled receptor subunit, and at least a majority of the fifth non-transmembrane loop through to the C-terminal end of the first G protein coupled receptor subunit, or
ii) the subunit comprises the N-terminus through to at least a majority of the fifth transmembrane domain of a first G protein coupled receptor subunit, and at least a majority of the fifth nontransmembrane loop through to the C-terminal end of a second G protein coupled receptor subunit.

9. The method of claim 1, wherein
i) the bioluminescent protein is a luciferase, and/or
ii) the substrate is luciferin, coelenterazine, or a derivative of coelenterazine, and/or
iii) the acceptor molecule which is a protein is green fluorescent protein (GFP), or a biologically active variant or fragment of any one thereof.

10. The method of claim 2, wherein
i) the bioluminescent protein is a luciferase, and/or
ii) the substrate is luciferin, coelenterazine, or a derivative of coelenterazine, and/or
iii) the acceptor molecule which is a protein is green fluorescent protein (GFP), or a biologically active variant or fragment of any one thereof.

11. The method of claim 9, wherein the luciferase is a *Renilla* luciferase, the acceptor molecule is GFP, and the substrate is Coelenterazine 400a.

12. The method of claim 10, wherein the luciferase is a *Renilla* luciferase, the acceptor molecule is GFP, and the substrate is Coelenterazine 400a.

13. The method of claim 1, wherein
i) the cell-free composition was obtained by producing the G protein coupled receptor in a recombinant cell and disrupting the membrane of the cell, or
ii) the G protein coupled receptor is embedded in the lipid bilayer of a liposome.

14. The method of claim 2, wherein
i) the cell-free composition was obtained by producing the G protein coupled receptor in a recombinant cell and disrupting the membrane of the cell, or
ii) the G protein coupled receptor is embedded in the lipid bilayer of a liposome.

15. The method of claim 13, wherein the recombinant cell is a yeast cell.

16. The method of claim 14, wherein the recombinant cell is a yeast cell.

17. The method of claim 1, wherein
i) the G protein coupled receptor is an odorant receptor, or
ii) the subunit is a chimera of a portion of two or more different G protein coupled receptor subunits.

18. The method of claim 2, wherein
i) the G protein coupled receptor is an odorant receptor, or
ii) the subunit is a chimera of a portion of two or more different G protein coupled receptor subunits.

19. A method for screening for a compound that binds a G protein coupled receptor, the method comprising,
i) contacting a candidate compound with a cell-free composition comprising at least one G protein coupled receptor embedded in a lipid bilayer, and which is capable of binding the compound, wherein the G protein coupled receptor comprises one or more subunits that are the same or different, and wherein at least one subunit of the G protein coupled receptor comprises a bioluminescent protein and an acceptor molecule,
ii) simultaneously or sequentially with step i) providing a substrate of the bioluminescent protein, and allowing the bioluminescent protein to modify the substrate,
iii) determining if step ii) modulates bioluminescent resonance energy transfer (BRET) between the bioluminescent protein and the acceptor molecule, wherein a modulation of BRET indicates that the compound binds the G protein coupled receptor, and wherein when expressed in a cell the N-terminus of the G protein coupled receptor, or subunits thereof, is outside the cell and the C-terminus inside the cell, and wherein the amplitude of the change in the BRET ratio is indicative of the relative amount of the compound in the sample, wherein
a) the bioluminescent protein forms part of the fifth non-transmembrane loop of the subunit, and the acceptor molecule forms part of the C-terminus, or
b) the acceptor molecule forms part of the fifth non-transmembrane loop of the subunit, and the bioluminescent protein forms part of the C-terminus, and wherein the method is at least 2 fold more sensitive than if a non-bioluminescent protein is used as a donor molecule and a modulation of fluorescence resonance energy transfer (FRET) is determined.

* * * * *